US008703701B2

(12) United States Patent
DiMarchi

(10) Patent No.: US 8,703,701 B2
(45) Date of Patent: Apr. 22, 2014

(54) GLUCAGON/GLP-1 RECEPTOR CO-AGONISTS

(75) Inventor: Richard D. DiMarchi, Carmel, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 13/515,977

(22) PCT Filed: Dec. 9, 2010

(86) PCT No.: PCT/US2010/059724
§ 371 (c)(1),
(2), (4) Date: Jun. 14, 2012

(87) PCT Pub. No.: WO2011/075393
PCT Pub. Date: Jun. 23, 2011

(65) Prior Publication Data
US 2012/0288511 A1  Nov. 15, 2012

Related U.S. Application Data

(60) Provisional application No. 61/288,248, filed on Dec. 18, 2009.

(51) Int. Cl.
*A61K 38/26* (2006.01)
*A61P 3/10* (2006.01)

(52) U.S. Cl.
USPC .......................................... 514/6.8; 514/7.2

(58) Field of Classification Search
None
See application file for complete search history.

(56) References Cited

U.S. PATENT DOCUMENTS

| | | | |
|---|---|---|---|
| 4,275,152 A | 6/1981 | Esders et al. |
| 5,359,030 A | 10/1994 | Ekwuribe |
| 5,510,459 A | 4/1996 | Smith et al. |
| 5,512,549 A | 4/1996 | Chen et al. |
| 5,665,705 A | 9/1997 | Merrifield et al. |
| 5,783,674 A | 7/1998 | Geysin et al. |
| 6,191,102 B1 | 2/2001 | DiMarchi et al. |
| 6,583,111 B1 | 6/2003 | DiMarchi et al. |
| 6,677,136 B2 | 1/2004 | Marshall et al. |
| 7,192,922 B2 | 3/2007 | Shannon et al. |
| 7,211,557 B2 | 5/2007 | DiMarchi et al. |
| 7,576,059 B2 | 8/2009 | Jonassen et al. |
| 2003/0021795 A1 | 1/2003 | Houston et al. |
| 2003/0143183 A1 | 7/2003 | Knudsen et al. |
| 2003/0204063 A1 | 10/2003 | Gravel et al. |
| 2004/0002468 A1 | 1/2004 | Wadsworth et al. |
| 2004/0235710 A1 | 11/2004 | DeFilippis et al. |
| 2005/0070469 A1 | 3/2005 | Bloom et al. |
| 2005/0095679 A1 | 5/2005 | Prescott et al. |
| 2005/0124550 A1 | 6/2005 | Peri |
| 2005/0153890 A1 | 7/2005 | Pan et al. |
| 2005/0288248 A1 | 12/2005 | Pan et al. |
| 2006/0003417 A1 | 1/2006 | Pan et al. |
| 2006/0003935 A1 | 1/2006 | Pan et al. |
| 2006/0171920 A1 | 8/2006 | Shechter et al. |
| 2006/0210534 A1 | 9/2006 | Lee et al. |
| 2006/0252916 A1 | 11/2006 | DiMarchi et al. |
| 2006/0286129 A1 | 12/2006 | Sarubbi |
| 2007/0042956 A1 | 2/2007 | Johansen et al. |
| 2007/0173452 A1 | 7/2007 | DiMarchi et al. |
| 2007/0203058 A1 | 8/2007 | Lau et al. |
| 2007/0287670 A1 | 12/2007 | Natarajan et al. |
| 2008/0125574 A1 | 5/2008 | Sheffer et al. |
| 2008/0318837 A1 | 12/2008 | Quay et al. |
| 2009/0036364 A1 | 2/2009 | Levy et al. |
| 2009/0054305 A1 | 2/2009 | Schlein et al. |
| 2009/0062192 A1 | 3/2009 | Christensen et al. |
| 2009/0074769 A1 | 3/2009 | Glaesner et al. |
| 2009/0137456 A1 | 5/2009 | DiMarchi et al. |
| 2009/0192072 A1 | 7/2009 | Pillutla et al. |
| 2010/0190699 A1 | 7/2010 | DiMarchi et al. |
| 2010/0190701 A1 | 7/2010 | Day et al. |
| 2011/0065633 A1 | 3/2011 | DiMarchi et al. |
| 2011/0098217 A1 | 4/2011 | DiMarchi et al. |
| 2011/0166062 A1 | 7/2011 | DiMarchi et al. |
| 2011/0190200 A1 | 8/2011 | DiMarchi et al. |
| 2011/0257092 A1 | 10/2011 | DiMarchi et al. |
| 2011/0288003 A1 | 11/2011 | DiMarchi et al. |

FOREIGN PATENT DOCUMENTS

| | | |
|---|---|---|
| CA | 2024855 | 3/1992 |
| EP | 0220958 | 5/1987 |
| EP | 0479210 | 4/1992 |
| EP | 0815135 | 9/1996 |

(Continued)

OTHER PUBLICATIONS

PCT International Search Report and Written Opinion completed by the ISA/US on May 26, 2011.
Day, et al. A New Glucagon and GLP-1 Co-Agonist Eliminates Obesity in Rodents Nature Chemical Biology Jul. 13, 2009, 5(10); 749-757; Table 1; Fig.1A; Abstract; p. 751, col. 1, Para 2 to col. 2, Para 1; p. 755, col. 1, Para 3.
Murphy, et al. Potent Long-Acting Alkylated Analogs of Growth Hormone-Releasing Factor Pept Res. 1988, 1 (1):36-41; abstract.
"Novel Glucagon-Based Peptides—Virtues of Combinatorial Pharmacology," AAPS 2005, San Francisco, California.

(Continued)

*Primary Examiner* — Gyan Chandra
(74) *Attorney, Agent, or Firm* — Barnes & Thornburg LLP

(57) ABSTRACT

Provided herein are glucagon analogs comprising a modified amino acid sequence of native human glucagon (SEQ ID NO: 2) that exhibit activity at the glucagon receptor, activity at the GLP-1 receptor, or activity at each of the glucagon receptor and the GLP-1 receptor. In some embodiments, the glucagon analog exhibits at least 100% or more of the activity of native glucagon at the glucagon receptor and/or at least 100% or more of the activity of native GLP-1 at the GLP-1 receptor. In some embodiments, the glucagon analog has an EC50 at the GLP-1 receptor which is within 50-fold or less than the EC50 at the glucagon receptor. In some embodiments, the glucagon analog has an EC50 at the GLP-1 receptor which is two- to ten-fold greater than the EC50 at the glucagon receptor. Related conjugates, dimers and multimers, and pharmaceutical compositions, and uses thereof, are further provided.

15 Claims, 12 Drawing Sheets

(56) References Cited

FOREIGN PATENT DOCUMENTS

| | | |
|---|---|---|
| EP | 1695983 B1 | 8/2006 |
| EP | 2036539 A1 | 3/2009 |
| EP | 2036923 A1 | 3/2009 |
| EP | 2398483 | 8/2010 |
| EP | 2300035 | 1/2012 |
| WO | WO96/29342 | 9/1996 |
| WO | WO9707814 | 3/1997 |
| WO | 97/29180 | 8/1997 |
| WO | 98/11126 | 3/1998 |
| WO | 98/19698 | 5/1998 |
| WO | WO 9824464 | 6/1998 |
| WO | WO 9946283 | 9/1999 |
| WO | WO 0020592 | 4/2000 |
| WO | WO00/42026 | 7/2000 |
| WO | WO 0058360 | 10/2000 |
| WO | 01/83527 | 11/2001 |
| WO | WO 0181919 | 11/2001 |
| WO | 01/98331 | 12/2001 |
| WO | WO 0210195 | 2/2002 |
| WO | WO0213801 | 2/2002 |
| WO | 02/48183 | 6/2002 |
| WO | WO 02100390 | 12/2002 |
| WO | WO03/011892 | 2/2003 |
| WO | 03/020201 | 3/2003 |
| WO | WO03022304 | 3/2003 |
| WO | WO 03026635 | 4/2003 |
| WO | 03/035099 | 5/2003 |
| WO | WO 03082898 | 10/2003 |
| WO | 03/103572 | 12/2003 |
| WO | WO 03103697 | 12/2003 |
| WO | WO 03105760 | 12/2003 |
| WO | WO04000354 | 12/2003 |
| WO | 2004/022004 | 3/2004 |
| WO | 2004/067548 | 8/2004 |
| WO | WO 2004078777 | 9/2004 |
| WO | 2004/093823 | 11/2004 |
| WO | 2004/105781 | 12/2004 |
| WO | 2004/105790 | 12/2004 |
| WO | WO 2004103390 | 12/2004 |
| WO | WO 2005082928 | 9/2005 |
| WO | WO 2006086769 | 8/2006 |
| WO | WO 2006121904 | 11/2006 |
| WO | WO2006124529 | 11/2006 |
| WO | WO2006134340 A2 | 12/2006 |
| WO | 2007/022123 | 2/2007 |
| WO | WO 2007028632 | 3/2007 |
| WO | WO2007028633 | 3/2007 |
| WO | 2007/056362 | 5/2007 |
| WO | 2007/100535 | 9/2007 |
| WO | WO 2007109354 | 9/2007 |
| WO | WO 2008021560 | 2/2008 |
| WO | WO 2008022015 | 2/2008 |
| WO | WO2008023050 | 2/2008 |
| WO | WO 2008076933 | 6/2008 |
| WO | 2008/086086 | 7/2008 |
| WO | 2008/101017 | 8/2008 |
| WO | WO2009030738 A1 | 3/2009 |
| WO | WO2009030774 A1 | 3/2009 |
| WO | WO2009034117 A1 | 3/2009 |
| WO | WO2009034118 A1 | 3/2009 |
| WO | WO2009034119 A1 | 3/2009 |
| WO | WO2009035540 A2 | 3/2009 |
| WO | 2009/058662 | 5/2009 |
| WO | 2009/058734 | 5/2009 |
| WO | 2009/095479 | 8/2009 |
| WO | 2009/099763 | 8/2009 |
| WO | 2009/155257 | 12/2009 |
| WO | 2009/155258 | 12/2009 |
| WO | 2010/011439 | 1/2010 |
| WO | 2010/071807 | 6/2010 |
| WO | 2010/080605 | 7/2010 |
| WO | 2010/096052 | 8/2010 |
| WO | 2010/148089 | 12/2010 |
| WO | 2011/075393 | 6/2011 |
| WO | WO 2011087671 | 7/2011 |
| WO | WO 2011087672 | 7/2011 |
| WO | 2011/094337 | 8/2011 |
| WO | WO2011119657 | 9/2011 |
| WO | WO2011143208 | 11/2011 |
| WO | WO2011143209 | 11/2011 |
| WO | WO2011163012 | 12/2011 |
| WO | WO2011163473 | 12/2011 |

OTHER PUBLICATIONS

Ahn, J.M. et al., Development of potent truncated glucagon antagonists, J. Med. Chem., 44(9): 1372-9, Apr. 26, 2001. (Abstract).

Ahn, J.M. et al., A new approach to search for the bioactive conformation of glucagon: positional cyclization scanning, J. Med. Chem., 44(19): 3109-16, Sep. 13, 2001.

Althage et al., JBC "Targeted Ablation of GIP-Producing Cells in Transgenic mice reduces obesity and insulin resistance induced by a high fat diet" 2008).

Andrews et al., "Forming Stable Helical Peptides Using Natural and Artificial Amino Acids", Tetrahedron 55: 11711-11743, (1999).

"Application of Chemical Biotechnology to Optimization of Endocrine Hormones," Carothers Lecture, Mar. 22, 2007.

Azizeh et al., "Pure glucagon antagonists: biological activities and cAMP accumulation using phosphodiesterase inhibitors," Peptides 1997, vol. 18, No. 5, pp. 633-641.

Azizeh et al., "The Role of Phylalanine at Position 6 in Glucagon's Mechanism of Biological Action: Multiple Replacement Analgues of Glucgon," J. Med. Chem., vol. 40, No. 16, 1997, pp. 2555-2562.

Azizeh et al., "Topographical amino acid substitution in position 10 of glucagon leads to antagonists/partial agonists with greater binding differences," J. Med. Chem., vol. 39, No. 13, Jun. 21, 1996, pp. 2449-2455.

Battersby et al., "Diketopiperazine Formation and N-Terminal Degradation in Recombinant Human Growth Hormone", International Journal of Peptide & Protein Research 44: 215-222, (1994).

Biotechnology—A Basis for Better Health & Economic Prosperity, Ohio State University presentation, Aug. 28, 2010.

"Biotechnology—A Basis for Better Health & Economic Prosperity," Indiana University television presentation, Nov. 2010.

Blache et al., "Development of an oxyntomodulin/glicentin C-terminal radioimmunoassay using a "thiol-maleoyl" coupling method for preparing the immunogen," Anal Biochem 1988 173(1):151-159 (1988), abstract only.

Chabenne et al., Optimization of the native glucagon sequence for medicinal purposes, J. Diabetes. Sci. Technol., 4(6): 1322-31, Nov. 1, 2010.

Chia et al., "Exogenous glucose-dependent insulinotropic polypeptide worsens post-prandial hyperglycemia in type 2 diabetes," Diabetes, 58: 1342-1349 (2009).

Collie et al., "Purification and sequence of rat oxyntomodulin," Proc. Natl. Acad. Sci. USA, vol. 91, pp. 9362-9366, Sep. 1994.

DatabaseEMBL, Jul. 16, 2007, Richard DiMarchi and David Smiley, "Human Glucagon Peptide SEQ ID No. 1," XP002631582, retrieved from EBI, Database Accession No. AGB07042, Abstract.

Jonathan Day et al., "A New Glucagon and GLP-1 Co-Agonist Eliminates Obesity in Rodents," Nature Chemical Biology, vol. 5, No. 10, Oct. 2009, pp. 749-757.

Day et al., Charge inversion at position 68 of the glucagon and glucagon-like peptide-1 receptors supports selectivity in hormone action. J. Pept. Sci., 17(3): 218-25, Nov. 30, 2010.

Day, J.; Patterson, J.; Gelfanov, V. and DiMarchi, Richard Molecular-basis for Specificity in Biological Action at the Homologous Glucagon and GLP-1 Receptors, (2009) Proceedings of the 21st American Peptide Society 142-143.

De, Design of peptide-based prodrug chemistry and its application to glucagon-like peptide 1. Masters Thesis Aug. 2007. [Retrieved from the Internet on Jun. 16, 2009: <https://scholarworksiu.edu/dspace/browse?value=De%2C+ArnabBtype=author>]; p. 8, para 2; p. 16, para 3; p. 40, para 1; p. 66, para 2; p. 77, para 1-2; p. 79, para 1.

De, Arnab; DiMarchi, Richard D. Investigation of the feasibily of an amide-based prodrug under physiological conditions. International Journal of Peptide Research and Therapeutics (2008), 14(4), 393.

(56) References Cited

OTHER PUBLICATIONS

De, et al., "Investigation of the feasibily of an amide-based prodrug under physiological conditions," Int. J. Pept. Res. Ther., 14, pp. 255-262 (2008).
De, A. and DiMarchi, R. Synthesis & Analysis of Peptide Hormone-based prodrugs, (2009) Proceedings of the 21st American Peptide Society 160-161.
De, A. and DiMarchi, R. Synthesis & Characterization of Ester-Based Prodrugs of Glucagon-Like Peptide 1, Peptide Science (2010) 94(4) 448-456.
DiMarchi, "Peptides—Development of Prodrug Chemistry," RBF Symposium Feb. 1-4, 2011 India.
DiMarchi, Richard, "The Use of Bioproducts in the Treatments of Metabolic Diseases" presentation slides for the Keystone Symposia (Jan. 25, 2009, Banff, Alberta).
Drucker, "Glucagon Gene Expression in Vertebrate Brain," The Journal of Biological Chemistry, vol. 263, No. 27, pp. 13475-13478, 1988.
Drucker, "The biology of incretin hormones," Cell Metabolism 3:153-165 (2006).
"Emergence of Chemical Biotechnology," Eli Lilly and Co. presentation, Jun. 22, 2009.
"The Emergence of Chemical Biotechnology & Its Application to Optimization of Endocrine Hormones," UMBC presentation, Mar. 26, 2008.
Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).
Evans et al., "Effect of β-Endorphin C-Terminal Peptides on Glucose Uptake in Isolated Skeletal Muscles of the Mouse," Peptides, vol. 18, No. 1, pp. 165-167, (1997).
Extended EP Search Report completed by the EP Searching Authority on Apr. 6, 2011 in connection with EP Patent Application No. 08845852.6.
Marita P. Feldkaemper et al., "Localization and Regulation of Glucagon Receptors in the Chick Eye and Preproglucagon and Glucagon Receptor Expression in the Mouse Eye," Experimental Eye Research, Academic Press Ltd., London, vol. 79, No. 3, Sep. 1, 2004, pp. 321-329.
Finan, B.; Gelfanov, V. and DiMarchi, R. Assessment of a Tat-Derived Peptide as a Vector for Hormonal Transport, (2009) Proceedings of the 21st American Peptide Society 321-322.
Garcia-Aparicio et al., "Design and Discovery of a Novel Dipeptidyl-peptidase IV (CD26)-Based Prodrug Approach", *J. Med. Chem.* 49: 5339-5351 (2006).
Gelfanov, et al., Discover and Structural Optimization of High Affinity Co-Agonists at the Glucagon and GLP-1 Receptors, Understanding Biology Using Peptides, Springer, pp. 763-764, Jun. 23, 2005.
GenBank entry AAH05278. Jul. 15, 2006. [Retrieved from the Internet Jun. 18, 2009: ~http://www._ncbi._nim.n_ih.gov/protein/13528972>].
Goolcharran et al., "Comparison of the Rates of Deamidation, Diketopiperazine Formation, and Oxidation in Recombinant Human Vascular Endothelial Growth Factor and Model Peptides", *AAPS Pharmsci 2000* 2(1) article 5: 1-6 (Mar. 17, 2000).
Gysin et al., "Design and Synthesis of Glucagon Partial Agonists and Antagonists," Biochemistry, 25, (1986), pp. 8278-8284.
Habegger et al., The metabolic actions of glucagon revisited, *Nat. Rev. Endocrinol.*, 6(12): 689-97, Oct. 19, 2010.
Habi, "Special Issue: Program and Abstracts for the 19th American Peptide Symposium, 2005, Abstracts of Poster Section C," (pp. 574-603) Article first published online: Jun. 10, 2005 |DOI: 10.1002/bip.20325.
Hansen et al., "Incretin hormones and insulin sensitivity," Trends in Endocrinology and Metabolism, vol. 16, No. 4, May/Jun. 2005, pp. 135-136.
Harris, J. Milton, Final Word: PEGylation—A "Sunset" Technology? <http://licence.icopyright.net/user/viewFreeUse.act?fuid=OTU1NjY3OA%3D%3D>, BioPharm International, Jun. 1, 2004.
Heppner et al., Glucagon regulation of energy metabolism, *Physiol Behav.*, 100(5): 545-8, Apr. 8, 2010.
Hjorth et al., "glucagon and Glucagon-like Peptide 1: Selective Receptor Recognition via Distinct Peptide Epitopes," The Journal of Biological Chemistry, vol. 269, No. 48, pp. 30121-30124, Dec. 2, 1994.
Hruby et al., "The Design and Biological Activities of Glucagon Agonists and Antagonists, and Their Use in Examining the Mechanisms of Glucose Action," *Curr. Med. Chem.-Imm., Endoc. & Metab. Agents*, 2001, 1, pp. 199-215.
Supplemental European Search Report issued in connection with EP Application No. 09800752 issued on Jun. 20, 2011.
Irwin et al., "Early administration of the glucose-dependent insulinotropic polypeptide receptor antagonist ($Pro^3$) GIP prevents the development of diabetes and related metabolic abnormalities associated with genetically inherited obesity in *ob/ob* mice," Diabetologia 50:1532-1540 (2007).
Joshi et al., "The Estimation of Glutaminyl Deamidation and Aspartyl Cleavage Rates in Glucagon," *International Journal of Pharmaceutics*, 273 (2004), pp. 213-219.
Joshi et al., "The Degradation Pathways of Glucagon in Acidic Solutions," *International Journal of Pharmaceutics*, 203 (2000), pp. 115-125.
Joshi et al, "Studies on the Mechanism of Aspartic Acid Cleavage and Glutamine Deamidation in the Acidic Degradation of Glucagon," *Journal of Pharmaceutical Sciences*, vol. 94, No. 9, Sep. 2005, pp. 1912-1927.
Krstenansky et al., "Importance of the C-terminal α-helical structure for glucagon's biological activity," Int. J. Peptide Protein Res., 32, 1988, 468-475.
Kukuch, A.; Patterson, J.; DiMarchi, R. and Tolbert, T. Immunoglobulin Fc-based Peptide Fusion Proteins as a Basis for Optimizing In Vivo Pharmacology, (2009) Proceedings of the 21st American Peptide Society 177-178.
Kulkarni, "GIP: No Longer the Neglected Incretin Twin?," Science Translational Medicine 2(49): p. 47, Sep. 15, 2010.
Lebl, Michal, "Peptides: Breaking Away: The Proceedings of the Twenty-First American Peptide Symposium", *Prompt Scientific Publishing* (2009).
Lee et al., "Synthesis, Characterization, and Pharmacokinetic Studies of PEGylated Glucagon-like Peptide-1," *Bioconjugate Chem.*, 2005, vol. 16, No. 2, pp. 377-382.
"Legacy Products—'Back to the Future'," presentation to Eli Lilly and Co., Sep. 22, 2005.
Levy et al., Optimization of the C-terminal Sequence in Glucagon to Maximize Receptor Affinity, *Understanding Biology Using Peptides*, American Peptide Society, Apr. 2006.
Levy et al., Optimization of the C-terminal Sequence in Glucagon to Maximize Receptor Affinity, Poster Presentation, Jun. 19, 2005.
Li et al., Crystallization and preliminary X-ray analysis of anti-obesity peptide hormone oxyntomodulin, *Protein & Peptide Letters*, 15(2): 232-4 (2008).
Li et al., Design, synthesis and crystallization of a novel glucagon analog as a therapeutic agent, *Acta Crystallogr. Sect. F Struct. Biol. Cryst. Commun.*, 63(Pt 7):599-601, Jun. 15, 2007.
Li et al., Structural Basis for Enhanced Solublity of a C-Terminally Extended Glucagon Analog, *Biopolymers.*, 96(4): 480 (2011).
Ma, T.; Day, J.; Gelfanov, V. and DiMarchi, R. Discovery and Structural Optimization of High Affinity Co-Agonists at the Glucagon and GLP-1 Receptors, (2009) Proceedings of the 21st American Peptide Society 146-147.
Madsen et al., "Structure—Activity and Protraction Relationship of Long-Acting Glucagon-like Peptide-1 Derivatives: Importance of Fatty acid Length, Polarity, and Bulkiness," J. Med. Chem. 2007, 50, pp. 6126-6132.
McKEE et al., Receptor Binding and Adenylate Cyclase Activities of Glucagon Analogues Modified in the N-Terminal Region, Biochemistry, 25: 1650-6 (1986).
"Molecular Miracles," Indiana University, Apr. 13, 2011.
Montrose-Rafizadeh et al., "High Potency Antagonists of the Pancreatic Glucagon-like Peptide-1 Receptor," Journal of Biological Chemistry, 272(34) 21201-21206 (1997).

(56) References Cited

OTHER PUBLICATIONS

Murphy, et al., "Potent Long-Acting Alkylated Analogs of Growth Hormone-Releasing Factor," Pept. Res., vol. 1. No. 1, pp. 36-41 (1988).

Nogueiras et al., Direct control of peripheral lipid deposition by CNS GLP-1 receptor signaling is mediated by the sympathetic nervous system and blunted in diet-induced obesity, J. Neurosci., 29(18): 5916-25, May 6, 2009.

"Novel Glucagon Peptides That Demonstrate the Virtues of Combinatorial Pharmacology," University of Toledo, Mar. 22, 2012.

"Novel Glucagon-Based Peptides—Virtues of Combinatorial Pharmacology," Aug. 31, 2011, Berlin.

"Novel Glucagon-Based Peptides—Virtues of Combinatorial Pharmacology," European Peptide Symposium, Sep. 5-9, 2010, Copenhagen, Denmark.

"Novel Glucagon-Based Peptides—Virtues of Combinatorial Pharmacology," University of Michigan, Oct. 13, 2010.

"Novel Glucagon-Based Peptides—Virtues of Combinatorial Pharmacology," Yale University, May 13, 2011.

"Novel Glucagon-Like Chimera Peptides—Virtues of Combinatorial Pharmacology," AAPS May 2010.

"Novel Glucagon-Like Chimera Peptides—Virtues of Combinatorial Pharmacology," Keystone Conference, Apr. 12-17, 2010, Whistler, B.C.

"Novel Glucagon-Like Chimera Peptides—Virtues of Combinatorial Pharmacology," University of Cincinnati, Jun. 2010.

O'Brien, Assay for DPPIV Activity using Homogenous, Luminescent Method, Cell Notes 2005, 11:8-11.

Ouyang et al., Discovery of Bi-Functional Peptides Balanced in Glucagon Antagonism & GLP-1 Agonism. A Search for the Molecular Basis in the Inversion of Activity at Homologous Receptors, 71st Scientific sessions of American Diabetes Association 2011—Post-Conference Review and Analysis.

Ouyang et al., "Synthesis and Characterization of Peptides with Glucagon Antagonism and GLP-1 Agonism," poster presentation at the $21_{st}$ American Peptide Symposium (Jun. 7-12, 2009, Bloomington, IN).

Pan et al., Design of a Long Acting Peptide Functioning as Both a Glucagon-like Peptide-1 Receptor Agonist and a Glucagon Receptor Agonist, J. Biol. Chem., 281(18): 12506-15, Table 1, May 5, 2006.

Pan et al., "Synthesis of Cetuximab-Immunoliposomes via a Cholesterol-Based Membrane Anchor for Targeting of EGFR," Bioconjugate Chem., 18, pp. 101-108, 2007.

Patterson et al., A novel human-based receptor antagonist of sustained action reveals body weight control by endogenous GLP-1, ACS Chem Biol., 6(2): 135-45 Nov. 4, 2010.

Patterson et al., Functional association of the N-terminal residues with the central region in glucagon-related peptides, J. Peptide Sci., First published online Jun. 10, 2011.

PCT International Search Report for PCT/US2008/050099 completed by the US Searching Authority on Sep. 1, 2008.

PCT International Search Report for PCT/US2008/053857 completed by the US Searching Authority on Sep. 16, 2008.

PCT International Search Report for PCT/US2011/041601 completed by the US Searching Authority on Nov. 10, 2011.

PCT International Search Report for PCT/US2008/081333 completed by the US Searching Authority on Mar. 12, 2009.

PCT International Search Report for PCT/US2006/043334 completed by the US Searching Authority on Apr. 23, 2009.

PCT International Search Report for PCT/US2008/080973 completed by the US Searching Authority on Jun. 6, 2009.

PCT International Search Report for PCT/US2009/031593 completed by the US Searching Authority on Jun. 18, 2009.

PCT International Search Report for PCT/US2009/034448 completed by the US Searching Authority on Jun. 4, 2010.

PCT International Search Report for PCT/US2009/047437 completed by the US Searching Authority on Nov. 3, 2009.

PCT International Search Report for PCT/US2009/047447 completed by the US Searching Authority on Mar. 19, 2010.

PCT International Search Report for PCT/US2009/068678 completed by the US Searching Authority on May 5, 2010.

PCT International Search Report for PCT/US2010/038825 completed by the US Searching Authority on Sep. 15, 2010.

PCT International Search Report for PCT/US2010/059724 completed by the US Searching Authority on Jun. 14, 2011.

"Novel Glucagon-Based Peptides—Virtues of Combinatorial Pharmacology," Peptides Therapeutics Symposium, Oct. 21-22, 2010, La Jolla, California.

"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.

Perret et al., "Mutational analysis of the glucagon receptor: similarities with the vasoactive intestinal peptide (VIP)/pituitary adenylate cyclase-activating peptide (PACAP)/secretin receptors for recognition of the ligand's third residue," J. Biochem., 362 (2002), pp. 389-394.

Phillips et al., "Supramolecular Protein Engineering: Design of Zinc-Stapled Insulin Hexamers as a Long Acting Depot," J. Biol. Chem., vol. 285, No. 16, Apr. 16, 2010, pp. 11755-11759.

Robberecht, P. et al., "Receptor Occupancy and Adenylate Cyclase Activation in Rat Liver and Heart Membranes by 10 Glucagon Analogs Modified in Position 2, 3, 4, 25, 27 and/or 29," Regulatory Peptides, 21 (1988), 117-128.

M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.

Santos et al., Cyclization-Activated Prodrugs. Synthesis, Reactivity and Toxicity of Dipeptide Esters of Paracetamol, Bioorganic & Medicinal Chemistry Letters 15: 1595-1598 (2005).

Sapse et al., The Role of Sale Bridge Formation in Glucagon: An Experimental and Theoretical Study of Glucagon Analogs and Peptide Fragments of Glucagon, Molec. Med., 8(5): 251-62, May 1, 2002.

Sato, H., "Enzymatic procedure for site-specific pegylation of proteins," Advanced Drug Delivery Reviews 54, pp. 487-504 (2002).

Schafmeister et al., "An All-Hydrocarbon Cross-Linking System for Enhancing the Helicity and Metaboli Stability of Peptides", J. Am. Chem. Soc. 122: 5891-5892 (2000).

"Speaking From the Gut: From Gastrointestinal Hormones to Combinatorial Therapies," Presentation to American Diabetes Association, Jun. 25, 2011.

Stigsnaes et al., "Characterisation and Physical Stability of PEGylated Glucagon," International Journal of Pharmaceutics, 330 (2007), pp. 87-98.

Sturm et al., "Structure-Function Studies on Positions 17, 18, and 21 Replacement Analogues of Glucagon: The Importance of Charged Residues and Salt Bridges in Glucagon Biological Activity," J Med Chem 1998, 41, 2693-2700.

Sueiras-Diaz et al., "Structure-Activity Studies on the N-Terminal Region of Glucagon," J. Med. Chem., 27, pp. 310-315, 1984.

Supplemental European Search Report issued in connection with EP Application No. 09767567.2 issued on Jun. 17, 2011.

"The Pursuit of Transformational Medicines," Keystone presentation, Jan. 29-Feb. 3, 2012, Santa Fe, NM.

"The Pursuit of Transformational Medicines," presentation to American Peptide Symposium, Jun. 25-30, 2011, San Diego, CA.

"The Pursuit of Transformational Medicines," NP2D presentation, Dec. 4, 2011.

Traylor et al., Identification of the High Potency Glucagon Agonist with Enhanced Biophysical Stability and Aqueous Solubility, Poster Abstract PY 10, pp. 505-506, Jun. 10, 2005.

Trivedi, D. et al., Design and synthesis of conformationally constrained glucagon analogues, J. Med. Chem., 43(9): 1714-22, May 4, 2000 (Abstract).

Tschoep et al., A Novel Glucagon/GLP-1 Co-Agonist Eliminates Obesity in Rodents, Diabetes, 58 (Supp. 1): A83 (2009).

Tschoep, Matthias, "A Novel Glucagon/GLP-1 Co-Agonist Eliminates Obesity in Rodents" presentation slides for the 2009 American Diabetes Association meeting (Jun. 5-9, 2009, New Orleans, LA).

Tschoep et al., "A Novel Glucagon/GLP-1 Co-Agonist Eliminates Obesity in Rodents," American Diabetes Association Abstract No. 313-OR (2009).

(56) References Cited

OTHER PUBLICATIONS

Tschoep, Matthias, "Afferent Gut Hormones in the Control of Energy Balance and Metabolism" presentation slides for the 21st American Peptide Symposium (Jun. 7-12, 2009, Bloomington, IN).

Tschoep, "CNS Integration of Systems Metabolism: Target Opportunities for Diabetes Prevention and Therapy," RBF Symposium Feb. 1-4, 2011 India.

"Two for the Money Gut Hormone Hybrids," Tschoep, ADA meeting, Jun. 25-29, 2010, Orlando, FL.

Unson et al., "Glucagon antagonists: Contribution to binding and activity of the amino-terminal sequence 1-5, position 12 and the putative alpha-helical segment 19-27," J. Biol. Chem. v264, pp. 789-794, Jan. 15, 1989, p. 792, para 1, Table 1.

Unson et al., Positively Charged Residues at Positions 12, 17, and 18 of Glucagon Ensure Maximum Biological Potency, *J. Biol. Chem.*, 273(17): 10308-12 (1998).

Unson et al., "Role of Histidine-1 in Glucagon Action," Archives of Biochemistry and Biophysics, vol. 300, No. 2, pp. 747-750, Feb. 1, 1993.

Vijayalakshmi et al., "Comparison of Helix-Stabilizing Effects of α, α-dialkyl Glycines with Linear and Cycloalkyl Side Chains", *Biopolymers* 53: 84-98 (Jan. 21, 2000).

Walensky et al., "Activation of Apoptosis in Vivo by a Hydrocarbon-Stapled BH3 Helix", *Science* 205: 1466-1470 (Sep. 3, 2004).

Ward, B.; Finan, B.; Gelfanov, V. and DiMarchi, R. Exploring the N-terminal Hydrophobic Faces of Glucagon and Glucagon-like Peptide-1, (2009) Proceedings of the 21st American Peptide Society 153-154.

Ward, "Fatty Acid Acylation of Peptides: Developing strategies to enhance medicines for treating metabolic disorders," Jan. 14, 2009.

Ward et al., In vitro and in vivo evaluation of native glucagon and glucagon analog (MAR-D28) during aging: lack of cytotoxicity and preservation of hyperglycemic effect, J. Diabetes Sci. Technol., 4(6):1311-21, Nov. 1, 2010.

Wibowo, Synthesis, Purification , and Biological Activity of AIB Substituted Glucagon and GLP-1 Peptide Analogues (2005-2006) vol. 45, 707=738, accessed https://scholarworks.iu.edu/dspee/handle/2022/326 on Jul. 17, 2012.

Wynne et al., "Subcutaneous Oxyntomodulin Reduces Body Weight in Overweight and Obese Subjects," *Diabetes*, vol. 54, Aug. 2005, pp. 2390-2395.

Yang, B. and DiMarchi, R.D. (2005). A Novel Approach to Resin-based Cysteine Alkylation Peptides: Chemistry, Structure and Biology, Proceedings of the XIX American Peptide Symposium, (88-89).

Yang et al., "A Novel Approach to Resin-Based Cysteine Alkylation," American Peptide Society, 2005.

Yang et al., "A Novel Approach to Resin-Based Cysteine Alkylation," poster presentation to American Peptide Society, 2005.

Yang et al., Synthesis and Biological Assessment of Sulfonic Acid-Based Glucagon Antagonists, Understanding Biology Using Peptides, American Peptide Symposia, 9(Part 6): 305-6 (2006).

Yang et al., "Synthesis and Biological Assessment of Sulfonic Acid-Based Glucagon Antagonists," American Peptide Society, 2005.

Yang et al., "Synthesis and Biological Assessment of Sulfonic Acid-Based Glucagon Antagonists," poster presentation to American Peptide Society, 2005.

Zhang et al., Design and synthesis of novel GLP1 analogues with significantly prolonged time action, Biopolymers., 80(4): 555 (2005).

FIGURE 1

| SEQ ID NO: | # | | | | | | |
|---|---|---|---|---|---|---|---|
| SEQ ID NO: 2 | 1 | | HSQGT | FTSDY | SKYLD | SRRAQ | DFVQW | LMNT |
| SEQ ID NO: 18 | 2 | | HSQGT | FTSDY | SKYLD | SKRAQ | DFVQW | LMNT-NH₂ |
| SEQ ID NO: 19 | 3 | | HSQGT | FTSDY | SKYLD | SKRAQ | EFVQW | LMNT-NH₂ |
| SEQ ID NO: 20 | 4 | | HSQGT | FTSDY | SKYLD | SKRAE | EFVQW | LMNT-NH₂ |
| SEQ ID NO: 21 | 5 | | HSQGT | FTSDY | SKYLD | KRRAE | DFVQW | LMNT-OH |
| SEQ ID NO: 22 | 6 | | HSQGT | FTSDY | SKYLD | ERRAQ | DFVQW | LMNT-OH |
| SEQ ID NO: 23 | 7 | | HSQGT | FTSDY | SKYLD | ERRAX | DFVQW | LMNT-OH |
| SEQ ID NO: 24 | 8 | | HSQGT | FTSDY | SKYLD | ERRAQ (G) | DFVQW | LMNT-OH |
| SEQ ID NO: 25 | 9 | | HSQGT | FTSDY | SKYLD | ERRAQ | DFVQW | LMNT-NH₂ |
| SEQ ID NO: 26 | 10 | | HSQGT | FTSDY | SKYLD | DRRAQ | DFVQW | LMNT-OH |
| SEQ ID NO: 27 | 11 | | HSQGT | FTSDY | SKYLD | SDRAQ | DFVQW | LMNT-OH |
| SEQ ID NO: 28 | 12 | -10 KA | HSQGT | FTSDY | SKYLD | SDRAQ | DFVQW | LMNT-NH₂ |
| SEQ ID NO: 29 | 13 | KA | HSEGT | FTSDY | SKYLD | SERAQ | DFVQW | LMNT-NH₂ |
| SEQ ID NO: 30 | 14 | k | HSQeT | FTSDY | SKYLD | SRRAQ | DFVQW | LMNT-NH₂ |
| SEQ ID NO: 31 | 15 | k | HSQeT | FTSDY | SKYLD | SRRAQ | DFVQW | LMNT-NH₂ |
| SEQ ID NO: 32 | 16 | | HSQKT | FTSDY | SKYLD | SRRAQ | DFVQW | LMNT-NH₂ |
| SEQ ID NO: 33 | 17 | | HSQGT | FTEDY | SKYLD | SRRAQ | DFVQW | LMNT-NH₂ |
| SEQ ID NO: 34 | 18 | | HSQGT | FTEDY | SKYLD | SRRAQ | DFVQW | LMNT-NH₂ |
| SEQ ID NO: 35 | 19 | | HSQGT | FTEDY | SKYLD | SRRAQ | DFVQW | LMNT-NH₂ |

X=Dab,   e & k = d-isomers

FIGURE 2

| SEQ ID NO: | Glucagon Analog# | Sequence |
|---|---|---|
| 37 | 20 | HserQGTFTSDY SKYLD E KRAKEFVQWLMNT amide |
| 38 | 21 | HserQGTFTSDY SKYLDAibKRAKEFVQWLMNT amide |
| 39 | 22 | HserQGTFTSDK(γE-C16)SKYLDAibKRAKEFVQWLMNT amide |
| 40 | 23 | DmiaSQGTFTSDY SKYLD E RRAKDFVCWLMNT amide |
| 41 | 24 | HserQGTFTSDY SKYLD E KRAKEFVCWLMNT amide |
| 42 | 25 | HAibQGTFTSDY SKYLD E KRAKEFVCWLMNT amide |
| 43 | 26 | HserQGTFTSDY SKYLDAibKRAKEFVCWLMNT amide |
| 44 | 27 | HAibQGTFTSDY SKYLDAibKRAKEFVCWLMNT amide |
| 45 | 28 | DmiaSQGTFTSDY SKYLDAibKRAKEFVCWLMNT amide |

FIGURE 3

| SEQ ID NO | Analog # | Sequence |
|---|---|---|
| 75 | 60 | HserQGTFTSDYSKYLDAibKRAKEFVCWLLDGGPSSGAPPPS amide |
| 76 | 61 | HserQGTFTSDYSKYLD E KRAKEFVCWLLDGGPSSGAPPPS amide |
| 77 | 62 | HserQGTFTSDK(γE-C₁₆) SKYLDAibKRAKEFVCWLLDT-amide |
| 78 | 63 | HserQGTFTSDK(γEγE-C₁₆) SKYLDAibKRAKEFVCWLLDT-amide |
| 79 | 64 | HAibQGTFTSDYSKYLDAibKAAKEFVCWLLDT amide |
| 80 | 65 | HSQGTFTSDY SKYLD E KRAKEFVQWLMNT amide |
| 81 | 66 | HSQGTFTSDYSKYLDSKRAQEFVQWLMNT amide |
| 82 | 67 | HSQGTFTSDYSKYLDERRAKDFVQWLMNT amide |
| 83 | 68 | HSQGTFTSDYSKYLDERRAKEFVQWLMNT amide |

FIGURE 4A

| SEQ ID NO | Glucagon Analog# | Sequence |
|---|---|---|
| 58 | 42 | HAibQGTFTSDK(γEγE-C16)SKYLDAibRAAQDFVQWLMDT-amide |
| 59 | 43 | HAibQGTFTSDK(γE-C16) SKYLDAibRAAQDFVQWLMDT-amide |
| 60 | 44 | HserQGTFTSDK(γEγE-C16)SKYLDAibRAAQDFVQWLMDT-amide |
| 61 | 45 | HAibEGTFTSDK(γEγE-C16)SKYLDAibRAAQDFVQWLMDT-amide |
| 62 | 46 | HAibQGTFISDK(γEγE-C16) SKYLDAibRAAQDFVQWLMDT acid |
| 63 | 48 | HAibQGTFTSDK(γEγE-C16)SKYLEAibRAAQDFVQWLMDT-amide |
| 64 | 49 | HAibQGTFTSDK(γEγE-C16)SKYLDE RAAQDFVQWLMDT-amide |
| 65 | 50 | HAibQGTFTSDK(γE-C16) SKYLDE RAAQDFVQWLMDT-amide |
| 66 | 51 | HserQGTFTSDK(γE-C16) SKYLDE RAAQDFVQWLLDT-amide |
| 67 | 52 | HAibQGTFTSDK(γE-C16) SKYLDE QAAKEFIAWLLDT-amide |

FIGURE 4B

| SEQ ID NO | Glucagon Analog# | Sequence |
|---|---|---|
| 84 | 69 | HAibQGTFTSDK(C16) SKYLDAibRAAQDFVQWLMDT-amide |
| 85 | 70 | HAibQGTFTSDK(γEγE-C14)SKYLDAibRAAQDFVQWLMDT-amide |
| 86 | 71 | HAibQGTFTSDK(γEγE-C18)SKYLDAibRAAQDFVQWLMDT-amide |
| 89 | 76 | HserQGTFTSDK(γE-C16)SKYLDEQAAKEFICWLLDT-acid |
| 90 | 77 | HserQGTFTSDK(γE-C16)SKYLDEQAAKEFICWLLDT-amide |
| 91 | 78 | HserQGTFTSDK(γE-C16)SKYLDEQAAKEFICWLLDTGG-acid |
| 92 | 79 | HserQGTFTSDK(γE-C16)SKYLDERAAQDFVCWLLDT-acid |
| 93 | 80 | HAibQGTFTSDK(γE-C16)SKYLDERAAQDFVCWLLDT-amide |
| 94 | 81 | HalaQGTFTSDK(γE-C16)SKYLDERAAQDFVCWLLDT-amide |
| 95 | 82 | HserQGTFTSDK(γE-C16)SKYLDEQAAKEFICWLLDE-amide |
| 96 | 83 | HserQGTFTSDK(γE-C16)SKYLDEQAAKEFICWLLDTE-amide |

FIGURE 5

| SEQ ID NO | Glucagon Analog# | Sequence |
|---|---|---|
| 47 | 30 | HAibQGTFTSDK(γE-C16)SKYLDEQAAKEFIC(PEG40K-TE)WLLDT-amide |
| 68 | 53 | HserQGTFTSDK(γE-C16)SKYLDEQAAKEFIC      WLLDT-amide |
| 69 | 54 | DmiaSQGTFTSDK(γE-C16)SKYLDEQAAKEFIC      WLLDT-amide |
| 88 | 75 | desAminoHSQGTFTSDK(γE-C16)SKYLDEQAAKEFIC      WLLDT-amide |
| 70 | 57 | AcHSQGTFTSDK(γE-C16)SKYLDEQAAKEFIC      WLLDT-amide |
| 119 | 79' | HserQGTFTSDK(γE-C16)SKYLDEQAAKEFICWLLDT-acid |
| 95 | 88 | HserQGTFTSDK(γE-C16)SKYLDEQAAKEFICWLLDE-amide |
| 71 | 55 | HserQGTFTSDK(γE-C16)SKYLDEQAAKEFICWLLDT-acid |
| 120 | 83' | HserQGTFTSDK(γE-C16)SKYLDEQAAKEFICWLLDTE-amide |
| 72 | 56 | HserQGTFTSDK(γE-C16)SKYLDEQAAKEFICWLLDTGG-acid |

FIGURE 6

| | | |
|---|---|---|
| SEQ ID NO: 73 | 58 | HAibQGTFTSDK(γE-C16)SKYLDERAAQDFVCWLLDT-amide |
| SEQ ID NO: 74 | 59 | HalaQGTFTSDK(γE-C16)SKYLDERAAQDFVCWLLDT-amide |
| SEQ ID NO: 66 | 51 | HserQGTFTSDK(γE-C16)SKYLDERAAQDFVQWLLDT-amide |
| SEQ ID NO: 46 | 29 | HserQGTFTSDK(γE-C16)SKYLDERAAQDFVC(PEG40K-TE)WLLDT-amide |

FIGURE 8A

| SEQ ID NO | Glucagon Analog# | Sequence |
|---|---|---|
| 46 | 29 | HserQGTFTSDK(B)SKYLDERAAQDFV(C)WLLDT-amide |
| 47 | 30 | HAibQGTFTSDK(B)SKYLDEQAAKEFI(C)WLLDT-amide |
| 48 | 31 | HserQGTFTSDY–SKYLDEEAVRLFI-E-WLMNT-amide |
| 49 | 32 | HAibQGTFTSDY–SKYLDEEAVRLFI-E-WLMNT-amide |
| 50 | 33 | HserQGTFTSDY–SKYLDEEAVRLFI-C-WLMNT-amide |
| 51 | 34 | HAibQGTFTSDY–SKYLDEEAVRLFI-C-WLMNT-amide |
| 52 | 35 | HserQGTFTSDY–SKYLDEEAVRLFI(C)WLMNT-amide |
| 53 | 36 | HAibQGTFTSDY–SKYLDEEAVRLFI(C)WLMNT-amide |

FIGURE 8B

| SEQ ID NO | Glucagon Analog # | Sequence |
|---|---|---|
| 37 | 20 | HserQGTFTSDY - SKYLD E KRAKEFVQWLMNT amide |
| 38 | 21 | HserQGTFTSDY - SKYLDAibKRAKEFVQWLMNT amide |
| 54 | 37 | H S QGTFTSDK(B)SKYLD E EAVRLFIEWLMNT amide |
| 55 | 38 | HAibQGTFTSDK(B)SKYLD E EAVRLFIEWLMNT amide |
| 56 | 39 | H S QGTFTSDK(D)SKYLD E EAVRLFIEWLMNT amide |
| 57 | 40 | HAibQGTFTSDK(D)SKYLD E EAVRLFIEWLMNT amide |

FIGURE 8C

| SEQ ID NO | Glucagon Analog # | Sequence |
|---|---|---|
| 97 | 84 | HserQGTFTSDY............SKYLDEQAVRLFICWLLDG-Cex |
| 98 | 85 | HserQGTFTSDK(γE-C$_{16}$) SKYLD E QAVRLFICWLLDT-amide |
| 99 | 86 | HserQGTFTSDYSKYLDAibKAVRLFICWLLDT-amide |
| 100 | 87 | HserQGTFTSDYSKYLD E QAVRLFICWLLDT-amide |

FIGURE 9

| SEQ ID NO | Glucagon Analog | Sequence |
|---|---|---|
| 102 | 89 | HsQGTFTSDYSLYLDEQAAKEFICWLLDT-amide E16-K20 lactam |
| 103 | 90 | HsQGTFTSDYSKYLDERAAKDFVCWLLDT-amide E16-K20 lactam |
| 104 | 91 | HsQGTFTSDYSLYLDERAAKDFVC(TE-40KPEG)WLLDT-amide E16-K20 lactam |
| 105 | 92 | HsQGTFTSDYSKYLDEQAAKEFIC(TE-40KPEG)WLLDT-amide E16-K20 lactam |
| 106 | 93 | HsQGTFTSDYSKYLDAibKRAKEFVC(TE-40KPEG)WLLDGGPSSGAPPPS-amide |
| 107 | 94 | HsQGTFTSDYSKYLDEKRAKEFVCWLLDGGPSSGAPPPS-amide |
| 108 | 95 | H ser QGTFTSDK(γEC16)SKYLDEQAAKEFI C*(40K-TE) WLLDE |
| 109 | 96 | H ser QGTFTSDK(γEC16)SKYLDEQAAKEFI C*(40K-TE) WLLDTE amide |
| 110 | 97 | H ser QGTFTSDK(rEC16)SKYLDaibKRAKE FV C*(40K-TE) WLLDT amide |
| 111 | 98 | H aib QGTFTSDYSKYLDaibKAAKEFV C*(40K-TE) WLLDT amide |
| 112 | 99 | H ser QGTFTSDYSKYLDaibKAVRLFI C*(40K-TE) WLLDT amide |
| 113 | 100 | H ser QGTFTSDYSKYLDEQAVRLFI C*(40K-TE) WLLDT amide |

GLUCAGON/GLP-1 RECEPTOR CO-AGONISTS

CROSS REFERENCE TO RELATED APPLICATIONS

This application is a U.S. national counterpart application of international application serial No. PCT/US2010/059724 filed Dec. 9, 2010, which claims priority to U.S. Provisional Patent Application No. 61/288,248 filed Dec. 18, 2009. The entire disclosures of PCT/US2010/059724 and U.S.S.N 61/288,248 are hereby incorporated by reference.

Incorporated by reference in its entirety is a computer-readable nucleotide/amino acid sequence listing submitted concurrently herewith and identified as follows: One 122 KB ACII (Text) file named "45098_ST25.txt," created on Dec. 18, 2009.

BACKGROUND

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1(7-36) amide or GLP-1(7-37) acid are biologically potent forms of GLP-1, that demonstrate essentially equivalent activity at the GLP-1 receptor.

During hypoglycemia, when blood glucose levels drop below normal, glucagon signals the liver to break down glycogen and release glucose, causing blood glucose levels to rise toward a normal level. Hypoglycemia is a common side effect of insulin therapy in patients with hyperglycemia (elevated blood glucose levels) due to diabetes. Thus, glucagon's most recognized role in glucose regulation is to counteract the action of insulin and maintain blood glucose levels.

GLP-1 has different biological activities compared to glucagon. Its actions include stimulation of insulin synthesis and secretion, inhibition of glucagon secretion, and inhibition of food intake. GLP-1 has been shown to reduce hyperglycemia in diabetics. Exendin-4, a peptide from lizard venom that shares about 50% amino acid identity with GLP-1, activates the GLP-1 receptor and likewise has been shown to reduce hyperglycemia in diabetics.

There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

BRIEF SUMMARY OF THE INVENTION

Provided herein are glucagon analogs of native human glucagon (SEQ ID NO: 2) that exhibit activity at the glucagon receptor, activity at the GLP-1 receptor, or activity at each of the glucagon receptor and the GLP-1 receptor.

The glucagon analogs described herein comprise an amino acid sequence which is based on the amino acid sequence of native human glucagon (SEQ ID NO: 2). In some aspects, the glucagon analogs described herein comprise a modified amino acid sequence of SEQ ID NO: 2 comprising 1, 2, 3, 4, 5, 6, 7, 8, 9, 10, 11, 12, 13, 14, 15, and in some instances, 16 or more, amino acid modifications, as further described herein.

In one aspect, the glucagon analog comprises a modified amino acid sequence of SEQ ID NO: 2 comprising the following amino acid modifications: (i) an acylated or alkylated amino acid residue (e.g., an amino acid covalently linked to a C4 to C30 acyl or alkyl group), preferably at position 10, (ii) an alpha helix promoting amino acid at position 16 of SEQ ID NO: 2, (iii) an aliphatic amino acid (e.g., a small aliphatic amino acid) at position 17 and/or 18, and (iv) one or more charged amino acids (e.g., one or more negative-charged residues) C-terminal to position 27.

As used herein, the term "acylated amino acid" refers to an amino acid comprising an acyl group which is non-native to a naturally-occurring amino acid, regardless of the means by which it is produced. As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids. "Non-coded" as used herein refers to an amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. "Coded" as used herein refers to an amino acid that is an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. As used herein the term "charged amino acid" or "charged residue" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

In some embodiments, the glucagon analog comprises (e.g., up to 10) additional amino acid modifications that do not destroy glucagon receptor activity or GLP-1 receptor activity (e.g., modification(s) that permit the analog to maintain an EC50<1 mM at either or both receptors). In exemplary embodiments, any of the amino acid modifications as further described herein may be included in the glucagon analog.

In a second aspect, the glucagon analog comprises a modified amino acid sequence of SEQ ID NO: 2, wherein at least three additional alpha helix promoting amino acids have been added, either by insertion or substitution, at any of positions 12 through 29 of SEQ ID NO: 2. In some specific embodiments, the glucagon analog comprises a modified amino acid sequence of SEQ ID NO: 2, wherein three or all of the amino acids located at positions 16, 17, 20, and 21 of SEQ ID NO: 2 are substituted with alpha helix promoting amino acids. In some exemplary embodiments, the glucagon analog comprises two non-covalent intramolecular bridges. In other exemplary embodiments, the glucagon analog comprises at least one intramolecular bridge (e.g., a non-covalent intramolecular bridge, such as a salt bridge) and an alpha, alpha, di-substituted amino acid (e.g., AIB). In some specific aspects, the glucagon analog comprises (e.g., up to 10) additional amino acid modifications that do not destroy glucagon receptor activity or GLP-1 receptor activity (e.g., modifications that permit the analog to maintain an EC50<1 mM at either or both receptors). In exemplary embodiments, any of the amino acid modifications as further described herein may be included in the glucagon analog.

In a third aspect, the glucagon analog comprises a modified amino acid sequence of SEQ ID NO: 2, wherein at least three (e.g., four, five, six, seven, eight, or all) of the amino acids located at any of positions 16 through 24 of SEQ ID NO: 2 are substituted with the amino acid at the corresponding position of Exendin-4 (SEQ ID NO: 8), or a conservative amino acid substitution thereof. In this regard, in some embodiments, the glucagon analog comprises a modified amino acid sequence of SEQ ID NO: 2, wherein the amino acid at position 16 (Ser) is substituted with the amino acid at position 16 of Exendin-4 (SEQ ID NO: 8) (Glu or a conservative amino acid substitution thereof), the amino acid at position 17 (Arg) is substituted with the amino acid at position 17 of Exendin-4 (SEQ ID NO: 8) (Glu or a conservative amino acid substitution thereof), the amino acid at position 18 (Arg) is substituted with the amino acid at position 18 of Exendin-4 (SEQ ID NO: 8) (Ala or a conservative amino acid substitution thereof), the amino acid at position 19 (Ala) is substituted with the amino acid at position 19 of Exendin-4 (SEQ ID NO: 8) (Val or a conservative amino acid substitution thereof), the amino acid at position 20 (Gln) is substituted with the amino acid at position 20 of Exendin-4 (SEQ ID NO: 8) (Arg or a conservative amino acid substitution thereof), the amino acid at position 21 (Asp) is substituted with the amino acid at position 21 of Exendin-4 (SEQ ID NO: 8) (Leu or a conservative amino acid substitution thereof), the amino acid at position 23 (Val) is substituted with the amino acid at position 23 of Exendin-4 (SEQ ID NO: 8) (Ile or a conservative amino acid substitution thereof), the amino acid at position 24 (Gln) is substituted with the amino acid at position 24 of Exendin-4 (SEQ ID NO: 8) (Glu or a conservative amino acid substitution thereof), or a combination thereof. In some embodiments, the glucagon analog comprises the amino acid sequence AVRLFIX (SEQ ID NO: 11) as positions 18 through 24 of the analog, wherein the X is Cys, (including, e.g., Cys covalently linked to a hydrophilic moiety (e.g., PEG) or Glu. Accordingly, in some aspects, the glucagon analog comprises a modified amino acid sequence of SEQ ID NO: 2 comprising a small aliphatic amino acid at position 18, an aliphatic amino acid at position 19, a positive-charged amino acid at position 20, a charge-neutral amino acid at position 21, a large alphatic amino acid at position 23, an acidic amino acid or a Cys at position 24.

As used herein the term "acidic amino acid" refers to an amino acid that comprises a second acidic moiety, including for example, a carboxylic acid or sulfonic acid group, in addition to the alpha carboxylate of an amino acid. In some specific aspects, the glucagon analog comprises (e.g., up to 10) additional amino acid modifications that do not destroy glucagon receptor activity or GLP-1 receptor activity (e.g., modifications that permit the analog to maintain an EC50<1 mM at either or both receptors). In exemplary embodiments, any of the amino acid modifications as further described herein may be included in the glucagon analog.

According to any of the foregoing aspects, the glucagon analog in some embodiments exhibits at least about 1% glucagon potency and at least about 1% GLP-1 potency. In some embodiments, the glucagon analog exhibits at least about 10% glucagon potency and/or at least about 10% GLP-1 potency. In some embodiments, the glucagon analog exhibits at least about 50% glucagon potency and/or at least about 50% GLP-1 potency. In some embodiments, e.g., when the glucagon analog is in unpegylated form, the glucagon analog exhibits at least about 100% glucagon potency and/or at least about 100% GLP-1 potency, or preferably both. In some embodiments, the glucagon analog exhibits at least 200% glucagon potency and at least 500% GLP-1 potency. In some embodiments, the glucagon analog exhibits a two-fold to five-fold selectivity for GLP-1 receptor compared to glucagon receptor (e.g., an EC50 at the glucagon receptor that is two- to five-fold greater than the EC50 at the GLP-1 receptor). In other embodiments, the glucagon analog exhibits a two-fold to five-fold selectivity for the glucagon receptor compared to the GLP-1 receptor (e.g., an EC50 at the GLP-1 receptor that is two- to five-fold greater than the EC50 at the glucagon receptor). In some embodiments, the analog exhibits GLP potency within about 10-fold of glucagon potency. Combinations of any of the foregoing characteristics are contemplated, e.g., at least 100% glucagon potency and at least 3-fold selectivity for GLP-1 receptor. In some embodiments, conjugation to hydrophilic moieties may reduce potency without significantly affecting selectivity.

The invention further provides conjugates comprising any of the glucagon analogs described herein conjugated to a heterologous moiety. In some embodiments, the conjugate is a fusion peptide or chimeric peptide. In some embodiments, the heterologous moiety is a polymer, e.g., a polyethylene glycol. The invention furthermore provides dimers and multimers of the glucagon analogs described herein.

Moreover, the invention provides pharmaceutical compositions comprising any of the glucagon analogs described herein and a pharmaceutically acceptable carrier. The invention moreover provides a method of treating or preventing a disease or medical condition (e.g., metabolic syndrome, diabetes, obesity, liver steatosis, a neurodegenerative disease, hypoglycemia) in a patient, comprising administering to the patient a pharmaceutical composition comprising any of the glucagon analogs described herein.

BRIEF DESCRIPTION OF THE DRAWINGS

FIG. 1 depicts the amino acid sequences of Peptides 1-19. The sequence at the top is native human glucagon (SEQ ID NO:2). "—NH2" indicates an amide in place of the alpha carboxylate; "OH" represents the alpha carboxylate; horizontal brackets represent lactam bridges between the outermost bracketed amino acids. "O" is ornithine.

FIG. 2 represents the amino acid sequences of the indicated glucagon analogs. "ser" represents the D-isomer of serine; "Aib" indicates an alpha, aminoisobutryic acid residue; "K(γE-C16)" represents a lysine covalently attached to a C16 fatty acyl group via a gamma-glutamic acid spacer; "C" represents a Cys residue attached to a 40 kDa PEG; "amide" indicates that the C-terminal alpha carboxylate is replaced with an amide; "Dmia" is DMIA as taught herein.

FIG. 3 represents the amino acid sequences of the indicated glucagon analogs. The same symbols of FIG. 2 were used in FIG. 3. "K(γE γE-C16)" represents a lysine covalently attached to a C16 fatty acyl group via a gamma-glutamic acid-gamma-glutamic acid dipeptide spacer.

FIG. 4A and FIG. 4B represents the amino acid sequences of the indicated glucagon analogs. The same symbols of FIG. 2 were used in FIGS. 4A and 4B. "acid" as used in these figures indicates that the C-terminal amino acid comprised an alpha carboxylate. "K(C16)" represents a Lys covalently attached to a C16 fatty acyl group.

FIG. 5 represents the amino acid sequences of the indicated glucagon analogs. The same symbols of FIG. 2 were used in FIG. 5. "desAminoH" represents a His residue lacking the alpha amide group. "ACH" represents acetyl-histidine;

Figure 7:
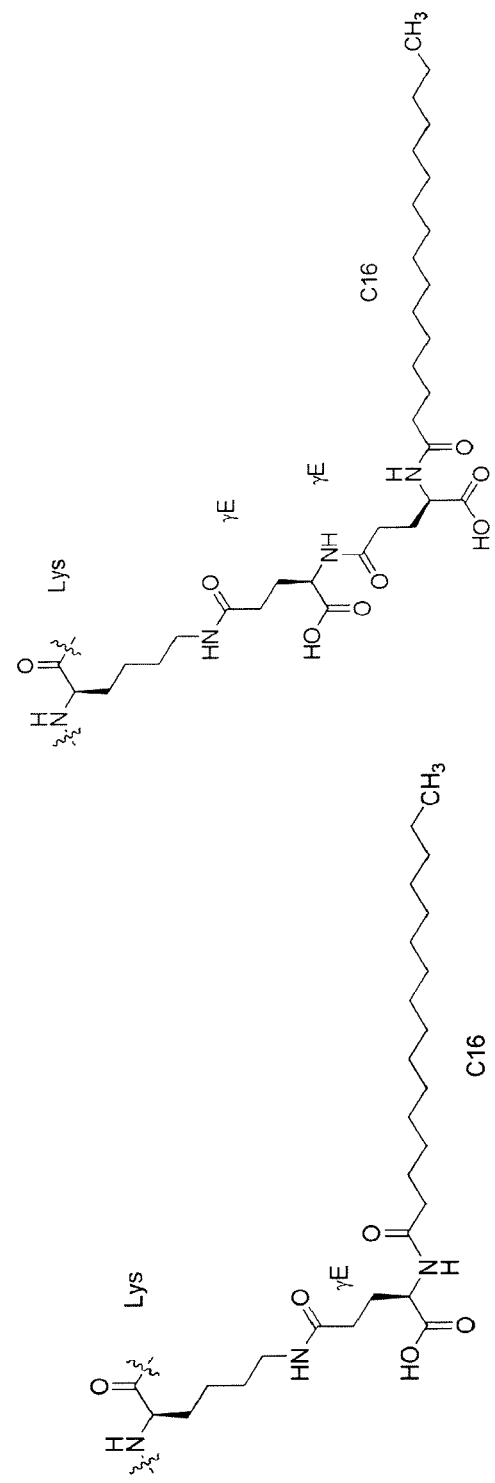

C(PEG-40K-TE) represents a Cys residue attached to a 40 kDa PEG via a thioether linkage made on upon reaction of the thiol with a haloacetyl.

FIG. 6 represents the amino acid sequences of the indicated glucagon analogs. The same symbols of FIG. 5 were used in FIG. 6.

FIG. 7 illustrates an acylated Lys residue in which the epsilon amine is attached to either gamma-glutamic acid spacer or a gamma-glutamic acid-gamma-glutamic acid dipeptide spacer which in turn is attached to a C16 fatty acyl group.

FIGS. 8A-8C illustrate the amino acid sequences of the indicated glucagon analogs. The same symbols of previous figures are used in these figures. "K(B)" represents a lysine covalently attached to a C16 fatty acyl group via a gamma-glutamic acid spacer; "(C)" represents a Cys residue attached to a 40 kDa PEG via a thioether linkage made upon reaction with a haloacetyl; "K(D)" represents a lysine covalently attached to a C16 fatty acyl group via direct attachment to the epsilon amine of lysine; "Cex" represents the fusion of the glucagon analog to the amino acid sequence of SEQ ID NO: 14.

FIG. 9 represents the amino acid sequences of the indicated glucagon analogs. The same or similar symbols used in previous figures were used in FIG. 9. "s" or "ser" represents the D-isomer of serine; "E16-K20 lactam" indicates a lactam bridge connecting the side chains between Glu at position 16 and Lys at position 20; "C(TE-40 KPEG)" or "C*(40KTE) indicates the same as "(C)" of FIGS. 8A-8C. "K(γEC16)" or "K(rEC16)" represents a lysine covalently attached to a C16 fatty acyl group via a gamma-glutamic acid spacer.

Further embodiments contemplated include peptides comprising any of the sequences in any of the figures or the sequence listing, wherein the sequence comprises any of the amino acid modifications described herein, including but not limited to: alternative substitutions at position 1 or 2 that confer DPP-IV resistance; alternative spacers for the acyl or alkyl groups, e.g. dipeptide or single amino acid spacers. Further embodiments also include conjugation to a hydrophilic moiety or another active agent, or fusion to the same or a different peptide or polypeptide; and/or multimerization.

DETAILED DESCRIPTION OF THE INVENTION

The invention provides glucagon analogs which exhibit activity at the GLP-1 receptor, at the glucagon receptor, or at both the GLP-1 receptor and the glucagon receptor. In this regard, the invention provides GLP-1 receptor agonist peptides, glucagon receptor agonist peptides, and GLP-1/glucagon receptor co-agonist peptides. In some embodiments, the glucagon analogs exhibit greater potency at the GLP-1 receptor as compared to native human glucagon (SEQ ID NO: 2). In some embodiments, the glucagon analogs exhibit greater potency at the GLP-1 receptor as compared to native human GLP-1 (SEQ ID NO: 3) or one of the active forms thereof (SEQ ID NOs: 6 and 7). In some embodiments, the glucagon analogs exhibit greater potency at the glucagon receptor compared to native human GLP-1. In some embodiments, the glucagon analogs exhibit greater potency at the glucagon receptor compared to native human glucagon. In some embodiments, the analogs exhibit other improvements in properties, such as greater stability, greater solubility, a prolonged half-life in circulation, a delayed onset of action, an extended duration of action, a dampened peak (e.g., relatively decreased mean peak plasma concentration), and an improved resistance to proteases, such as DPP-IV.

DEFINITIONS

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a glucagon peptide refers to a nontoxic but sufficient amount of the peptide to provide the desired effect. For example one desired effect would be the prevention or treatment of hypoglycemia, as measured, for example, by an increase in blood glucose level. An alternative desired effect for the glucagon peptides of the present disclosure would include treating hyperglycemia, e.g., as measured by a change in blood glucose level closer to normal, or inducing weight loss/preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route, e.g., subcutaneous, intramuscular, intraspinal, or intravenous.

The term "isolated" as used herein means having been removed from its natural environment. In some embodiments, the analog is made through recombinant methods and the analog is isolated from the host cell.

The term "purified," as used herein relates to the isolation of a molecule or compound in a form that is substantially free of contaminants normally associated with the molecule or compound in a native or natural environment and means having been increased in purity as a result of being separated from other components of the original composition. The term "purified polypeptide" is used herein to describe a polypeptide which has been separated from other compounds including, but not limited to nucleic acid molecules, lipids and carbohydrates.

As used herein, the term "peptide" encompasses a sequence of 3 or more amino acids and typically less than 50 amino acids, wherein the amino acids are naturally occurring or coded or non-naturally occurring or non-coded amino acids. Non-naturally occurring amino acids refer to amino acids that do not naturally occur in vivo but which, nevertheless, can be incorporated into the peptide structures described herein.

As used herein, the terms "polypeptide" and "protein" are terms that are used interchangeably to refer to a polymer of amino acids, without regard to the length of the polymer. Typically, polypeptides and proteins have a polymer length that is greater than that of "peptides."

Throughout the application, all references to a particular amino acid position by number (e.g., position 28) refer to the amino acid at that position in native glucagon (SEQ ID NO: 2) or the corresponding amino acid position in any analogs thereof. For example, a reference herein to "position 28" would mean the corresponding position 27 for a glucagon analog in which the first amino acid of SEQ ID NO: 2 has been deleted. Similarly, a reference herein to "position 28" would mean the corresponding position 29 for a glucagon analog in which one amino acid has been added before the N-terminus of SEQ ID NO: 2. As used herein an "amino acid modification" refers to (i) a substitution or replacement of an amino acid of SEQ ID NO: 2 with a different amino acid (naturally-occurring or coded or non-coded or non-naturally-occurring amino acid), (ii) an addition of an amino acid (naturally-occurring or coded or non-coded or non-naturally-occurring amino acid), to SEQ ID NO: 2 or (iii) a deletion of one or more amino acids of SEQ ID NO: 2. "Non-coded" as used herein refer to an amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

In some embodiments, the amino acid substitution or replacement is a conservative amino acid substitution, e.g., a conservative substitution of the amino acid at one or more of positions 2, 5, 7, 10, 11, 12, 13, 14, 16, 17, 18, 19, 20, 21, 24, 27, 28 or 29. As used herein, the term "conservative amino acid substitution" is the replacement of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues:
Ala, Ser, Thr, Pro, Gly;
II. Polar, negative-charged residues and their amides and esters:
Asp, Asn, Glu, Gln, cysteic acid and homocysteic acid;
III. Polar, positive-charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine In some embodiments, the amino acid substitution is not a conservative amino acid substitution, e.g., is a non-conservative amino acid substitution.

As used herein the term "charged amino acid" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "selectivity" of a molecule for a first receptor relative to a second receptor refers to the following ratio: EC50 of the molecule at the second receptor divided by the EC50 of the molecule at the first receptor. For example, a molecule that has an EC50 of 1 nM at a first receptor and an EC50 of 100 nM at a second receptor has 100-fold selectivity for the first receptor relative to the second receptor.

As used herein the term "native glucagon" refers to a peptide consisting of the sequence of SEQ ID NO: 2 and the term "native GLP-1" is a generic term that designates GLP-1(7-36) amide, GLP-1(7-37) acid or a mixture of those two compounds.

As used herein, "glucagon potency" or "potency compared to native glucagon" of a molecule refers to the ratio of the EC50 of the molecule at the glucagon receptor divided by the EC50 of native glucagon at glucagon receptor.

As used herein, "GLP-1 potency" or "potency compared to native GLP-1" of a molecule refers to the ratio of the EC50 of the molecule at GLP-1 receptor divided by the EC50 of native GLP-1 at GLP-1 receptor.

Activity of the Glucagon Analogs
Agonist Activity at the Glucagon Receptor

In some embodiments, the glucagon analogs exhibit an EC50 for glucagon receptor activation of about 1000 μM or less (e.g., about 750 μM or less, about 500 μM or less, about 250 μM or less, about 100 μM or less, about 75 μM or less, about 50 μM or less, about 25 or less, about 10 μM or less, about 7.5 μM or less, about 6 μM or less, about 5 μM or less, about 4 μM or less, about 3 μM or less, about 2 μM or less or about 1 μM or less). In some embodiments, the glucagon analogs exhibit an EC50 for glucagon receptor activation of about 1000 nM or less (e.g., about 750 nM or less, about 500 nM or less, about 250 nM or less, about 100 nM or less, about 75 nM or less, about 50 nM or less, about 25 nM or less, about 10 nM or less, about 7.5 nM or less, about 6 nM or less, about 5 nM or less, about 4 nM or less, about 3 nM or less, about 2 nM or less or about 1 nM or less). In some embodiments, the glucagon analog has an EC50 at the glucagon receptor which is in the picomolar range. Accordingly, in some embodiments, the glucagon analogs exhibit an EC50 for glucagon receptor activation of about 1000 µM or less (e.g., about 750 µM or less, about 500 µM or less, about 250 µM or less, about 100 µM or less, about 75 µM or less, about 50 µM or less, about 25 µM or less, about 10 µM or less, about 7.5 µM or less, about 6 µM or less, about 5 µM or less, about 4 µM or less, about 3 µM or less, about 2 µM or less or about 1 µM or less).

In some embodiments, the glucagon analogs described herein exhibit an EC50 at the glucagon receptor that is about 0.001 µM or more, about 0.01 µM or more, or about 0.1 µM or more. Glucagon receptor activation (glucagon receptor activity) can be measured by in vitro assays measuring cAMP induction in HEK293 cells over-expressing the glucagon receptor, e.g., assaying HEK293 cells co-transfected with DNA encoding the glucagon receptor and a luciferase gene linked to cAMP responsive element as described in Example 2.

In some embodiments, glucagon analogs exhibit about 0.001% or more, about 0.01% or more, about 0.1% or more, about 0.5% or more, about 1% or more, about 5% or more, about 10% or more, about 20% or more, about 30% or more, about 40% or more, about 50% or more, about 60% or more, about 75% or more, about 100% or more, about 125% or more, about 150% or more, about 175% or more, about 200% or more, about 250% or more, about 300% or more, about 350% or more, about 400% or more, about 450% or more, or about 500% or higher activity at the glucagon receptor relative to native glucagon (glucagon potency). In some embodiments, the glucagon analogs described herein exhibit about 5000% or less or about 10,000% or less activity at the glucagon receptor relative to native glucagon. A glucagon analog's activity at a receptor relative to a native ligand of the receptor is calculated as the inverse ratio of EC50s for the glucagon analog vs. the native ligand.

In some embodiments, the glucagon analogs exhibit substantial activity (potency) at only the glucagon receptor and little to no activity at the GLP-1 receptor. In some embodiments, the glucagon analog is considered as a "pure glucagon receptor agonist" or is not considered as a "glucagon/GLP-1 receptor co-agonist." In some embodiments these glucagon analogs exhibit any of the levels of activity or potency at the glucagon receptor described herein but have substantially less activity (potency) at the GLP-1 receptor. In some embodiments, the glucagon analog exhibits an EC50 at the GLP-1 receptor which is 100-fold or greater than the EC50 at the glucagon receptor.

Agonist Activity at the GLP-1 Receptor

In some embodiments, the glucagon analogs exhibit an EC50 for GLP-1 receptor activation of about 1000 µM or less (e.g., about 750 µM or less, about 500 µM or less, about 250 µM or less, about 100 µM or less, about 75 µM or less, about 50 µM or less, about 25 M or less, about 10 µM or less, about 7.5 µM or less, about 6 µM or less, about 5 µM or less, about 4 µM or less, about 3 µM or less, about 2 µM or less or about 1 µM or less). In some embodiments, the glucagon analogs exhibit an EC50 for GLP-1 receptor activation of about 1000 nM or less (e.g., about 750 nM or less, about 500 nM or less, about 250 nM or less, about 100 nM or less, about 75 nM or less, about 50 nM or less, about 25 nM or less, about 10 nM or less, about 7.5 nM or less, about 6 nM or less, about 5 nM or less, about 4 nM or less, about 3 nM or less, about 2 nM or less or about 1 nM or less). In some embodiments, the glucagon analog has an EC50 at the GLP-1 receptor which is in the picomolar range. Accordingly, in some embodiments, the glucagon analogs exhibit an EC50 for GLP-1 receptor activation of about 1000 µM or less (e.g., about 750 µM or less, about 500 µM or less, about 250 µM or less, about 100 µM or less, about 75 µM or less, about 50 µM or less, about 25 µM or less, about 10 µM or less, about 7.5 µM or less, about 6 µM or less, about 5 µM or less, about 4 µM or less, about 3 µM or less, about 2 µM or less or about 1 µM or less).

In some embodiments, the glucagon analogs described herein exhibit an EC50 at the GLP-1 receptor that is about 0.001 µM or more, about 0.01 µM or more, or about 0.1 µM or more. GLP-1 receptor activation (GLP-1 receptor activity) can be measured by in vitro assays measuring cAMP induction in HEK293 cells over-expressing the GLP-1 receptor, e.g., assaying HEK293 cells co-transfected with DNA encoding the GLP-1 receptor and a luciferase gene linked to cAMP responsive element as described in Example 2.

In some embodiments, glucagon analogs exhibit about 0.001% or more, about 0.01% or more, about 0.1% or more, about 0.5% or more, about 1% or more, about 5% or more, about 10% or more, about 20% or more, about 30% or more, about 40% or more, about 50% or more, about 60% or more, about 75% or more, about 100% or more, about 125% or more, about 150% or more, about 175% or more, about 200% or more, about 250% or more, about 300% or more, about 350% or more, about 400% or more, about 450% or more, or about 500% or higher activity at the GLP-1 receptor relative to native GLP-1 (GLP-1 potency). In some embodiments, the glucagon analogs described herein exhibit about 5000% or less or about 10,000% or less activity at the GLP-1 receptor relative to native GLP-1 (GLP-1 potency).

In some embodiments, the glucagon analogs exhibit substantial activity (potency) at only the GLP-1 receptor and little to no activity at the glucagon receptor. In some embodiments, the glucagon analog is considered as a "pure GLP-1 receptor agonist" or is not considered as a "glucagon/GLP-1 receptor co-agonist." In some embodiments these glucagon analogs exhibit any of the levels of activity or potency at the GLP-1 receptor described herein but have substantially less activity (potency) at the glucagon receptor. In some embodiments, the glucagon analog exhibits an EC50 at the glucagon receptor which is 100-fold or greater than the EC50 at the GLP-1 receptor.

Agonist Activity at the GLP-1 Receptor and the Glucagon Receptor

In some embodiments, the glucagon analog exhibits activity at both the GLP-1 receptor and glucagon receptor ("glucagon/GLP-1 receptor co-agonists"). In some embodiments, the activity (e.g., the EC50 or the relative activity or potency) of the glucagon analog at the glucagon receptor is within about 50-fold, about 40-fold, about 30-fold, about 20-fold, about 10-fold, or about 5 fold different (higher or lower) from its activity (e.g., the EC50 or the relative activity or potency) at the GLP-1 receptor. In some embodiments, the glucagon potency of the glucagon analog is within about 25-, about 20-, about 15-, about 10-, or about 5-fold different (higher or lower) from its GLP-1 potency.

In some embodiments, the ratio of the relative activity or the EC50 or the potency of the glucagon analog at the glucagon receptor divided by the relative activity or the EC50 or potency of the glucagon analog at the GLP-1 receptor is less than, or is about, X, wherein X is selected from 100, 75, 60, 50, 40, 30, 20, 15, 10, or 5. In some embodiments, the ratio of the EC50 or potency or relative activity of the glucagon analog at the glucagon receptor divided by the EC50 or potency or relative activity of the glucagon analog at the GLP-1 receptor is about 1 less than 5 (e.g., about 4, about 3, about 2, about 1). In some embodiments, the ratio of the glucagon potency of the glucagon analog compared to the GLP-1 potency of the glucagon analog is less than, or is about, Y, wherein Y is selected from 100, 75, 60, 50, 40, 30, 20, 15, 10, and 5. In some embodiments, the ratio of the glucagon potency of the glucagon analog compared to the GLP-1 potency of the glucagon analog is less than 5 (e.g., about 4, about 3, about 2, about 1). In some embodiments, the glucagon analog has an EC50 at the glucagon receptor which is 2- to 10-fold (e.g., 2-fold, 3-fold, 4-fold, 5-fold, 6-fold, 7-fold, 8-fold, 9-fold, 10-fold) greater than the EC50 at the GLP-1 receptor.

In some embodiments, the ratio of the relative activity or potency or the EC50 of the glucagon analog at the GLP-1 receptor divided by the relative activity or potency or the EC50 of the glucagon analog at the glucagon receptor is less than, or is about, V, wherein V is selected from 100, 75, 60, 50, 40, 30, 20, 15, 10, or 5. In some embodiments, the ratio of the EC50 or potency or relative activity of the glucagon analog at the GLP-1 receptor divided by the EC50 or potency or relative activity of the glucagon analog at the glucagon receptor is less than 5 (e.g., about 4, about 3, about 2, about 1). In some embodiments, the ratio of the GLP-1 potency of the glucagon analog compared to the glucagon potency of the glucagon analog is less than, or is about, W, wherein W is selected from 100, 75, 60, 50, 40, 30, 20, 15, 10, and 5. In some embodiments, the ratio of the GLP-1 potency of the glucagon analog compared to the glucagon potency of the glucagon analog is less than 5 (e.g., about 4, about 3, about 2, about 1). In some embodiments, the glucagon analog has an EC50 at the GLP-1 receptor which is about 2- to about 10-fold (e.g., 2-fold, 3-fold, 4-fold, 5-fold, 6-fold, 7-fold, 8-fold, 9-fold, 10-fold) greater than the EC50 at the glucagon receptor.

In some embodiments, the glucagon analog exhibits at least 0.1% (e.g., about 0.5% or more, about 1% or more, about 5% or more, about 10% or more, or more) of the activity of native GLP-1 at the GLP-1 receptor (GLP-1 potency) and exhibits at least 0.1% (e.g., about 0.5% or more, about 1% or more, about 5% or more, about 10% or more, or more) of the activity of native glucagon at the glucagon receptor (glucagon potency).

Selectivity of a glucagon analog for the glucagon receptor versus the GLP-1 receptor can be described as the relative ratio of glucagon/GLP-1 activity (the analog's activity at the glucagon receptor relative to native glucagon, divided by the analog's activity at the GLP-1 receptor relative to native GLP-1). For example, a glucagon analog that exhibits 60% of the activity of native glucagon at the glucagon receptor and 60% of the activity of native GLP-1 at the GLP-1 receptor has a 1:1 ratio of glucagon/GLP-1 activity. Exemplary ratios of glucagon/GLP-1 activity include about 1:1, 1.5:1, 2:1, 3:1, 4:1, 5:1, 6:1, 7:1, 8:1, 9:1 or 10:1, or about 1:10, 1:9, 1:8, 1:7, 1:6, 1:5, 1:4, 1:3, 1:2, or 1:1.5. As an example, a glucagon/GLP-1 activity ratio of 10:1 indicates a 10-fold selectivity for the glucagon receptor versus the GLP-1 receptor. Similarly, a GLP-1/glucagon activity ratio of 10:1 indicates a 10-fold selectivity for the GLP-1 receptor versus the glucagon receptor.

Activity of Conjugates

In some embodiments, the glucagon analogs described herein exhibit activity or potency at the glucagon receptor and/or activity at the GLP-1 receptor as described above and, when the glucagon analog is part of a conjugate (e.g., is conjugated to a heterologous moiety, e.g., a hydrophilic moiety, e.g., a polyethylene glycol), the glucagon analog exhibits an activity that is lower (i.e. lower potency or higher EC50) than when the analog is not part of the conjugate. In some aspects, the glucagon analog when not part of conjugate exhibits a potency at the glucagon receptor and/or the GLP-1 receptor that is about 10-fold or greater than the potency of the glucagon analog when part of a conjugate. In some aspects, the glucagon analog when unconjugated exhibits an potency at the glucagon receptor and/or GLP-1 receptor that is about 10-fold, about 15-fold, about 20-fold, about 25-fold, about 30-fold, about 35-fold, about 40-fold, about 45-fold, about 50-fold, about 100-fold, or even greater-fold the potency of the glucagon analog when conjugated.

Structure of the Glucagon Analogs

The glucagon analogs described herein comprise an amino acid sequence which is based on the amino acid sequence of native human glucagon (SEQ ID NO: 2). In some aspects, the glucagon analogs described herein comprise a modified amino acid sequence of SEQ ID NO: 2 comprising 1, 2, 3, 4, 5, 6, 7, 8, 9, 10, 11, 12, 13, 14, 15, and in some instances, 16 or more (e.g., 17, 18, 19, 20, 21, 22, 23, 24, 25, etc.), amino acid modifications. In some embodiments, the glucagon analog comprises a total of 1, up to 2, up to 3, up to 4, up to 5, up to 6, up to 7, up to 8, up to 9, or up to 10 amino acid modifications relative to the native human glucagon sequence (SEQ ID NO: 2). In some embodiments, the modifications are any of those described herein, e.g., acylation, alkylation, pegylation, truncation at C-terminus, substitution of the amino acid at one or more of positions 1, 2, 3, 7, 10, 12, 15, 16, 17, 18, 19, 20, 21, 23, 24, 27, 28, and 29.

Percent Identity

In some embodiments, the glucagon analog described herein comprises an amino acid sequence which has at least 25% sequence identity to the amino acid sequence of native human glucagon (SEQ ID NO: 2). In some embodiments, the glucagon analog comprises an amino acid sequence which is at least 30%, at least 40%, at least 50%, at least 60%, at least 70%, at least 80%, at least 85%, at least 90% or has greater than 90% sequence identity to SEQ ID NO: 2. In some embodiments, the amino acid sequence of the glucagon analog which has the above-referenced % sequence identity is the full-length amino acid sequence of the glucagon analog. In some embodiments, the amino acid sequence of the glucagon analog which has the above-referenced % sequence identity is only a portion of the amino acid sequence of the glucagon analog. In some embodiments, the glucagon analog comprises an amino acid sequence which has about A % or greater sequence identity to a reference amino acid sequence of at least 5 contiguous amino acids (e.g., at least 6, at least 7, at least 8, at least 9, at least 10 amino acids) of SEQ ID NO: 2, wherein the reference amino acid sequence begins with the amino acid at position C of SEQ ID NO: 2 and ends with the amino acid at position D of SEQ ID NO: 2, wherein A is 25, 30, 35, 40, 45, 50, 55, 60, 65, 70, 75, 80, 85, 90, 91, 92, 93, 94, 95, 96, 97, 98, 99; C is 1, 2, 3, 4, 5, 6, 7, 8, 9, 10, 11, 12, 13, 14, 15, 16, 17, 18, 19, 20, 21, 22, 23, 24, 25, 26, 27, or 28 and D is 5, 6, 7, 8, 9, 10, 11, 12, 13, 14, 15, 16, 17, 18, 19, 20, 21, 22, 23, 24, 25, 26, 27, 28 or 29. Any and all possible combinations of the foregoing parameters are envisioned, including but not limited to, e.g., wherein A is 90% and C and D are 1 and 27, or 6 and 27, or 8 and 27, or 10 and 27, or 12 and 27, or 16 and 27.

Peptide Length

The glucagon analogs described herein may comprise a peptide backbone of any number of amino acids, i.e., can be of any peptide length. In some embodiments, the glucagon analogs described herein are the same length as SEQ ID NO: 2, i.e., are 29 amino acids in length. In some embodiments, the glucagon analog is longer than 29 amino acids in length, e.g., the glucagon analog comprises a C-terminal extension of 1-21 amino acids, as further described herein. Accordingly, the glucagon analog in some embodiments, is 30, 31, 32, 33, 34, 35, 36, 37, 38, 39, 40, 41, 42, 43, 44, 45, 46, 47, 48, 49, or 50 amino acids in length. In some embodiments, the glucagon analog is longer than 29 amino acids in length (e.g., greater than 50 amino acids, (e.g., at least 60, at least 70, at least 80, at least 90, at least 100, at least 150, at least 200, at least 250, at least 300, at least 350, at least 400, at least 450, at least 500 amino acids in length) due to fusion with another peptide. In other embodiments, the glucagon analog is less than 29 amino acids in length, e.g., 28, 27, 26, 25, 24, 23, amino acids.

Acylation

In accordance with some embodiments, the glucagon analog comprises an acylated amino acid (e.g., a non-coded acylated amino acid (e.g., an amino acid comprising an acyl group which is non-native to a naturally-occurring amino acid)). The acylated amino acid in some embodiments causes the glucagon analog to have one or more of (i) a prolonged half-life in circulation, (ii) a delayed onset of action, (iii) an extended duration of action, (iv) an improved resistance to proteases, such as DPP-IV, and (v) increased potency at one or both of the GLP-1 and glucagon receptors. As shown herein, acylated glucagon analogs do not exhibit decreased activity at the glucagon and GLP-1 receptors in comparison to the corresponding unacylated glucagon analog. Rather, in some instances, acylated glucagon analogs actually exhibit increased activity at the GLP-1 and glucagon receptors. Accordingly, the potency of the acylated glucagon analogs is comparable to the unacylated versions of the glucagon analogs, if not enhanced.

In accordance with one embodiment, the glucagon analog comprises an acyl group which is attached to the glucagon analog via an ester, thioester, or amide linkage for purposes of prolonging half-life in circulation and/or delaying the onset of and/or extending the duration of action and/or improving resistance to proteases such as DPP-IV.

Acylation can be carried out at any position within the glucagon analog, including any of positions 1-29, a position C-terminal to the 29$^{th}$ amino acid (e.g., the amino acid at position 30, 31, 32, 33, 34, 35, 36, 37, 38, 39, 40, 41, 42, 43, 44, 45, 46, 47, etc., at a position within a C-terminal extension or at the C-terminus), provided that glucagon and/or GLP-1 activity is retained, if not enhanced. Nonlimiting examples include positions 5, 7, 10, 11, 12, 13, 14, 16, 17, 18, 19, 20, 21, 24, 27, 28, or 29. In specific embodiments, acylation occurs at position 10 of the glucagon analog and the glucagon analog lacks an intramolecular bridge, e.g., a covalent intramolecular bridge (e.g., a lactam bridge). Such acylated glucagon analogs lacking an intramolecular bridge demonstrate enhanced activity at the GLP-1 and glucagon receptors as compared to the corresponding non-acylated analogs lacking a covalent intramolecular bridge and in comparison to the corresponding analogs lacking an intramolecular bridge acylated at a position other than position 10. As shown herein, acylation at position 10 can even transform a glucagon analog having little activity at the glucagon receptor to a glucagon analog having activity at both the glucagon and GLP-1 receptors. Accordingly, the position at which acylation occurs can alter the overall activity profile of the glucagon analog.

The glucagon analog in some embodiments are acylated at the same amino acid position where a hydrophilic moiety is linked, or at a different amino acid position. Nonlimiting examples include acylation at position 10 and pegylation at one or more positions in the C-terminal portion of the glucagon analog, e.g., position 24, 28 or 29, within a C-terminal extension, or at the C-terminus (e.g., through adding a C-terminal Cys).

The acyl group can be covalently linked directly to an amino acid of the glucagon analog, or indirectly to an amino acid of the glucagon analog via a spacer, wherein the spacer is positioned between the amino acid of the glucagon analog and the acyl group.

In specific aspects, the glucagon analog is modified to comprise an acyl group by direct acylation of an amine, hydroxyl, or thiol of a side chain of an amino acid of the glucagon analog. In some embodiments, acylation is at position 10, 20, 24, or 29 of the glucagon analog. In this regard, the acylated glucagon analog can comprise the amino acid sequence of SEQ ID NO: 2, or a modified amino acid sequence thereof comprising one or more of the amino acid modifications described herein, with at least one of the amino acids at positions 10, 20, 24, and 29 of the analog modified to any amino acid comprising a side chain amine, hydroxyl, or thiol. In some specific embodiments, the direct acylation of the glucagon analog occurs through the side chain amine, hydroxyl, or thiol of the amino acid at position 10.

In some embodiments, the amino acid comprising a side chain amine is an amino acid of Formula I:

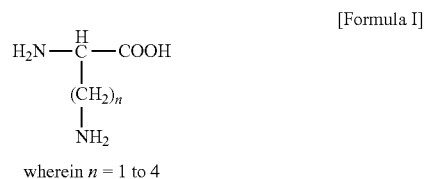

wherein $n$ = 1 to 4

In some exemplary embodiments, the amino acid of Formula I, is the amino acid wherein n is 4 (Lys) or n is 3 (Orn).

In other embodiments, the amino acid comprising a side chain hydroxyl is an amino acid of Formula II:

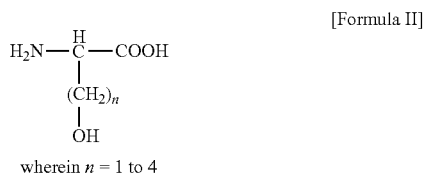

wherein $n$ = 1 to 4

In some exemplary embodiments, the amino acid of Formula II is the amino acid wherein n is 1 (Ser).

In yet other embodiments, the amino acid comprising a side chain thiol is an amino acid of Formula III:

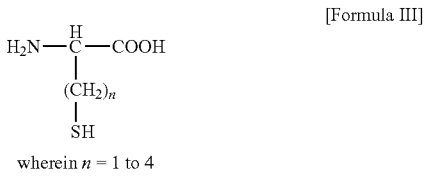

wherein $n$ = 1 to 4

In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In some embodiments, the acylated glucagon comprises a spacer between the analog and the acyl group. In some embodiments, the glucagon analog is covalently bound to the spacer, which is covalently bound to the acyl group.

In some embodiments, the spacer is an amino acid comprising a side chain amine, hydroxyl, or thiol, or a dipeptide or tripeptide comprising an amino acid comprising a side chain amine, hydroxyl, or thiol. The amino acid to which the spacer is attached can be any amino acid (e.g., a singly or doubly α-substituted amino acid) comprising a moiety which permits linkage to the spacer. For example, an amino acid comprising a side chain $NH_2$, —OH, or —COON (e.g., Lys, Orn, Ser, Asp, or Glu) is suitable. In this respect, the acylated glucagon analog can comprise the amino acid sequence of SEQ ID NO: 2, or a modified amino acid sequence thereof comprising one or more of the amino acid modifications described herein, with at least one of the amino acids at positions 10, 20, 24, and 29 modified to any amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol.

When acylation occurs through an amine group of a spacer, the acylation can occur through the alpha amine of the amino acid or a side chain amine. In the instance in which the alpha amine is acylated, the amino acid of the spacer can be any amino acid. For example, the amino acid of the spacer can be a hydrophobic amino acid, e.g., Gly, Ala, Val, Leu, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp, Glu, homoglutamic acid, homocysteic acid, cysteic acid, gamma-glutamic acid.

In the instance in which the side chain amine of the amino acid of the spacer is acylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be acylated, such that the glucagon analog is diacylated. Embodiments of the invention include such diacylated molecules.

When acylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of a spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

In some embodiments, the spacer is a hydrophobic bifunctional spacer. Hydrophobic bifunctional spacers are known in the art. See, e.g., Bioconjugate Techniques, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups.

The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the acyl group is a C12 to C18 fatty acyl group, e.g., C14 fatty acyl group, C16 fatty acyl group, such that the total length of the spacer and acyl group is 14 to 28 atoms, e.g., about 14, 15, 16, 17, 18, 19, 20, 21, 22, 23, 24, 25, 26, 27, or 28 atoms. In some embodiments, the length of the spacer and acyl group is 17 to 28 (e.g., 19 to 26, 19 to 21) atoms.

In accordance with certain foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring or coded and/or non-coded or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring or non-coded amino acids selected from the group consisting of: β-alanine (β-Ala), N-α-methyl-alanine (Me-Ala), aminobutyric acid (Abu), γ-aminobutyric acid (γ-Abu), aminohexanoic acid (e-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met($O_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-$NO_2$)), 4-cyanophenylalanine ((Phe(4-CN)), phenylglycine (Phg), piperidinylalanine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (MeVal), and alkylated 3-mercaptopropionic acid.

In some embodiments, the spacer comprises an overall negative charge, e.g., comprises one or two negative-charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the dipeptide spacer is selected from the group consisting of: Ala-Ala, β-Ala-β-Ala, Leu-Leu, Pro-Pro, γ-aminobutyric acid-γ-aminobutyric acid, Glu-Glu, and γ-Glu-γ-Glu.

In some exemplary embodiments, the glucagon analog is modified to comprise an acyl group by acylation of an amine, hydroxyl, or thiol of a spacer, which spacer is attached to a side chain of an amino acid at position 10, 20, 24, or 29, or at the C-terminal amino acid of the glucagon analog.

In yet more specific embodiments, the acyl group is attached to the amino acid at position 10 of the glucagon analog and the length of the spacer and acyl group is 14 to 28 atoms. The amino acid at position 10, in some aspects, is an amino acid of Formula I, e.g., Lys, or a disubstituted amino acid related to Formula I. In more specific embodiments, the glucagon analog lacks an intramolecular bridge, e.g., a covalent intramolecular bridge. The glucagon analog, for example, can be a glucagon analog comprising one or more alpha, alpha-disubstituted amino acids, e.g., AIB, for stabilizing the alpha helix of the analog.

Suitable methods of peptide acylation via amines, hydroxyls, and thiols are known in the art. See, for example, Example 19 (for methods of acylating through an amine), Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, J Pept Res 66: 169-180 (2005) (for methods of acylating through a thiol); Bioconjugate Chem. "Chemical Modifications of Proteins: History and Applications" pages 1, 2-12 (1990); Hashimoto et al., Pharmaceutical Res. "Synthesis of Palmitoyl Derivatives of Insulin and their Biological Activity" Vol. 6, No: 2 pp. 171-176 (1989).

The acyl group of the acylated amino acid can be of any size, e.g., any length carbon chain, and can be linear or branched. In some specific embodiments, the acyl group is a C4 to C30 fatty acid. For example, the acyl group can be any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the acyl group is a C8 to C20 fatty acid, e.g., a C14 fatty acid or a C16 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In some embodiments, the glucagon analog comprises an acylated amino acid by acylation of a long chain alkane by the glucagon analog. In specific aspects, the long chain alkane comprises an amine, hydroxyl, or thiol group (e.g., octadecylamine, tetradecanol, and hexadecanethiol) which reacts with a carboxyl group, or activated form thereof, of the glucagon analog. The carboxyl group, or activated form thereof, of the glucagon analog can be part of a side chain of an amino acid (e.g., glutamic acid, aspartic acid) of the glucagon analog or can be part of the analog backbone.

In certain embodiments, the glucagon analog is modified to comprise an acyl group by acylation of the long chain alkane by a spacer which is attached to the glucagon analog. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers.

As used herein, the term "activated form of a carboxyl group" refers to a carboxyl group with the general formula R(C=O)X, wherein X is a leaving group and R is the glucagon analog or the spacer. For example, activated forms of a carboxyl groups may include, but are not limited to, acyl chlorides, anhydrides, and esters. In some embodiments, the activated carboxyl group is an ester with a N-hydroxysuccinimide ester (NHS) leaving group.

With regard to these aspects, in which a long chain alkane is acylated by the glucagon analog or the spacer, the long chain alkane may be of any size and can comprise any length of carbon chain. The long chain alkane can be linear or branched. In certain aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, an amine, hydroxyl, or thiol group of the glucagon analog is acylated with a cholesterol acid. In a specific embodiment, the glucagon analog is linked to the cholesterol acid through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety. In one embodiment, the glucagon analog comprises the structure:

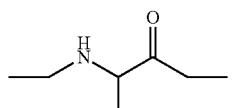
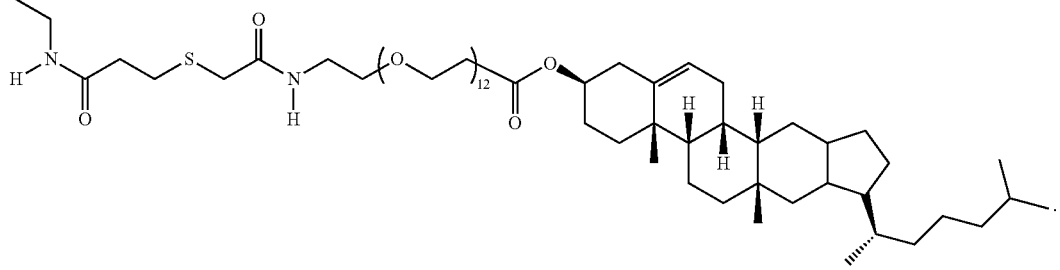

The acylated glucagon analogs described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the acylated glucagon analog can comprise SEQ ID NO: 2, including any of the modifications described herein, in which at least one of the amino acids at position 10, 20, 24, and 29 of the analog comprises an acyl group and at least one of the amino acids at position 16, 17, 21, 24, or 29, a position within a C-terminal extension, or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the acyl group is attached to position 10, optionally via a spacer comprising Cys, Lys, Orn, homo-Cys, or Ac-Phe, and the hydrophilic moiety is incorporated at a Cys residue at position 24.

Alternatively, the acylated glucagon analog can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Alkylation

In accordance with some embodiments, the glucagon analog comprises an alkylated amino acid (e.g., a non-coded alkylated amino acid (e.g., an amino acid comprising an alkyl group which is non-native to a naturally-occurring amino acid)). Without being held to any particular theory, it is believed that alkylation of glucagon analogs achieve similar, if not the same, effects as acylation of the glucagon analogs, e.g., a prolonged half-life in circulation, a delayed onset of action, an extended duration of action, an improved resistance to proteases, such as DPP-IV, and increased potency at the GLP-1 and glucagon receptors.

Alkylation can be carried out at any positions within the glucagon analog, including any of the positions described herein as a site for acylation, including but not limited to, any of amino acid positions 1-29, an amino acid position C-terminal to the 29$^{th}$ residue, e.g., 30, 31, 32, 33, 34, 35, 36, 37, 38, 39, 40, 41, 42, 43, 44, 45, 46, 47, etc., at a position within a C-terminal extension, or at the C-terminus, provided that the glucagon activity or GLP-1 activity is retained. Nonlimiting examples include positions 5, 7, 10, 11, 12, 13, 14, 16, 17, 18, 19, 20, 21, 24, 27, 28, or 29. The alkyl group can be covalently linked directly to an amino acid of the glucagon analog, or indirectly to an amino acid of the glucagon analog via a spacer, wherein the spacer is positioned between the amino acid of the glucagon analog and the alkyl group. Glucagon analog may be alkylated at the same amino acid position where a hydrophilic moiety is linked, or at a different amino acid position. Nonlimiting examples include alkylation at position 10 and pegylation at one or more positions in the C-terminal portion of the glucagon analog, e.g., position 24, 28 or 29, within a C-terminal extension, or at the C-terminus (e.g., through adding a C-terminal Cys).

In specific aspects, the glucagon analog is modified to comprise an alkyl group by direct alkylation of an amine, hydroxyl, or thiol of a side chain of an amino acid of the glucagon analog. In some embodiments, alkylation is at position 10, 20, 24, or 29 of the glucagon analog. In this regard, the alkylated glucagon analog can comprise the amino acid sequence of SEQ ID NO: 2, or a modified amino acid sequence thereof comprising one or more of the amino acid modifications described herein, with at least one of the amino acids at positions 10, 20, 24, and 29 modified to any amino acid comprising a side chain amine, hydroxyl, or thiol. In some specific embodiments, the direct alkylation of the glucagon analog occurs through the side chain amine, hydroxyl, or thiol of the amino acid at position 10.

In some embodiments, the amino acid comprising a side chain amine is an amino acid of Formula I. In some exemplary embodiments, the amino acid of Formula I, is the amino acid wherein n is 4 (Lys) or n is 3 (Orn).

In other embodiments, the amino acid comprising a side chain hydroxyl is an amino acid of Formula II. In some exemplary embodiments, the amino acid of Formula II is the amino acid wherein n is 1 (Ser).

In yet other embodiments, the amino acid comprising a side chain thiol is an amino acid of Formula III. In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In some embodiments, the alkylated glucagon analog comprises a spacer between the analog and the alkyl group. In some embodiments, the glucagon analog is covalently bound to the spacer, which is covalently bound to the alkyl group. In some exemplary embodiments, the glucagon analog is modified to comprise an alkyl group by alkylation of an amine, hydroxyl, or thiol of a spacer, which spacer is attached to a side chain of an amino acid at position 10, 20, 24, or 29 of the glucagon analog. The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In this respect, the alkylated glucagon analog can comprise a modified amino acid sequence of SEQ ID NO: 2, comprising one or more of the amino acid modifications described herein, with at least one of the amino acids at positions 10, 20, 24, and 29 modified to any amino acid comprising a side chain amine, hydroxyl, or carboxylate.

In some embodiments, the spacer is an amino acid comprising a side chain amine, hydroxyl, or thiol or a dipeptide or tripeptide comprising an amino acid comprising a side chain amine, hydroxyl, or thiol.

When alkylation occurs through an amine group of a spacer, the alkylation can occur through the alpha amine of an amino acid or a side chain amine. In the instance in which the alpha amine is alkylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp and Glu, provided that the alkylation occurs on the alpha amine of the acidic residue. In the instance in which the side chain amine of the amino acid of the spacer is alkylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be alkylated, such that the glucagon analog is dialkylated. Embodiments of the invention include such dialkylated molecules.

When alkylation occurs through a hydroxyl group of a spacer, the amino acid or one of the amino acids of the dipeptide or tripeptide can be an amino acid of Formula II. In a specific exemplary embodiment, the amino acid is Ser. When alkylation occurs through a thiol group of spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer is comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

In some embodiments, the spacer is a hydrophobic bifunctional spacer. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydropholic bifunctional spacer comprises an amine group and a carboxylate. In other embodiments, the hydropholic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms)) in length. In more specific embodiments, the spacer is about 3 to 10 atoms (e.g., 6 to 10 atoms) in length and the alkyl is a C12 to C18 alkyl group, e.g., C14 alkyl group, C16 alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments, the length of the spacer and alkyl is 17 to 28 (e.g., 19 to 26, 19 to 21) atoms.

In accordance with certain foregoing embodiments, the bifunctional spacer can be a synthetic or non-naturally occurring or non-coded amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer can be composed of naturally-occurring or coded and/or non-coded or non-naturally occurring amino acids, including, for example, any of the amino acids taught herein. In some embodiments, the spacer comprises an overall negative charge, e.g., comprises one or two negative-charged amino acids. In some embodiments, the dipeptide spacer is selected from the group consisting of: Ala-Ala, β-Ala-Leu-Leu, Pro-Pro, γ-aminobutyric acid-γ-aminobutyric acid, and γ-Glu-γ-Glu.

Suitable methods of peptide alkylation via amines, hydroxyls, and thiols are known in the art. For example, a Williamson ether synthesis can be used to form an ether linkage between a hydroxyl group of the glucagon analog and the alkyl group. Also, a nucleophilic substitution reaction of the peptide with an alkyl halide can result in any of an ether, thioether, or amino linkage.

The alkyl group of the alkylated glucagon analog can be of any size, e.g., any length carbon chain, and can be linear or branched. In some embodiments, the alkyl group is a C4 to C30 alkyl. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

In some embodiments of the disclosure, the glucagon analog comprises an alkylated amino acid by reacting a nucleophilic, long chain alkane with the glucagon analog, wherein the glucagon analog comprises a leaving group suitable for nucleophilic substitution. In specific aspects, the nucleophilic group of the long chain alkane comprises an amine, hydroxyl, or thiol group (e.g., octadecylamine, tetradecanol, and hexadecanethiol). The leaving group of the glucagon analog can be part of a side chain of an amino acid or can be part of the peptide backbone. Suitable leaving groups include, for example, N-hydroxysuccinimide, halogens, and sulfonate esters.

In certain embodiments, the glucagon analog is modified to comprise an alkyl group by reacting the nucleophilic, long chain alkane with a spacer which is attached to the glucagon analog, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group.

With regard to these aspects of the disclosure, in which a long chain alkane is alkylated by the glucagon analog or the spacer, the long chain alkane may be of any size and can comprise any length of carbon chain. The long chain alkane can be linear or branched. In certain aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, alkylation can occur between the glucagon analog and a cholesterol moiety. For example, the hydroxyl group of cholesterol can displace a leaving group on the long chain alkane to form a cholesterol-glucagon analog product.

The alkylated glucagon analogs described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the alkylated glucagon analog can comprise a modified SEQ ID NO: 2 comprising one or more of the amino acid modifications described herein, in which at least one of the amino acids at position 10, 20, 24, and 29 comprise an alkyl group and at least one of the amino acids at position 16, 17, 21, 24, and 29, a position within a C-terminal extension or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the alkyl group is attached to position 10, optionally via a spacer comprising Cys, Lys, Orn, homo-Cys, or Ac-Phe, and the hydrophilic moiety is incorporated at a Cys residue at position 24.

Alternatively, the alkylated glucagon analog can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Stabilization of the Alpha Helix and Alpha Helix Promoting Amino Acids

Without being bound to any particular theory, the glucagon analogs described herein comprise a helical structure, e.g., an alpha helix. In some embodiments, the glucagon analog comprises amino acids which stabilize the alpha helical structure. Accordingly, in some aspects, the glucagon analog comprises one or more alpha helix promoting amino acids. As used herein, the term "alpha helix promoting amino acid" refers to an amino acid which provides increased stability to an alpha helix of the glucagon analog of which it is a part. Alpha helix promoting amino acids are known in the art. See, for example, Lyu et al., *Proc Natl Acad Sci U.S.A.* 88: 5317-5320 (1991); Branden & Tooze, *Introduction to Protein Structure*, Garland Publishing, New York, N.Y., 1991; Fasman, *Prediction of Protein Structure and the Principles of Protein Conformation*, ed. Fasman, Plenum, N.Y., 1989). Suitable alpha helix promoting amino acids for purposes herein include, but are not limited to: alanine, norvaline, norleucine, alpha aminobutyric acid, alpha-aminoisobutyric acid, leucine, isoleucine, valine, and the like. In some embodiments, the alpha helix promoting amino acid is any amino acid which is part of an alpha helix found in a naturally-occurring protein, e.g., Leu, Phe, Ala, Met, Gly, Ile, Ser, Asn, Glu, Asp, Lys, Arg.

In some embodiments, the alpha helix promoting amino acid provides more stability to the alpha helix as compared to glycine or alanine. In some embodiments, the alpha helix promoting amino acid is an alpha, alpha di-substituted amino acid.

Alpha Helix: Position of Alpha Helix Promoting Amino Acids

In some embodiments, the glucagon analog comprises an amino acid sequence which is similar to native glucagon (SEQ ID NO: 2) and the glucagon analog comprises at least one alpha helix promoting amino acid. In some embodiments, the alpha helix promoting amino acid is located at any of positions 12 to 29 (according to the numbering of native glucagon (SEQ ID NO: 2). In some embodiments, the glucagon analog comprises a modified amino acid sequence of SEQ ID NO: 2 and comprises at least one alpha helix promoting amino acid, e.g., at one or more of positions 12, 13, 14, 15, 16, 17, 18, 19, 20, 21, 22, 23, 24, 25, 26, 27, 28, 29. In some embodiments, the glucagon analog comprises an alpha helix promoting amino acid at one, two, three, or all of positions 16, 17, 20, and 21.

Alpha Helix: Alpha, Alpha Di-Substituted Amino Acids

In some embodiments, the alpha helix promoting amino acid is an alpha,alpha di-substituted amino acid. In specific embodiments, the alpha, alpha di-substituted amino acid comprises $R^1$ and $R^2$, each of which is bonded to the alpha carbon, wherein each of $R^1$ and $R^2$ is independently selected from the group consisting of C1-C4 alkyl, optionally substituted with a hydroxyl, amide, thiol, halo, or $R^1$ and $R^2$ together with the alpha carbon to which they are attached form a ring (e.g., a C3-C8 ring). In some embodiments, each of $R^1$ and $R^2$ is selected from the group consisting of: methyl, ethyl, propyl, and n-butyl, or $R^1$ and $R^2$ together form a cyclooctane or cycloheptane (e.g., 1-aminocyclooctane-1-carboxylic acid). In some embodiments, $R^1$ and $R^2$ are the same. In some embodiments, $R^1$ is different from $R^2$. In certain aspects, each of $R^1$ and $R^2$ is a C1-C4 alkyl. In some aspects, each of $R^1$ and $R^2$ is a C1 or C2 alkyl. In some embodiments, each of $R^1$ and $R^2$ is methyl, such that the alpha, alpha disubstituted amino acid is alpha-aminoisobutyric acid (AIB).

In some aspects, the glucagon analogs described herein comprises one or more alpha, alpha di-substituted amino acids and the glucagon analogs specifically lack a covalent intramolecular bridge (e.g., a lactam), since the alpha, alpha disubstituted amino acid is capable of stabilizing the alpha helix in the absence of a covalent bridge. In some aspects, the glucagon analog comprises one or more alpha, alpha di-substituted amino acids at the C-terminus (around positions 12-29). In some embodiments, one, two, three, four or more of positions 16, 17, 18, 19, 20, 21, 24 or 29 of the glucagon analog is substituted with an α,α-disubstituted amino acid, e.g., amino iso-butyric acid (AIB), an amino acid disubstituted with the same or a different group selected from methyl, ethyl, propyl, and n-butyl, or with a cyclooctane or cycloheptane (e.g., 1-aminocyclooctane-1-carboxylic acid). For example, substitution of position 16 with AIB enhances GLP-1 activity, in the absence of an intramolecular bridge, e.g., a non-covalent intramolecular bridge (e.g., a salt bridge) or a covalent intramolecular bridge (e.g., a lactam). In some embodiments, one, two, three or more of positions 16, 20, 21 or 24 are substituted with AIB. In specific embodiments, one or both of the amino acids corresponding to positions 2, 16, of native human glucagon (SEQ ID NO: 2) are substituted with an alpha, alpha disubstituted amino acid such as AIB.

In accordance with some embodiments, the glucagon analog lacking an intramolecular bridge comprises one or more substitutions within amino acid positions 12-29 with an α,α-disubstituted amino acid and an acyl or alkyl group covalently attached to the side chain of the amino acid at position 10 of the glucagon analog. In specific embodiments, the acyl or alkyl group is not naturally occurring on an amino acid. In certain aspects, the acyl or alkyl group is non-native to the amino acid at position 10. Such acylated or alkylated glucagon peptides lacking an intramolecular bridge exhibit enhanced activity at the GLP-1 and glucagon receptors as compared to the non-acylated counterpart peptides. Further enhancement in activity at the GLP-1 and glucagon receptors can be achieved by the acylated glucagon peptides lacking an intramolecular bridge by incorporating a spacer between the acyl or alkyl group and the side chain of the amino acid at position 10 of the analog. Acylation and alkylation, with or without incorporating spacers, are further described herein.

Alpha Helix: Intramolecular Bridges

In some embodiments, the alpha helix promoting amino acid is an amino acid which is linked to another amino acid of the glucagon analog via an intramolecular bridge. In such embodiments, each of these two amino acids linked via an intramolecular bridge is considered an alpha helix promoting amino acid. In some embodiments, the glucagon analog comprises one or two intramolecular bridges. In some specific embodiments, the glucagon analog comprises one intramolecular bridge in combination with at least one other alpha helix promoting amino acid, e.g., an alpha, alpha-disubstituted amino acid.

In some embodiments, the intramolecular bridge is a bridge which connects two parts of the glucagon analog via noncovalent bonds, including, for example, van der Waals interactions, hydrogen bonds, ionic bonds, hydrophobic interactions, dipole-dipole interactions, and the like. In this regard, the glucagon analog in certain aspects comprises a non-covalent intramolecular bridge. In some embodiments, the non-covalent intramolecular bridge is a salt bridge.

In some embodiments, the intramolecular bridge is a bridge which connects two parts of the analog via covalent bonds. In this regard, the glucagon analog in certain aspects comprises a covalent intramolecular bridge.

In some embodiments, the intramolecular bridge (e.g., non-covalent intramolecular bridge, covalent intramolecular bridge) is formed between two amino acids that are 3 amino acids apart, e.g., amino acids at positions i and i+4, wherein i is any integer between 12 and 25 (e.g., 12, 13, 14, 15, 16, 17, 18, 19, 20, 21, 22, 23, 24, and 25). More particularly, the side chains of the amino acid pairs 12 and 16, 16 and 20, 20 and 24 or 24 and 28 (amino acid pairs in which i=12, 16, 20, or 24) are linked to one another and thus stabilize the glucagon alpha helix. Alternatively, i can be 17. In some specific embodiments, the glucagon analog comprises an intramolecular bridge between amino acids 17 and 21. In some specific embodiments, the glucagon analog comprises an intramolecular bridge between the amino acids at positions 16 and 20 or 12 and 16 and a second intramolecular bridge between the amino acids at positions 17 and 21. Glucagon analogs comprising one or more intramolecular bridges are contemplated herein. In specific embodiments, wherein the amino acids at positions i and i+4 are joined by an intramolecular bridge, the size of the linker is about 8 atoms, or about 7-9 atoms.

In other embodiments, the intramolecular bridge is formed between two amino acids that are two amino acids apart, e.g., amino acids at positions j and j+3, wherein j is any integer between 12 and 26 (e.g., 12, 13, 14, 15, 16, 17, 18, 19, 20, 21, 22, 23, 24, 25, and 26). In some specific embodiments, j is 17. In specific embodiments, wherein amino acids at positions j and j+3 are joined by an intramolecular bridge, the size of the linker is about 6 atoms, or about 5 to 7 atoms.

In yet other embodiments, the intramolecular bridge is formed between two amino acids that are 6 amino acids apart, e.g., amino acids at positions k and k+7, wherein k is any integer between 12 and 22 (e.g., 12, 13, 14, 15, 16, 17, 18, 19, 20, 21, and 22). In some specific embodiments, k is 12, 13, or 17. In an exemplary embodiment, k is 17.

Alpha Helix: Amino Acids Involved in Intramolecular Bridges

Examples of amino acid pairings that are capable of bonding (covalently or non-covalently) to form a six-atom linking bridge include Orn and Asp, Glu and an amino acid of Formula I, wherein n is 2, and homoglutamic acid and an amino acid of Formula I, wherein n is 1, wherein Formula I is:

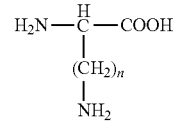

[Formula I]

wherein $n$ = 1 to 4

Examples of amino acid pairings that are capable of bonding to form a seven-atom linking bridge include Orn-Glu (lactam ring); Lys-Asp (lactam); or Homoser-Homoglu (lactone). Examples of amino acid pairings that may form an eight-atom linker include Lys-Glu (lactam); Homolys-Asp (lactam); Orn-Homoglu (lactam); 4-aminoPhe-Asp (lactam); or Tyr-Asp (lactone). Examples of amino acid pairings that may form a nine-atom linker include Homolys-Glu (lactam); Lys-Homoglu (lactam); 4-aminoPhe-Glu (lactam); or Tyr-Glu (lactone). Any of the side chains on these amino acids may additionally be substituted with additional chemical groups, so long as the three-dimensional structure of the alpha-helix is not disrupted. One of ordinary skill in the art can envision alternative pairings or alternative amino acid analogs, including chemically modified derivatives, that would create a stabilizing structure of similar size and desired effect. For example, a homocysteine-homocysteine disulfide bridge is 6 atoms in length and may be further modified to provide the desired effect.

Even without covalent linkage, the amino acid pairings described above (or similar pairings that one of ordinary skill in the art can envision) may also provide added stability to the alpha-helix through non-covalent bonds, for example, through formation of salt bridges or hydrogen-bonding interactions. Accordingly, salt bridges may be formed between: Orn and Glu; Lys and Asp; Homo-serine and Homo-glutamate; Lys and Glu; Asp and Arg; Homo-Lys and Asp; Orn and Homo-Glutamate; 4-aminoPhe and Asp; Tyr and Asp; Homo-Lys and Glu; Lys and Homo-Glu; 4-aminoPhe and Glu; or Tyr and Glu. In some embodiments, the analog comprises a salt bridge between any of the following pairs of amino acids: Orn and Glu; Lys and Asp; Lys and Glu; Asp and Arg; Homo-Lys and Asp; Orn and Homo-Glutamate; Homo-Lys and Glu; and Lys and Homo-Glu. Salt bridges may be formed between other pairs of oppositely charged side chains. See, e.g., Kallenbach et al., *Role of the Peptide Bond in Protein Structure and Folding*, in The Amide Linkage: Structural Significance in Chemistry, Biochemistry, and Materials Science, John Wiley & Sons, Inc. (2000).

In some embodiments, the non-covalent intramolecular bridge is a hydrophobic bridge. In accordance with one embodiment, the alpha helix of the analog is stabilized through the incorporation of hydrophobic amino acids at positions j and j+3 or i and i+4. For instance, i can be Tyr and i+4 can be either Val or Leu; i can be Phe and i+4 can be Met; or i can be Phe and i+4 can be Ile. It should be understood that, for purposes herein, the above amino acid pairings can be reversed, such that the indicated amino acid at position i could alternatively be located at i+4, while the i+4 amino acid can be located at the i position. It should also be understood that suitable amino acid pairings can be formed for j and j+3.

Alpha Helix: Covalent Intramolecular Bridge

In some embodiments, the covalent intramolecular bridge is a lactam ring or lactam bridge. The size of the lactam ring can vary depending on the length of the amino acid side chains, and in one embodiment the lactam is formed by linking the side chains of an ornithine to a aspartic acid side chain. Lactam bridges and methods of making the same are known in the art. See, for example, Houston, Jr., et al., *J Peptide Sci* 1: 274-282 (2004), and Example 1 herein. In some embodiments, the analog comprises a modified sequence of SEQ ID NO: 2 and a lactam bridge between i and i+4, wherein i is as defined herein above. In some embodiments, the glucagon analog comprises two lactam bridges: one between the amino acids at positions 16 and 20 and another between the amino acids at positions 17 and 21. In some embodiments, the glucagon analog comprises one lactam bridge and one salt bridge. Further exemplary embodiments, are described herein in the section entitled "EXAMPLES." Further exemplary embodiments include the following pairings, optionally with a lactam bridge: Glu at position 12 with Lys at position 16; native Lys at position 12 with Glu at position 16; Glu at position 16 with Lys at position 20; Lys at position 16 with Glu at position 20; Glu at position 20 with Lys at position 24; Lys at position 20 with Glu at position 24; Glu at position 24 with Lys at position 28; Lys at position 24 with Glu at position 28.

In some embodiments, the covalent intramolecular bridge is a lactone. Suitable methods of making a lactone bridge are known in the art. See, for example, Sheehan et al., *J Am Chem Soc* 95: 875-879 (1973).

In some aspects, olefin metathesis is used to cross-link one or two turns of the alpha helix of the analog using an all-hydrocarbon cross-linking system. The glucagon analog in this instance comprises α-methylated amino acids bearing olefinic side chains of varying length and configured with either R or S stereochemistry at the j and j+3 or i and i+4 positions. In some embodiments, the olefinic side comprises $(CH_2)n$, wherein n is any integer between 1 to 6. In some embodiments, n is 3 for a cross-link length of 8 atoms. In some embodiments, n is 2 for a cross-link length of 6 atoms. An exemplary glucagon analog comprising an olefinic cross-link is described herein as SEQ ID NO: 17. Suitable methods of forming such intramolecular bridges are described in the art. See, for example, Schafineister et al., *J. Am. Chem. Soc.* 122: 5891-5892 (2000) and Walensky et al., *Science* 305: 1466-1470 (2004). In alternative embodiments, the analog comprises O-allyl Ser residues located on adjacent helical turns, which are bridged together via ruthenium-catalyzed ring closing metathesis. Such procedures of cross-linking are described in, for example, Blackwell et al., *Angew, Chem., Int. Ed.* 37: 3281-3284 (1998).

In specific aspects, use of the unnatural thio-dialanine amino acid, lanthionine, which has been widely adopted as a peptidomimetic of cystine, is used to cross-link one turn of the alpha helix. Suitable methods of lanthionine-based cyclization are known in the art. See, for instance, Matteucci et al., *Tetrahedron Letters* 45: 1399-1401 (2004); Mayer et al., *J. Peptide Res.* 51: 432-436 (1998); Polinsky et al., *J. Med. Chem.* 35: 4185-4194 (1992); Osapay et al., *J. Med. Chem.* 40: 2241-2251 (1997); Fukase et al., *Bull. Chem. Soc. Jpn.* 65: 2227-2240 (1992); Harpp et al., *J. Org. Chem.* 36: 73-80 (1971); Goodman and Shao, *Pure Appl. Chem.* 68: 1303-1308 (1996); and Osapay and Goodman, *J. Chem. Soc. Chem. Commun.* 1599-1600 (1993).

In some embodiments, α,ω-diaminoalkane tethers, e.g., 1,4-diaminopropane and 1,5-diaminopentane) between two Glu residues at positions i and i+7 are used to stabilize the alpha helix of the analog. Such tethers lead to the formation of a bridge 9-atoms or more in length, depending on the length of the diaminoalkane tether. Suitable methods of producing peptides cross-linked with such tethers are described in the art. See, for example, Phelan et al., J. Am. Chem. Soc. 119: 455-460 (1997).

In yet other embodiments, a disulfide bridge is used to cross-link one or two turns of the alpha helix of the analog. Alternatively, a modified disulfide bridge in which one or both sulfur atoms are replaced by a methylene group resulting in an isosteric macrocyclization is used to stabilize the alpha helix of the analog. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

In yet other embodiments, the alpha helix of the analog is stabilized via the binding of metal atom by two His residues or a His and Cys pair positioned at j and j+3, or i and i+4. The metal atom can be, for example, Ru(III), Cu(II), Zn(II), or Cd(II). Such methods of metal binding-based alpha helix stabilization are known in the art. See, for example, Andrews and Tabor, *Tetrahedron* 55: 11711-11743 (1999); Ghadiri et al., *J. Am. Chem. Soc.* 112: 1630-1632 (1990); and Ghadiri et al., *J. Am. Chem. Soc.* 119: 9063-9064 (1997).

The alpha helix of the analog can alternatively be stabilized through other means of peptide cyclizing, which means are reviewed in Davies, J. Peptide. Sci. 9: 471-501 (2003). The alpha helix can be stabilized via the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof.

DPP-IV Resistant Peptides

In some embodiments, the glucagon analog comprises an amino acid substitution at position 1 or 2, or at both positions 1 and 2, in which the amino acid at this position of native human glucagon (SEQ ID NO: 2) is replaced with an amino acid which achieves resistance of the glucagon analog to dipeptidyl peptidase IV (DPP IV) cleavage. In some embodiments, the glucagon analog comprises a modified SEQ ID NO: 2 in which the amino acid at position 1 of SEQ ID NO: 2 (His) is replaced with D-histidine, desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA). In some embodiments, the glucagon analog comprises a modified SEQ ID NO: 2 in which the Ser at position 2 is replaced with D-serine, D-alanine, valine, glycine, N-methyl serine, N-methyl alanine, or alpha, aminoisobutyric acid. In some embodiments, the glucagon analog comprises at position 2 an amino acid which achieves resistance of the glucagon analog to DPP IV and the amino acid which achieves resistance of the glucagon analog to DPP IV is not D-serine.

In some aspects, the glucagon analog comprising an amino acid which achieves resistance of the glucagon analog to DPP IV further comprises an amino acid modification which stabilizes the alpha helix found in the C-terminal portion of glucagon, e.g., through a covalent bond between amino acids at positions "i" and "i+4", e.g., 12 and 16, 16 and 20, or and 24. In some embodiments, this covalent bond is a lactam bridge between a glutamic acid at position 16 and a lysine at position 20. In some embodiments, this covalent bond is an intramolecular bridge other than a lactam bridge. For example, suitable covalent bonding methods include any one or more of olefin metathesis, lanthionine-based cyclization, disulfide bridge or modified sulfur-containing bridge formation, the use of α, ω-diaminoalkane tethers, the formation of metal-atom bridges, and other means of peptide cyclization.

Modification of Position 1

In some specific embodiments, the glucagon analog comprises (a) an amino acid substitution of His at position 1 with a large, aromatic amino acid and (b) an intramolecular bridge that stabilizes that alpha-helix in the C-terminal portion of the molecule (e.g., around positions 12-29). In specific embodiments, the amino acid at position 1 is replaced with Tyr, Phe, Trp, amino-Phe, nitro-Phe, chloro-Phe, sulfo-Phe, 4-pyridyl-Ala, methyl-Tyr, or 3-amino Tyr. The intramolecular bridge, in some embodiments, is any of those described herein. In some aspects, the intramolecular bridge is between the side chains of two amino acids that are separated by three intervening amino acids, i.e., between the side chains of amino acids i and i+4. In some embodiments, the intramolecular bridge is a lactam bridge. In some embodiments, the glucagon analog comprises a large, aromatic amino acid at position 1 and a lactam bridge between the amino acids at positions 16 and 20 of the analog. Such a glucagon analog in some aspects further comprises one or more (e.g., two, three, four, five or more) of the other modifications described herein. For example, the glucagon analog can comprise an amide in place of the C-terminal carboxylate. Also, in some embodiments, such glucagon analogs further comprise one or more of a large aliphatic amino acid at position 17, an imidazole containing amino acid at position 18, and a positive-charged amino acid at position 19. In some embodiments, the glucagon analogs comprising a modification at position 1 and an intramolecular bridge further comprises the amino acid sequence Ile-His-Gln at positions 17-19. Such modifications can be made without destroying activity of the glucagon analog at the GLP-1 receptor and the glucagon receptor. In some embodiments, the glucagon analog additionally comprises an acylated or alkylated amino acid residue.

Modification of Position 3

In some embodiments, the third amino acid of SEQ ID NO: 2 (Gln3) is substituted with an acidic, basic, or hydrophobic amino acid residue and such modification causes the glucagon receptor activity to be reduced. In some embodiments, the acidic, basic, or hydrophobic amino acid is glutamic acid, ornithine, norleucine. In some aspects, modification with one of these residues has led the glucagon analog to exhibit a substantially reduced or destroyed glucagon receptor activity. The glucagon analogs that are substituted with, for example, glutamic acid, ornithine, or norleucine in some aspects have about 10% or less of the activity of native glucagon at the glucagon receptor, e.g., about 1-10%, or about 0.1-10%, or greater than about 0.1% but less than about 10%, while exhibiting at least 20% of the activity of GLP-1 at the GLP-1 receptor. In some embodiments, the glucagon analogs exhibit about 0.5%, about 1% or about 7% of the activity of native glucagon, while exhibiting at least 20% of the activity of GLP-1 at the GLP-1 receptor.

In some embodiments, the glutamine at position 3 of SEQ ID NO: 2 of the glucagon analog is substituted with a glutamine analog without a substantial loss of activity at the glucagon receptor, and in some cases, with an enhancement of glucagon receptor activity. In some embodiments, the glutamine analog is a naturally occurring or a non-naturally occurring or non-coded amino acid comprising a side chain of Structure I, II or III:

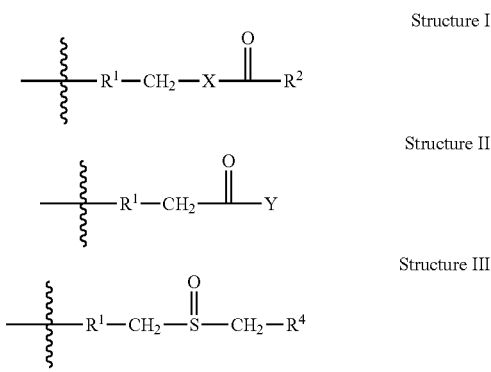

wherein $R^1$ is $C_{0-3}$ alkyl or $C_{0-3}$ heteroalkyl; $R^2$ is $NHR^4$ or $C_{1-3}$ alkyl; $R^3$ is $C_{1-3}$ alkyl; $R^4$ is H or $C_{1-3}$ alkyl; X is NH, O, or S; and Y is $NHR^4$, $SR^3$, or $OR^3$. In some embodiments, X is NH or Y is $NHR^4$. In some embodiments, $R^1$ is $C_{0-2}$ alkyl or $C_1$ heteroalkyl. In some embodiments, $R^2$ is $NHR^4$ or $C_1$ alkyl. In some embodiments, $R^4$ is H or $C^1$ alkyl. In exemplary embodiments, an amino acid comprising a side chain of Structure I is provided where, $R^1$ is $CH_2$—S, X is NH, and $R^2$ is $CH_3$ (acetamidomethyl-cysteine, C(Acm)); $R^1$ is $CH_2$, X is NH, and $R^2$ is $CH_3$ (acetyldiaminobutanoic acid, Dab(Ac)); $R^1$ is $C_0$ alkyl, X is NH, $R^2$ is $NHR^4$, and $R^4$ is H (carbamoyl-diaminopropanoic acid, Dap(urea)); or $R^1$ is $CH_2$—$CH_2$, X is NH, and $R^2$ is $CH_3$ (acetylornithine, Orn(Ac)). In exemplary embodiments, an amino acid comprising a side chain of Structure II is provide where, $R^1$ is $CH_2$, Y is $NHR^4$, and $R^4$ is $CH_3$ (methylglutamine, Q(Me)); In exemplary embodiments, an amino acid comprising a side chain of Structure III is provided where, $R^1$ is $CH_2$ and $R^4$ is H (methionine-sulfoxide, M(O)); In specific embodiments, the amino acid at position 3 is substituted with Dab(Ac) For example, glucagon agonists can comprise a modified amino acid sequence of SEQ ID NO: 595, SEQ ID NO: 601 SEQ ID NO: 603, SEQ ID NO: 604, SEQ ID NO: 605, and SEQ ID NO: 606 of the sequence listing of International Patent Application No. PCT/US2009/047438, filed on Jun. 16, 2009, which is incorporated by reference in its entirety, wherein these amino acid sequences are modified as further described herein, e.g., modified to comprise at least three alpha helix promoting amino acids, modified to comprise (i) an acylated or alkylated amino acid at position 10, (ii) an alpha helix promoting amino acid at position 16, (iii) an aliphatic amino acid at position 17 and/or 18, and (iv) at least one charged amino acid located C-terminal to position 27, and, optionally, further modifications; modified to comprise at least three amino acids of the amino acids 18-24 of Exendin-4 (SEQ ID NO: 8) at the corresponding positions of the glucaogon analog.

Modification of Position 7

In some embodiments, the glucagon analog comprises a modified SEQ ID NO: 2 with an amino acid modification at position 7. In some aspects, the amino acid at position 7 of SEQ ID NO: 2 (Thr) is substituted with a large, aliphatic amino acid, e.g., Ile, Leu, Ala, and the like. Such modifications are believed to drastically reduce activity at the GLP-1 receptor of the glucagon analog.

Modification of Position 15

In some embodiments, the glucagon analogs comprise a modified SEQ ID NO: 2 with an amino acid modification at position 15 which improves stability. In some aspects, the amino acid at position 15 of SEQ ID NO: 2 is deleted or substituted with glutamic acid, homoglutamic acid, cysteic acid or homocysteic acid. Such modifications reduce degradation or cleavage of the analog over time, especially in acidic or alkaline buffers, e.g., buffers at a pH within the range of 5.5 to 8. In some embodiments, the glucagon analogs comprising this modification retains at least 75%, 80%, 90%, 95%, 96%, 97%, 98% or 99% of the original analog after 24 hours at 25° C.

Modification of Position 16

In accordance with one embodiment, analogs of glucagon are provided that have enhanced potency and optionally improved solubility and stability. In one embodiment, enhanced glucagon and GLP-1 potency is provided by an amino acid modification at position 16 of native glucagon (SEQ ID NO: 2). By way of nonlimiting example, such enhanced potency can be provided by substituting the naturally occurring serine at position 16 with glutamic acid or with another negative-charged amino acid having a side chain with a length of 4 atoms, or alternatively with any one of glutamine, homoglutamic acid, or homocysteic acid, or a charged amino acid having a side chain containing at least one heteroatom, (e.g., N, O, S, P) and with a side chain length of about 4 (or 3-5) atoms. In some embodiments, the glucagon analog comprises a modified SEQ ID NO: 2 comprising a substitution of the Ser at position 16 with an amino acid selected from the group consisting of glutamic acid, glutamine, homoglutamic acid, homocysteic acid, threonine or glycine. In some aspects, the serine residue at position 16 is substituted with an amino acid selected from the group consisting of glutamic acid, glutamine, homoglutamic acid and homocysteic acid. In some specific aspects, the serine residue at position 16 is substituted with glutamic acid or a conservative substitution thereof (e.g. an Exendin-4 amino acid).

In alternative embodiments, the glucagon analog comprises a modified sequence of SEQ ID NO: 2 modified by a substitution of Ser at position 16 with Thr or AIB or another alpha helix promoting amino acid as described above. In some embodiments, the alpha helix promoting amino acid forms a non-covalent intramolecular bridge with an amino acid at j+3 or i+4.

Modification at Positions 17-18

In some embodiments, the glucagon analog comprises a modified SEQ ID NO: 2 in which the dibasic Arg-Arg site at positions 17 and 18 is eliminated. Without being bound to any particular theory, it is believed that elimination of the dibasic site in some embodiments improves the in vivo efficacy of the glucagon analog. In some aspects, the glucagon analog is modified in this regard by substituting one or both of the amino acids at positions 17 and 18 of SEQ ID NO: 2 with an amino acid which is not basic, e.g., with an aliphatic amino acid. In some embodiments, one of the amino acids at position 17 or 18 is deleted or an amino acid is inserted in between positions 17 and 18. In some embodiments, the Arg at position 17 is substituted with another amino acid as described herein, e.g., an amino acid comprising a hydrophilic moiety, an alpha helix promoting amino acid. In some embodiments, the alpha helix promoting amino acid forms a non-covalent intramolecular bridge with an amino acid at j+3 or i+4. In some embodiments, the Arg at position 18 is substituted with another amino acid as described herein. In some aspects, the amino acid at position 18 is a small aliphatic amino acid, e.g., Ala. In some specific aspects, the amino acid at position 18 is a small aliphatic amino acid, e.g., Ala, and the Arg at position 17 remains unmodified.

In some embodiments, positions 17 and/or 18 are modified by substitution with corresponding amino acids from Exendin-4, e.g. glutamic acid at position 17 (optionally paired with a positive charged amino acid at position 21), or a conservative substitution thereof, and/or alanine at position 18 or a conservative substitution thereof.

Modification of Position 20

Enhanced activity at the GLP-1 receptor is also provided by an amino acid modification at position 20. In some embodiments, the glutamine at position 20 is replaced with an alpha helix promoting amino acid, e.g. as described above. In some embodiments, the alpha helix promoting amino acid forms a non-covalent intramolecular bridge with an amino acid at j-3 or i-4. In some specific embodiments the amino acid is a hydrophilic amino acid having a side chain that is either charged or has an ability to hydrogen-bond, and is at least about 5 (or about 4-6) atoms in length, for example, lysine, citrulline, arginine, or ornithine, and optionally forms a salt bridge with another alpha helix promiting amino acid at position 16, e.g. a negative charged amino acid. Such modifications in some particular aspects reduce degradation that occurs through deamidation of Gln and in some embodiments, increase the activity of the glucagon analog at the GLP-1 receptor.

Modification at Positions 21-24

In some embodiments, position 21 is modified by substitution with an alpha helix promoting amino acid. In some embodiments, the alpha helix promoting amino acid forms a non-covalent intramolecular bridge with an amino acid at j-3 or i-4.

In some embodiments, positions 21 and/or 23 and/or 24 are modified by substitution with corresponding amino acids from Exendin-4, e.g. the amino acid at position 21 (Asp) is substituted with the amino acid at position 21 of Exendin-4 (SEQ ID NO: 8) (Leu or a conservative amino acid substitution thereof), the amino acid at position 23 (Val) is substituted with the amino acid at position 23 of Exendin-4 (SEQ ID NO: 8) (Ile or a conservative amino acid substitution thereof), the amino acid at position 24 (Gln) is substituted with the amino acid at position 24 of Exendin-4 (SEQ ID NO: 8) (Glu or a conservative amino acid substitution thereof), or combinations thereof.

Charged C-terminus

In some embodiments, the glucagon analog is modified by amino acid substitutions and/or additions that introduce a charged amino acid into the C-terminal portion of the analog.

In some embodiments, such modifications enhance stability and solubility. As used herein the term "charged amino acid" or "charged residue" refers to an amino acid that comprises a side chain that is negative-charged (i.e., de-protonated) or positive-charged (i.e., protonated) in aqueous solution at physiological pH. In some aspects, these amino acid substitutions and/or additions that introduce a charged amino acid modifications are at a position C-terminal to position 27 of SEQ ID NO: 2. In some embodiments, one, two or three (and in some instances, more than three) charged amino acids are introduced within the C-terminal portion (e.g., position(s) C-terminal to position 27). In accordance with some embodiments, the native amino acid(s) at positions 28 and/or 29 are substituted with a charged amino acids, and/or in a further embodiment one to three charged amino acids are also added to the C-terminus of the analog. In exemplary embodiments, one, two or all of the charged amino acids are negative-charged. The negative-charged amino acid in some embodiments is aspartic acid, glutamic acid, cysteic acid, homocysteic acid, or homoglutamic acid. In some aspects, these modifications increase solubility, e.g., provide at least 2-fold, 5-fold, 10-fold, 15-fold, 25-fold, 30-fold or greater solubility relative to native glucagon at a given pH between about 5.5 and 8, e.g., pH 7, when measured after 24 hours at 25° C.

C-Terminal Truncation

In accordance with some embodiments, the glucagon analogs disclosed herein are modified by truncation of the C-terminus by one or two amino acid residues. Such modified glucagon peptides, as shown herein, retain similar activity and potency at the glucagon receptor and GLP-1 receptor. In this regard, the glucagon peptides can comprise amino acids 1-27 or 1-28 of the native glucagon analog (SEQ ID NO: 2), optionally with any of the additional modifications described herein.

Charge-Neutral C-Terminus

In some embodiments, the glucagon analog comprises a modified SEQ ID NO: 2 in which the carboxylic acid of the C-terminal amino acid is replaced with a charge-neutral group, such as an amide or ester. Without being bound to any particular theory, such modifications in certain aspects increases activity of the glucagon analog at the GLP-1 receptor. Accordingly, in some embodiments, the glucagon analog is an amidated peptide, such that the C-terminal residue comprises an amide in place of the alpha carboxylate of an amino acid. As used herein a general reference to a peptide or analog is intended to encompass peptides that have a modified amino terminus, carboxy terminus, or both amino and carboxy termini. For example, an amino acid chain composing an amide group in place of the terminal carboxylic acid is intended to be encompassed by an amino acid sequence designating the standard amino acids.

Other Modifications

In some embodiments, the glucagon analogs additionally or alternatively comprise the following amino acid modifications:

(i) Substitution of Ser at position 2 with Ala;
(ii) Substitution of Tyr at position 10 with Val or Phe, or Trp;
(iii) Substitution of Lys at position 12 with Arg;
(iv) Substitution of Arg at position 17 with Gln or a small aliphatic amino acid, e.g., Ala, or a large aliphatic amino acid, e.g., Ile;
(v) Substitution of Arg at position 18 with a small aliphatic amino acid, e.g., Ala; or an imidazole-containing amino acid, e.g., His;
(vi) Substitution of Ala at position 19 with a positive-charged amino acid, e.g., Gln;
(vii) Substitution of Val at position 23 with Ile, and
(viii) Substitution of Thr at position 29 with Gly or Gln.

In some embodiments, the stability of the glucagon analog is increased by modification of the methionine at position 27, for example, by substitution with leucine or norleucine. Such modifications can reduce oxidative degradation. Stability can also be increased by modification of the Gln at position 20 or 24 or 28, e.g., by substitution with Ala, Ser, Thr, or AIB. Such modifications can reduce degradation that occurs through deamidation of Gln. Stability can be increased by modification of Asp at position 21, e.g., by substitution with another acidic residue, e.g., Glu. Such modifications can reduce degradation that occurs through dehydration of Asp to form a cyclic succinimide intermediate followed by isomerization to iso-aspartate.

In some embodiments, the glucagon analogs described herein are glycosylated, amidated, carboxylated, phosphorylated, esterified, N-acylated, cyclized via, e.g., a disulfide bridge, or converted into a salt (e.g., an acid addition salt, a basic addition salt), and/or optionally dimerized, multimerized, or polymerized, or conjugated.

Any of the modifications described herein, including, for example, the modifications which increase or decrease glucagon receptor activity and which increase GLP-1 receptor activity, can be applied individually or in combination. Combinations of the modifications that increase GLP-1 receptor activity may provide higher GLP-1 activity than any of such modifications taken alone.

EXEMPLARY EMBODIMENTS

Glucagon Analogs with at least one alpha helix promoting amino acid and modifications at positions 17-18

In some embodiments, the glucagon analog comprises a modified amino acid sequence of native human glucagon (SEQ ID NO: 2) comprising the following amino acid modifications: (i) optionally, a substitution of the amino acid at position 10 of SEQ ID NO: 2 with an acylated or alkylated amino acid residue (e.g., a non-coded amino acid comprising an acyl or alkyl group, e.g., a C4 to C30 acyl or alkyl group), (ii) substitution of the amino acid at position 16 of SEQ ID NO: 2 with an alpha helix promoting amino acid, (iii) an amino acid modification at positions 17 and/or 18 of SEQ ID NO: 2, and (iv) one or more charged amino acids C-terminal to position 27 (e.g., a negative-charged residue).

In some embodiments, at least one of the Arg residues at positions 17 and 18 is substituted with an aliphatic amino acid, e.g., a small aliphatic amino acid. In some embodiments, only one of the Arg residues at positions 17 and 18 is substituted to a residue other than Arg. In some aspects, the Arg at position 18 is substituted with a small aliphatic amino acid. In some aspects, the small aliphatic residue in some aspects is an amino acid comprising a straight, unbranched chain of up to 4 carbon atoms. In some specific aspects, the small aliphatic amino acid is Gly or Ala. In specific embodiments, the Arg at position 18 is substituted with Ala.

The incorporation of one or more charged amino acids C-terminal to the amino acid at position 27 can be accomplished by the substitution of position 28 or 29 with a charged amino acid or the addition of a charged amino acids after position 28, 29 or at the C-terminus. The charged amino acids at the C-terminus in some embodiments are any of those listed herein at, e.g., Charged C-terminus. In certain aspects, the charged amino acid is a negative-charged amino acid. In some aspects, the negative-charged amino acid is an acidic amino acid residue, e.g., Asp, or Glu, cysteic acid, homoglutamic acid, homocysteic acid. In some aspects, the negative-charged amino acid is located at position 28, 29, 30, or 31 of the glucagon analog, or at a combination of these positions. In some specific embodiments, the glucagon analog comprises an Asp at position 28. In some specific embodiments, the glucagon analog does not have a Lys at position 30.

The alpha helix promoting amino acid at position 16 may be any of those described herein. In some instances, the alpha helix promoting amino acid is an alpha, alpha disubstituted amino acid. For example, in some embodiments, the alpha helix promoting amino acid is an alpha, alpha disubstituted amino acid comprising $R^1$ and $R^2$, each of which is bonded to the alpha carbon, wherein each of $R^1$ and $R^2$ is independently selected from the group consisting of C1-C4 alkyl, optionally substituted with a hydroxyl, amide, thiol, halo, or $R^1$ and $R^2$ together with the alpha carbon to which they are attached form a ring. In some embodiments, the alpha, alpha disubstituted amino acid is AIB.

In alternative embodiments, the alpha helix promoting amino acid at position 16 is one which forms an intramolecular bridge with another amino acid of the glucagon analog. In certain embodiments, the alpha helix promoting amino acid at position 16 forms an intramolecular bridge with the amino acid at position 12 or 20. The intramolecular bridge in some embodiments is a covalent intramolecular bridge, e.g., a lactam, and in some embodiments is a non-covalent intramolecular bridge, e.g., a salt bridge. In certain embodiments, the intramolecular bridge connects the side chains between a Glu and Lys and one of the amino acids at positions 16 and 12 or 20 is a Glu and the other is a Lys.

In some embodiments, the glucagon analog comprises a large aliphatic amino acid at position 27 of the glucagon analog. The large, aliphatic amino acid is in specific aspects is Leu or norleucine.

The glucagon analogs in some embodiments comprise additional amino acid modifications, such as any of those described herein. In some aspects, the glucagon analog comprises an amino acid which achieves DPP-IV resistance, as further described herein. In some embodiments, the glucagon analog comprises an amino acid substitution at position 3, e.g., Gln3Glu. In specific aspects, the glucagon analog comprises a substitution of the amino acid at position 15, e.g., Asp15Glu. In some aspects, the glucagon analog further comprises one or more of: alpha helix promoting amino acid at position 16 (e.g., AIB, Glu), Gln at position 17, Ala at position 18, alpha helix promoting amino acid at position 20 (e.g., Lys), Glu at position 21, Ile at position 23, and Ala or Cys at position 24. In some aspects, the glucagon analog comprises all of these modifications. In some aspects, the amino acid at position 24 is a Cys and the Cys comprises a hydrophilic moiety, e.g., a PEG. In specific aspects, the amino acid at position 24 is Ala or the native amino acid at this position of native glucagon and the glucagon analog does not comprise a hydrophilic moiety. In some aspects, the glucagon analog comprises an acylated or alkylated amino acid and in specific aspects, the acylated or alkylated amino acid is at position 10. In specific aspects, the acylated or alkylated amino acid comprises a spacer which connects the acyl or alkyl group to the glucagon analog (e.g., via the side chain of an amino acid of the glucagon analog). In some aspects, the spacer is an amino acid or a dipeptide, e.g., a spacer comprising one or two acidic amino acid residues. In some embodiments, the glucagon analog comprises a C-terminal extension of 1-21 amino acid residues, as further described herein. In some embodiments, the C-terminal extension comprises one or more of Glu or Gly. In some aspects, the C-terminal extension is selected from the group consisting of: Gly-Glu, Gly, Gly-Gly, Cys, wherein the Cys is optionally conjugated to a heterologous moiety, e.g., a hydrophilic moiety (e.g., PEG). In some embodiments, the C-terminal amino acid of the glucagon analog comprises an amide in place of the alpha carboxylate. In other embodiments, the C-terminal residue of the glucagon analog comprises the alpha carboxylate. In some embodiments, the glucagon analog does not consist of the amino acid sequence of SEQ ID NO: 9 or 10.

Glucagon Analogs with at Least 3 Alpha Helix Promoting Amino Acids

In some embodiments, the glucagon analog comprises a modified amino acid sequence of native human glucagon (SEQ ID NO: 2), wherein at least three amino acids located at any of positions 12 through 29 of SEQ ID NO: 2 are substituted with alpha helix promoting amino acids. In some embodiments, the alpha helix promoting amino acid is any of those described herein. In some embodiments, the alpha helix promoting amino acids are alpha, alpha disubstituted amino acids, e.g., AIB. In some embodiments, the alpha helix promoting amino acids are amino acids that participate in formation of an intramolecular bridge. In some specific aspects, the glucagon analog comprises four alpha helix promoting amino acids which participate in the formation of two intramolecular bridges. In some specific aspects, the glucagon analog comprises three alpha helix promoting amino acids two of which participates in the formation of an intramolecular bridge and one alpha helix promoting amino acid is an alpha, alpha, di-substituted amino acid, e.g., AIB. The intramolecular bridge of these embodiments may be any of those known in the art, including, for example, any of the covalent intramolecular bridges and non-covalent intramolecular bridges described herein. In some embodiments, the intramolecular bridge is a salt bridge. In some embodiments, the intramolecular bridge is a lactam bridge. In certain embodiments, the intramolecular bridge connects the side chains of two amino acids of the glucagon analog which are three amino acids apart, e.g., i and i+4. In particular aspects, i is 12, 16, or 17. The glucagon analog in some aspects comprises a saltbridge, e.g. between the amino acids Lys and Glu.

In some specific embodiments, the glucagon analog comprises a modified amino acid sequence of SEQ ID NO: 2, wherein three or all of the amino acids located positions 16, 17, 20, and 21 of SEQ ID NO: 2 are substituted with alpha helix promoting amino acids. In some embodiments, the glucagon analog comprises an intramolecular bridge which links the side chains of the amino acids at positions 17 and 21. In certain aspects, one of the amino acids at position 17 and 21 is Lys and the other is Glu. In some embodiments, the glucagon analog further comprises one or more alpha helix promoting amino acids, e.g., one or more alpha, alpha disubstituted amino acid, such as any of those described herein. In some aspects, the alpha, alpha disubstituted amino acid comprises $R^1$ and $R^2$, each of which is bonded to the alpha carbon, wherein each of $R^1$ and $R^2$ is independently selected from the group consisting of C1-C4 alkyl, optionally substituted with a hydroxyl, amide, thiol, halo, or $R^1$ and $R^2$ together with the alpha carbon to which they are attached form a ring. In particular aspects, the alpha, alpha disubstituted amino acid is AIB. In some specific aspects, the alpha, alpha disubstituted amino acid is located at position 16 or 20, or at both positions 16 and 20. In alternative embodiments, the glucagon analog comprises an intermolecular bridge, e.g. a non-covalent bridge such as a salt bridge, that links the amino acids at positions 16 and 20 and another intramolecular bridge, e.g. a non-covalent bridge such as a salt bridge, that links the amino acids at positions 17 and 21.

In some embodiments, the glucagon analog comprises further modifications as described below. For example, in specific aspects, the glucagon analog comprising at least three alpha helix promoting amino acids comprises an amino acid which achieves DPP-IV resistance of the glucagon analog, as further described herein. In some aspects, the glucagon analog comprises an acylated or alkylated amino acid and in specific aspects, the acylated or alkylated amino acid is at position 10. In specific aspects, the acylated or alkylated amino acid comprises a spacer which connects the acyl or alkyl group to the glucagon analog (e.g., via the side chain of an amino acid of the glucagon analog). In some aspects, the spacer is an amino acid or a dipeptide, e.g., a spacer comprising one or two acidic amino acid residues. In some aspects, the glucagon analog does not comprise an acylated or alkylated amino acid. In specific aspects, the glucagon analog comprising a small alilphatic amino acid at position 17 or 18. In specific aspects, the glucagon analog comprises an Ala at position 18. In specific aspects, the glucagon analog comprises a modification at position 20 as further described herein. In specific aspects, the glucagon analog is conjugated to a hydrophilic moiety, e.g., a polyethylene glycol, as further described herein. In specific aspects, the hydrophilic moiety is conjugated to the side chain the amino acid at position 24, e.g., a Cys at position 24. In specific aspects, the glucagon analog comprises one more charged amino acids (e.g., negative charged residues (e.g., Asp, Glu)) C-terminal to position 27. In particular embodiments, the glucagon analog comprises an Asp at position 28. In specific aspects, the glucagon analog is not conjugated to a hydrophilic moiety. In some aspects, the amino acid at position 24 is a Cys and the Cys comprises a hydrophilic moiety, e.g., a PEG. In specific aspects, the amino acid at position 24 is Ala or the native amino acid at this position of native glucagon and the glucagon analog does not comprise a hydrophilic moiety. In some embodiments, the glucagon analog comprises a C-terminal extension of 1-21 amino acid residues, as further described herein. In some embodiments, the C-terminal extension comprises the amino acid sequence of SEQ ID NOs: 13-16, and in some aspects, the amino acid at position 29 is Gly. In some embodiments, the C-terminal amino acid of the glucagon analog comprises an amide in place of the alpha carboxylate. In other embodiments, the C-terminal residue of the glucagon analog comprises the alpha carboxylate.

Glucagon/Exendin-4 Chimeras

In some embodiments, the glucagon analog comprises a modified amino acid sequence of SEQ ID NO: 2, wherein at least three (e.g., four, five, six, seven, eight, or all) of the amino acids located at any of positions 16 through 24 of SEQ ID NO: 2 are substituted with the amino acid at the corresponding position of Exendin-4 (SEQ ID NO: 8), or a conservative amino acid substitution thereof. In this regard, in some embodiments, the glucagon analog comprises a modified amino acid sequence of SEQ ID NO: 2, wherein the amino acid at position 16 (Ser) is substituted with the amino acid at position 16 of Exendin-4 (SEQ ID NO: 8) (Glu or a conservative amino acid substitution thereof), the amino acid at position 17 (Arg) is substituted with the amino acid at position 17 of Exendin-4 (SEQ ID NO: 8) (Glu or a conservative amino acid substitution thereof), the amino acid at position 18 (Arg) is substituted with the amino acid at position 18 of Exendin-4 (SEQ ID NO: 8) (Ala or a conservative amino acid substitution thereof), the amino acid at position 19 (Ala) is substituted with the amino acid at position 19 of Exendin-4 (SEQ ID NO: 8) (Val or a conservative amino acid substitution thereof), the amino acid at position 20 (Gln) is substituted with the amino acid at position 20 of Exendin-4 (SEQ ID NO: 8) (Arg or a conservative amino acid substitution thereof), the amino acid at position 21 (Asp) is substituted with the amino acid at position 21 of Exendin-4 (SEQ ID NO: 8) (Leu or a conservative amino acid substitution thereof), the amino acid at position 23 (Val) is substituted with the amino acid at position 23 of Exendin-4 (SEQ ID NO: 8) (Ile or a conservative amino acid substitution thereof), the amino acid at position 24 (Gln) is substituted with the amino acid at position 24 of Exendin-4 (SEQ ID NO: 8) (Glu or a conservative amino acid substitution thereof), or a combination thereof.

In some embodiments, the glucagon analog comprises the amino acid sequence AVRLFIX (SEQ ID NO: 11) as positions 18 through 24 of the analog, or a modified amino acid sequence of SEQ ID NO: 11 comprising conservative amino acid modifications thereof. Accordingly, in some aspects, the glucagon analog comprises a modified amino acid sequence of SEQ ID NO: 2 comprising a small aliphatic amino acid at position 18, an aliphatic amino acid at position 19, a positive-charged amino acid at position 20, a charge-neutral amino acid at position 21, a large alphatic amino acid at position 23, an acidic amino acid or a Cys at position 24.

In some aspects, the glucagon analog further comprises a charged amino acid at each of positions 16 and 17. In specific aspects, the glucagon analog comprises an acidic amino acid at each of positions 16 and 17 or an acidic amino acid at position 16 and a positive-charged amino acid at position 17. Accordingly, the glucagon analog in some aspects comprises the amino acid sequence of $EX_1AVRLFIX_2$ (SEQ ID NO: 12), wherein $X_1$ is E, K, or Q and $X_2$ is E or C. With regard to these glucagon analogs, in some aspects, the glucagon analog does not comprise the amino acid sequence: KRNRNNIA (SEQ ID NO: 13).

In some embodiments, the glucagon analog comprises further modifications as described below. For example, in specific aspects, the glucagon analog wherein at least three (e.g., four, five, six, seven, eight, or all) of the amino acids located at any of positions 16 through 24 of SEQ ID NO: 2 are substituted with the amino acid at the corresponding position of Exendin-4 (SEQ ID NO: 8), or a conservative amino acid substitution thereof, comprises an amino acid which achieves DPP-IV resistance of the glucagon analog, as further described herein. In some aspects, the glucagon analog comprises an acylated or alkylated amino acid and in specific aspects, the acylated or alkylated amino acid is at position 10. In specific aspects, the acylated or alkylated amino acid comprises a spacer which connects the acyl or alkyl group to the glucagon analog (e.g., via the side chain of an amino acid of the glucagon analog). In some aspects, the spacer is an amino acid or a dipeptide, e.g., a spacer comprising one or two acidic amino acid residues. In some aspects, the glucagon analog does not comprise an acylated or alkylated amino acid. In specific aspects, the glucagon analog is conjugated to a hydrophilic moiety, e.g., a polyethylene glycol, as further described herein. In specific aspects, the heterologous moiety is conjugated to the side chain the amino acid at position 24, e.g., a Cys at position 24. In some aspects, the glucagon analog does not comprise a heterologous moiety, e.g., a hydrophilic moiety. In some aspects, the amino acid at position 27 of the glucagon analog is substituted with an amino acid other than Met, e.g., a large aliphatic amino acid, e.g., a Leu, Norleucine. In specific aspects, the glucagon analog comprises one more charged amino acids (e.g., negative charged residues (e.g., Asp, Glu)) C-terminal to position 27. In particular embodiments, the glucagon analog comprises an Asp at position 28. In specific aspects, the glucagon analog is not conjugated to a hydrophilic moiety. In some aspects, the amino acid at position 24 is a Cys and the Cys comprises a hydrophilic moiety, e.g., a PEG. In specific aspects, the amino acid at position 24 is Ala or the native amino acid at this position of native glucagon and the glucagon analog does not comprise a hydrophilic moiety. In some embodiments, the glucagon analog comprises a C-terminal extension of 1-21 amino acid residues, as further described herein. In some embodiments, the C-terminal extension comprises the amino acid sequence of SEQ ID NOs: 13-16, and in some aspects, the amino acid at position 29 is Gly. In some embodiments, the C-terminal amino acid of the glucagon analog comprises an amide in place of the alpha carboxylate. In other embodiments, the C-terminal residue of the glucagon analog comprises the alpha carboxylate.

The following descriptions are applicable to (i) the glucagon analogs with at least one alpha helix promoting amino acid and modifications at positions 17-18 described herein, (ii) the glucagon analogs with at least three alpha helix promoting amino acids described herein, and (iii) the glucagon analogs comprising at least three of the amino acids located at any of positions 16 to 24 substituted with an amino acid at the corresponding position of Exendin-4 (SEQ ID NO: 8), or a conservative substitution thereof.

In some specific aspects, the glucagon analog comprises a modified amino acid sequence of SEQ ID NO: 2 comprising additional amino acid modifications (e.g., up to 7, up to 8, up to 9, up to 10), e.g., conservative substitutions or non-conservative substitutions, that do not destroy glucagon or GLP-1 activity. Any of the amino acid modifications of the present disclosures may be incorporated, including those that provide the glucagon analog with additional desirable properties, e.g., prolonged half life in circulation, delayed onset of action, extended duration of action, improved resistance to proteases such as DPP-IV, increased potency at one or both of the GLP-1 receptor and glucagon receptor, improved stability, enhanced solubility, and the like.

In some aspects, the glucagon analog of any of these three exemplary embodiments comprises an acylated or alkylated amino acid, e.g., in accordance with the disclosures herein. See, e.g., the teachings under Acylation and Alkylation. For example, in some aspects, the acylated or alkylated amino acid is located at position 10. The acylated or alkylated amino acid in some embodiments comprises a spacer between the amino acid at position 10 and the acyl or alkyl group. In some embodiments, the spacer is an amino acid or dipeptide spacer, e.g., a spacer comprising one or more acidic residues.

In some specific aspects, the glucagon analog described herein is conjugated to a heterologous moiety, as further described herein. See, for example, the teachings under CONJUGATES, Conjugate: Fc fusions, Conjugates: hydrophilic moieties, Conjugates: rPEG, and Conjugates: Multimers. Accordingly, the glucagon analog in specific aspects comprises a hydrophilic moiety, e.g., comprises an amino acid covalently linked to a hydrophilic moiety, e.g., a polyethylene glycol (e.g., a 40 kDa PEG). The amino acid comprising a hydrophilic moiety is particular aspects is located at position 24 or at the C-terminus.

In particular aspects, the glucagon analog comprises an amino acid which achieves resistance to DPP-IV proteolytic cleavage, as further described herein. See, e.g., the teachings under DPP-IV Resistant Peptides. Accordingly, in some aspects, the glucagon analog comprises an amino acid modification at position 1 and/or 2 in which the amino acid of SEQ ID NO: 2 at the position is substituted with an amino acid which achieves resistance of the glucagon analog to DPP-IV cleavage. For example, in some embodiments, the Ser at position 2 is substituted with an amino acid selected from the group consisting of: D-serine, D-alanine, valine, glycine, N-methyl serine, N-methyl alanine, or amino isobutyric acid. In some embodiments, the His at position 1 is substituted with one of: D-histidine, desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA).

In some specific aspects, the glucagon analog comprises a C-terminal amide in place of a C-terminal alpha carboxylate and/or may comprise a C-terminal extension, accordance with the disclosures herein. See, e.g., the teachings under Charge-neutral C-terminus and Fusion Peptides, Chimeras, and C-terminal extensions.

Additionally or alternatively, the glucagon analog in some embodiments comprises one or more of the following amino acid modifications: (i) His at position substituted with an amino acid in accordance with the teachings herein under Modification of Position 1; e.g., His1Tyr(ii) Gln at position 3 replaced with an amino acid in accordance with the teachings under Modification of Position 3, e.g., substitution with a glutamine analog or Glu; (iii) Thr at position 7 replaced with a large, aliphatic amino acid, e.g., Ile, Leu, Ala; (iv) Tyr at position 10 replaced with an amino acid in accordance with the teachings herein under Other Modifications, e.g., Tyr10 replaced with Val or Phe or Trp; (v) Lys at position 12 is replaced with an amino acid in accordance with the teachings herein under Other Modifications, e.g., Lys12 replaced with a Arg; (vi) Asp at position 15 is replaced with an amino acid in accordance with the teachings under Modification of Position 15, e.g., Asp15Glu; (vii) Arg at position 17 and/or 18 is modified in accordance with the teachings herein under Modification at positions 17-18, e.g., Arg18Ala; (viii) Gln at position 20 and/or 24 replaced with an amino acid in accordance with the teachings herein under Modifications of Position 20 and Other Modifications; e.g., Gln20 and/or Gln24 replaced with Ala, Ser, Thr, or AIB (viii) Met at position 27 replaced with an amino acid in accordance with the teachings under Other Modifications, e.g., Met27 replaced with Leu or Norleucine; (ix) Asn at position 28 replaced with a negative-charged amino acid in accordance with the teachings under Charged C-terminus, e.g., Asn28Asp; or (x) Thr at position 29 replaced with an amino acid in accordance with the teachings herein under Charged C-terminus and Other Modifications, e.g., Thr29Gly or Thr29 replaced with an negative-charged amino acid.

In some specific embodiments, the glucagon analog additionally or alternatively comprises one or more of the other modifications described herein, including, but not limited to, acylation, alkylation, pegylation, deletion of 1-2 amino acids at the C-terminus, addition of and/or substitution with charged amino acids at the C-terminus, replacement of the C-terminal carboxylate with an amide, addition of a C-terminal extension, and conservative and/or non-conservative amino acid substitutions, such as substitution of Met at position 27 with Leu or Nle, substitution of Asp at position 15 with Glu (or like amino acid), substitution at position 1 and/or 2 with amino acids which achieve DPP-IV protease resistance, substitution of Ser at position 2 with Ala, substitution of Tyr at position 10 with Val or Phe, substitution of Lys at position 12 with Arg, substitution of Ser at position 16 with Thr or AIB, substitution of Gln at position 20 and/or 24 with Asp, Glu, or AIB, substitution of Ser at position 16 with Glu or Thr, Arg at position 18 with Ala, Gln at position 20 with Lys, Asp at position 21 with Glu, and Gln at position 24 with Asn or Cys. In some embodiments, the foregoing glucagon peptide comprises a Gln or Gly at position 29 or addition of a C-terminal extension, e.g., GGPSSGAPPPS (SEQ ID NO: 15)

C-terminal to the amino acid at position 28. In a specific aspect, the glucagon peptide comprises one or more of an amide group in place of the C-terminal carboxylate, an acyl group, e.g., a C16 fatty acid, and a hydrophilic moiety, e.g., a polyethylene glycol (PEG).

The above described glucagon analogs exhibit activity at the glucagon receptor, at the GLP-1 receptor, or at both the glucagon receptor and the GLP-1 receptor. In some embodiments, the glucagon analog exhibits at least or about 3% (e.g., at least or about 5%, at least or about 10%, at least or about 15%, at least or about 20%, at least or about 30%, at least or about 40%, at least or about 50%, at least or about 60%, at least or about 70%, at least or about 80%, at least or about 90%, or at least or about 100% or more) activity of native GLP-1 at the GLP-1 receptor. In some embodiments, the glucagon analog exhibits at least or about 3% (e.g., at least or about 5%, at least or about 10%, at least or about 15%, at least or about 20%, at least or about 30%, at least or about 40%, at least or about 50%, at least or about 60%, at least or about 70%, at least or about 80%, at least or about 90%, or at least or about 100% or more) activity of native glucagon at the glucagon receptor. In specific embodiments, the glucagon analog exhibits at least 100% activity of native glucagon at the glucagon receptor, exhibits at least 100% activity of native GLP-1 at the GLP-1 receptor, or both.

In some embodiments, the glucagon analog has an EC50 at the GLP-1 receptor which is about 50-fold or less (e.g., about 40-fold or less, about 30-fold or less, about 25-fold or less, about 20-fold or less, about 15-fold or less, about 10-fold or less, about 5-fold or less, about 3-fold or less, about 2-fold or less) of the EC50 at the glucagon receptor. In some embodiments, the glucagon analog has an EC50 at the GLP-1 receptor which is two- to ten-fold greater than the EC50 at the glucagon receptor.

Exclusions

In some embodiments, any one of the following peptides is excluded from the glucagon analogs described herein, although any of the following peptides comprising one or more further modifications thereto as described herein exhibiting the desired GLP-1 or co-agonist activity, pharmaceutical compositions, kits, and treatment methods using such compounds may be included in the invention: The peptide of SEQ ID NO: 2 with an [Arg12] substitution and with a C-terminal amide; The peptide of SEQ ID NO: 2 with [Arg12,Lys20] substitutions and with a C-terminal amide; The peptide of SEQ ID NO: 2 with [Arg12,Lys24] substitutions and with a C-terminal amide; The peptide of SEQ ID NO: 2 with [Arg12, Lys29] substitutions and with a C-terminal amide; The peptide of SEQ ID NO: 2 with a [Glu9] substitution; The peptide of SEQ ID NO: 2 missing His1, with [Glu9, Glu16, Lys29] substitutions and C-terminal amide; The peptide of SEQ ID NO: 2 with [Glu9, Glu16, Lys29] substitutions and with a C-terminal amide; The peptide of SEQ ID NO: 2 with [Lys13, Glu17] substitutions linked via lactam bridge and with a C-terminal amide; The peptide of SEQ ID NO: 2 with [Lys17, Glu21] substitutions linked via lactam bridge and with a C-terminal amide; The peptide of SEQ ID NO: 2 missing His1, with [Glu20, Lys24] substitutions linked via lactam bridge. In some embodiments, the glucagon analog is not any of the peptides disclosed in any of International Patent Application No. PCT/US2009/034448, filed on Feb. 19, 2009; International Patent Application No. PCT/US2009/047438, filed on Jun. 16, 2009; and PCT/US2008/053857 (WO 2008/101017), filed on Feb. 13, 2008; each of which are incorporated by reference in their entirety. In some embodiments, the glucagon analog does not include all or part of the sequence KRNRNNIA linked to the C-terminus after position 29, e.g. KRNR.

Methods of Making Peptides

The glucagon analogs of the disclosure can be obtained by methods known in the art. Suitable methods of de novo synthesizing peptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752.

Also, in the instances in which the analogs of the disclosure do not comprise any non-coded or non-natural amino acids, the glucagon analog can be recombinantly produced using a nucleic acid encoding the amino acid sequence of the analog using standard recombinant methods. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994.

In some embodiments, the glucagon analogs of the disclosure are isolated. In some embodiments, the glucagon analogs of the disclosure are purified. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

In some embodiments, the peptides described herein are commercially synthesized by companies, such as Synpep (Dublin, Calif.), Peptide Technologies Corp. (Gaithersburg, Md.), and Multiple Peptide Systems (San Diego, Calif.). In this respect, the peptides can be synthetic, recombinant, isolated, and/or purified.

Conjugates

The invention further provides conjugates comprising one or more of the glucagon analogs described herein conjugated to a heterologous moiety. As used herein, the term "heterologous moiety" is synonymous with the term "conjugate moiety" and refers to any molecule (chemical or biochemical, naturally-occurring or non-coded) which is different from the glucagon analogs described herein. Exemplary conjugate moieties that can be linked to any of the analogs described herein include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments a conjugate is provided comprising an analog of the present invention and a plasma protein, wherein the plasma protein is selected from the group consisting of albumin, transferin, fibrinogen and globulins. In some embodiments the plasma protein moiety of the conjugate is albumin or transferin. The conjugate in some embodiments comprises one or more of the glucagon analogs described herein and one or more of: a peptide (which is distinct from the glucagon and/or GLP-1 receptor active glucagon analogs described herein), a polypeptide, a nucleic acid molecule, an antibody or fragment thereof, a polymer, a quantum dot, a small molecule, a toxin, a diagnostic agent, a carbohydrate, an amino acid.

In some embodiments, the heterologous moiety is a peptide which is distinct from the glucagon and/or GLP-1 receptor active analogs described herein and the conjugate is a fusion peptide or a chimeric peptide. In some embodiments, the heterologous moiety is a peptide extension of 1-21 amino acids. In specific embodiments, the extension is attached to the C-terminus of the glucagon analog, e.g., to amino acid at position 29.

In some specific aspects, the extension is a single amino acid or dipeptide. In specific embodiments, the extension comprises an amino acid selected from the group consisting of: a charged amino acid (e.g., a negative-charged amino acid (e.g., Glu), a positive-charged amino acid), an amino acid comprising a hydrophilic moiety. In some aspects, the extension is Gly, Glu, Cys, Gly-Gly, Gly-Glu.

In some embodiments, the extension comprises an amino acid sequence of SEQ ID NO: 14 (GPSSGAPPPS), SEQ ID NO: 15 (GGPSSGAPPPS), SEQ ID NO: 13 (KRNRNNIA), or SEQ ID NO: 16 (KRNR). In specific aspects, the amino acid sequence is attached through the C-terminal amino acid of the glucagon analog, e.g., amino acid at position 29. In some embodiments, the amino acid sequence of SEQ ID NOs: 13-16 is bound to amino acid 29 of the glucagon analog through a peptide bond. In some specific embodiments, the amino acid at position 29 of the glucagon analog is a Gly and the Gly is fused to one of the amino acid sequences of SEQ ID NOs: 13-16.

In some embodiments, the heterologous moiety is a polymer. In some embodiments, the polymer is selected from the group consisting of: polyamides, polycarbonates, polyalkylenes and derivatives thereof including, polyalkylene glycols, polyalkylene oxides, polyalkylene terephthalates, polymers of acrylic and methacrylic esters, including poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Hydrophilic polymers are further described herein under "Hydrophilic Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

In specific embodiments, the polymer is a polyalkylene glycol, including, for example, polyethylene glycol (PEG).

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In some embodiments, the heterologous moiety is attached via non-covalent or covalent bonding to the analog of the present disclosure. In certain aspects, the heterologous moiety is attached to the analog of the present disclosure via a linker. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The glucagon analog in some embodiments is linked to conjugate moieties via direct covalent linkage by reacting targeted amino acid residues of the analog with an organic derivatizing agent that is capable of reacting with selected side chains or the N- or C-terminal residues of these targeted amino acids. Reactive groups on the analog or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the analog indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues are most commonly reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group.

Another type of covalent modification involves chemically or enzymatically coupling glycosides to the analog. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

In some embodiments, the glucagon analog is conjugated to a heterologous moiety via covalent linkage between a side chain of an amino acid of the glucagon analog and the heterologous moiety. In some embodiments, the glucagon analog is conjugated to a heterologous moiety via the side chain of an amino acid at position 16, 17, 21, 24, or 29, a position within a C-terminal extension, or the C-terminal amino acid, or a combination of these positions. In some aspects, the amino acid covalently linked to a heterologous moiety (e.g., the amino acid comprising a heterologous moiety) is a Cys, Lys, Orn, homo-Cys, or Ac-Phe, and the side chain of the amino acid is covalently bonded to a heterologous moiety.

In some embodiments, the conjugate comprises a linker that joins the glucagon analog to the heterologous moiety. In some aspects, the linker comprises a chain of atoms from 1 to about 60, or 1 to 30 atoms or longer, 2 to 5 atoms, 2 to 10 atoms, 5 to 10 atoms, or to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

Conjugates: Fc Fusions

As noted above, in some embodiments, the analogs are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1 for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J. Immunol. 175:6694-701, 2005). Amino acid residues involved in IgE receptor binding are described in Sayers et al. (J Biol. Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Conjugates: Hydrophilic Moieties

The glucagon analogs described herein can be further modified to improve its solubility and stability in aqueous solutions at physiological pH, while retaining the high biological activity relative to native glucagon. Hydrophilic moieties such as PEG groups can be attached to the analogs under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the analog by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

In specific aspects, an amino acid residue of the analog having a thiol is modified with a hydrophilic moiety such as PEG. In some embodiments, the thiol is modified with maleimide-activated PEG in a Michael addition reaction to result in a PEGylated analog comprising the thioether linkage shown below:

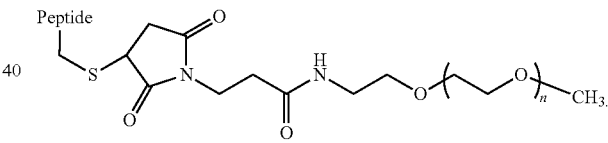

In some embodiments, the thiol is modified with a haloacetyl-activated PEG in a nucleophilic substitution reaction to result in a PEGylated analog comprising the thioether linkage shown below:

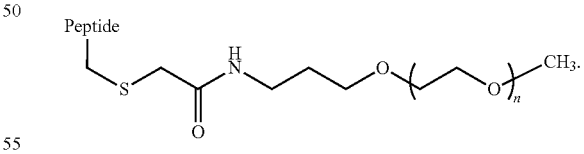

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1, 3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof. Dextrans are polysaccharide polymers of glucose subunits, predominantly linked by α1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD. Linear or branched polymers are contemplated. Resulting preparations of conjugates may be essentially monodisperse or polydisperse, and may have about 0.5, 0.7, 1, 1.2, 1.5 or 2 polymer moieties per analog.

In some embodiments, the glucagon analog is conjugated to a hydrophilic moiety via covalent linkage between a side chain of an amino acid of the glucagon analog and the hydrophilic moiety. In some embodiments, the glucagon analog is conjugated to a hydrophilic moiety via the side chain of an amino acid at position 16, 17, 21, 24, or 29, a position within a C-terminal extension, or the C-terminal amino acid, or a combination of these positions. In some aspects, the amino acid covalently linked to a hydrophilic moiety (e.g., the amino acid comprising a hydrophilic moiety) is a Cys, Lys, Orn, homo-Cys, or Ac-Phe, and the side chain of the amino acid is covalently bonded to a hydrophilic moiety (e.g., PEG).

Conjugates: rPEG

In some embodiments, the conjugate of the present disclosure comprises the analog having glucagon and/or GLP-1 agonist activity fused to an accessory analog which is capable of forming an extended conformation similar to chemical PEG (e.g., a recombinant PEG (rPEG) molecule), such as those described in International Patent Application Publication No. WO2009/023270 and U.S. Patent Application Publication No. US20080286808. The rPEG molecule in some aspects is a polypeptide comprising one or more of glycine, serine, glutamic acid, aspartic acid, alanine, or proline. In some aspects, the rPEG is a homopolymer, e.g., poly-glycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly(Gly-Pro), poly(Ser-Glu), etc. In some aspects, the rPEG comprises three different types of amino acids, e.g., poly(Gly-Ser-Glu). In specific aspects, the rPEG increases the half-life of the Glucagon and/or GLP-1 agonist analog. In some aspects, the rPEG comprises a net positive or net negative charge. The rPEG in some aspects lacks secondary structure. In some embodiments, the rPEG is greater than or equal to 10 amino acids in length and in some embodiments is about 40 to about 50 amino acids in length. The accessory peptide in some aspects is fused to the N- or C-terminus of the analog of the present disclosure through a peptide bond or a proteinase cleavage site, or is inserted into the loops of the analog of the present disclosure. The rPEG in some aspects comprises an affinity tag or is linked to a PEG that is greater than 5 kDa. In some embodiments, the rPEG confers the analog of the present disclosure with an increased hydrodynamic radius, serum half-life, protease resistance, or solubility and in some aspects confers the analog with decreased immunogenicity.

Conjugates: Multimers

The invention further provides multimers or dimers of the analogs disclosed herein, including homo- or hetero-multimers or homo- or hetero-dimers. Two or more of the analogs can be linked together using standard linking agents and procedures known to those skilled in the art. For example, dimers can be formed between two peptides through the use of bifunctional thiol crosslinkers and bi-functional amine crosslinkers, particularly for the analogs that have been substituted with cysteine, lysine ornithine, homocysteine or acetyl phenylalanine residues. The dimer can be a homodimer or alternatively can be a heterodimer. In certain embodiments, the linker connecting the two (or more) analogs is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together.

Pharmaceutical Compositions, Uses and Kits

Salts

In some embodiments, the glucagon analog is in the form of a salt. e.g., a pharmaceutically acceptable salt. As used herein the term "pharmaceutically acceptable salt" refers to salts of compounds that retain the biological activity of the parent compound, and which are not biologically or otherwise undesirable. Such salts can be prepared in situ during the final isolation and purification of the analog, or separately prepared by reacting a free base function with a suitable acid. Many of the compounds disclosed herein are capable of forming acid and/or base salts by virtue of the presence of amino and/or carboxyl groups or groups similar thereto.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenyl-propionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Basic addition salts also can be prepared in situ during the final isolation and purification of the source of salicylic acid, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

Further, basic nitrogen-containing groups can be quaternized with the analog of the present disclosure as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

Formulations

In accordance with some embodiments, a pharmaceutical composition is provided wherein the composition comprises a glucagon analog of the present disclosure, or pharmaceutically acceptable salt thereof, and a pharmaceutically acceptable carrier. The pharmaceutical composition can comprise any pharmaceutically acceptable ingredient, including, for example, acidifying agents, additives, adsorbents, aerosol propellants, air displacement agents, alkalizing agents, anti-caking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

In some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC)chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edetate, disodium edetate, disodium hydrogen phosphate, docusate calcium, docusate potassium, docusate sodium, dodecyl gallate, dodecyltrimethylammonium bromide, edetate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium tri silicate, magnesium tri silicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, postassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capabale of buffering at the desired pH such as, for example, phosphate buffers (e.g., PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g., at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

Routes of Administration

The following discussion on routes of administration is merely provided to illustrate exemplary embodiments and should not be construed as limiting the scope in any way.

Formulations suitable for oral administration can consist of (a) liquid solutions, such as an effective amount of the analog of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the analog of the present disclosure in a flavor, usually sucrose and acacia or tragacanth, as well as pastilles comprising the analog of the present disclosure in an inert base, such as gelatin and glycerin, or sucrose and acacia, emulsions, gels, and the like containing, in addition to, such excipients as are known in the art.

The analogs of the disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the analog is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The analog of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the analog of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the analog of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the analog of the disclosure can be formulated as inclusion complexes, such as cyclodextrin inclusion complexes, or liposomes.

Dose

The analogs of the disclosure are believed to be useful in methods of treating a disease or medical condition in which glucagon receptor agonism, GLP-1 receptor agonism, or Glucagon receptor/GLP-1 receptor co-agonism plays a role. For purposes of the disclosure, the amount or dose of the analog of the present disclosure administered should be sufficient to effect, e.g., a therapeutic or prophylactic response, in the subject or animal over a reasonable time frame. For example, the dose of the analog of the present disclosure should be sufficient to stimulate cAMP secretion from cells as described herein or sufficient to decrease blood glucose levels, fat levels, food intake levels, or body weight of a mammal, in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular analog of the present disclosure and the condition of the animal (e.g., human), as well as the body weight of the animal (e.g., human) to be treated.

Many assays for determining an administered dose are known in the art. For purposes herein, an assay, which comprises comparing the extent to which blood glucose levels are lowered upon administration of a given dose of the analog of the present disclosure to a mammal among a set of mammals of which is each given a different dose of the analog, could be used to determine a starting dose to be administered to a mammal. The extent to which blood glucose levels are lowered upon administration of a certain dose can be assayed by methods known in the art, including, for instance, the methods described herein as Example 6.

The dose of the analog of the present disclosure also will be determined by the existence, nature and extent of any adverse side effects that might accompany the administration of a particular analog of the present disclosure. Typically, the attending physician will decide the dosage of the analog of the present disclosure with which to treat each individual patient, taking into consideration a variety of factors, such as age, body weight, general health, diet, sex, analog of the present disclosure to be administered, route of administration, and the severity of the condition being treated. By way of example and not intending to limit the invention, the dose of the analog of the present disclosure can be about 0.0001 to about 1 g/kg body weight of the subject being treated/day, from about 0.0001 to about 0.001 g/kg body weight/day, or about 0.01 mg to about 1 g/kg body weight/day.

In some embodiments, the pharmaceutical composition comprises any of the analogs disclosed herein at a purity level suitable for administration to a patient. In some embodiments, the analog has a purity level of at least about 90%, about 91%, about 92%, about 93%, about 94%, about 95%, about 96%, about 97%, about 98% or about 99%, and a pharmaceutically acceptable diluent, carrier or excipient. The pharmaceutical composition in some aspects comprise the analog of the present disclosure at a concentration of at least A, wherein A is about 0.001 mg/ml, about 0.01 mg/ml, 0 about 1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml or higher. In some embodiments, the pharmaceutical composition comprises the analog at a concentration of at most B, wherein B is about 30 mg/ml, about 25 mg/ml, about 24 mg/ml, about 23, mg/ml, about 22 mg/ml, about 21 mg/ml, about 20 mg/ml, about 19 mg/ml, about 18 mg/ml, about 17 mg/ml, about 16 mg/ml, about 15 mg/ml, about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or about 0.1 mg/ml. In some embodiments, the compositions may contain an analog at a concentration range of A to B mg/ml, for example, about 0.001 to about 30.0 mg/ml.

Targeted Forms

One of ordinary skill in the art will readily appreciate that the analogs of the disclosure can be modified in any number of ways, such that the therapeutic or prophylactic efficacy of the analog of the present disclosures is increased through the modification. For instance, the analog of the present disclosure can be conjugated either directly or indirectly through a linker to a targeting moiety. The practice of conjugating compounds, e.g., glucagon analogs described herein, to targeting moieties is known in the art. See, for instance, Wadhwa et al., *J Drug Targeting*, 3, 111-127 (1995) and U.S. Pat. No. 5,087, 616. The term "targeting moiety" as used herein, refers to any molecule or agent that specifically recognizes and binds to a cell-surface receptor, such that the targeting moiety directs the delivery of the analog of the present disclosures to a population of cells on which surface the receptor (the glucagon receptor, the GLP-1 receptor) is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups. The term "linker" in some embodiments refers to any agent or molecule that bridges the analog of the present disclosures to the targeting moiety. One of ordinary skill in the art recognizes that sites on the analog of the present disclosures, which are not necessary for the function of the analog of the present disclosures, are ideal sites for attaching a linker and/or a targeting moiety, provided that the linker and/or targeting moiety, once attached to the analog of the present disclosures, do(es) not interfere with the function of the analog of the present disclosures, i.e., the ability to stimulate cAMP secretion from cells, to treat diabetes or obesity.

Controlled Release Formulations

Alternatively, the glucagon analogs described herein can be modified into a depot form, such that the manner in which the analog of the present disclosures is released into the body to which it is administered is controlled with respect to time and location within the body (see, for example, U.S. Pat. No. 4,450,150). Depot forms of analog of the present disclosures can be, for example, an implantable composition comprising the analog of the present disclosures and a porous or non-porous material, such as a polymer, wherein the analog of the present disclosures is encapsulated by or diffused throughout the material and/or degradation of the non-porous material. The depot is then implanted into the desired location within the body and the analog of the present disclosures are released from the implant at a predetermined rate.

The pharmaceutical composition in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374: 46-52 (2009) and International Patent Application Publication Nos. WO 2008/130158, WO2004/033036; WO2000/ 032218; and WO 1999/040942.

The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

Combinations

The glucagon analogs described herein may be administered alone or in combination with other therapeutic agents which aim to treat or prevent any of the diseases or medical conditions described herein. For example, the glucagon analogs described herein may be co-administered with (simultaneously or sequentially) an anti-diabetic or anti-obesity agent. Anti-diabetic agents known in the art or under investigation include insulin, leptin, Peptide YY (PYY), Pancreatic Peptide (PP), fibroblast growth factor 21 (FGF21), Y2Y4 receptor agonists, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; glucokinase activators (GKA);

glucagon receptor antagonists (GRA); or FBPase (fructose 1,6-bisphosphatase) inhibitors.

Anti-obesity agents known in the art or under investigation include appetite suppressants, including phenethylamine type stimulants, phentermine (optionally with fenfluramine or dexfenfluramine), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Qnexa (topiramate and phentermine), Excalia (bupropion and zonisamide) or Contrave (bupropion and naltrexone); or lipase inhibitors, similar to XENICAL (Orlistat) or Cetilistat (also known as ATL-962), or GT 389-255.

The peptides described herein in some embodiments are co-administered with an agent for treatment of non-alcoholic fatty liver disease or NASH. Agents used to treat non-alcoholic fatty liver disease include ursodeoxycholic acid (a.k.a., Actigall, URSO, and Ursodiol), Metformin (Glucophage), rosiglitazone (Avandia), Clofibrate, Gemfibrozil, Polymixin B, and Betaine.

The peptides described herein in some embodiments are co-administered with an agent for treatment of a neurodegenerative disease, e.g., Parkinson's Disease. Anti-Parkinson's Disease agents are furthermore known in the art and include, but not limited to, levodopa, carbidopa, anticholinergics, bromocriptine, pramipexole, and ropinirole, amantadine, and rasagiline.

In view of the foregoing, the invention further provides pharmaceutical compositions and kits additionally comprising one of these other therapeutic agents. The additional therapeutic agent may be administered simultaneously or sequentially with the analog of the present disclosure. In some aspects, the analog is administered before the additional therapeutic agent, while in other aspects, the analog is administered after the additional therapeutic agent.

Uses

Based on the information provided for the first time herein, it is contemplated that the glucagon analogs described herein and related pharmaceutical compositions are useful for treatment of a disease or medical condition, in which e.g., the lack of activity at the glucagon receptor, the GLP-1 receptor, or at both receptors, is a factor in the onset and/or progression of the disease or medical condition. Accordingly, the invention provides a method of treating or preventing a disease or medical condition in a patient, wherein the disease or medical condition is a disease of medical condition in which a lack of GLP-1 receptor activation and/or glucagon receptor activation is associated with the onset and/or progression of the disease of medical condition. The method comprises providing to the patient an analog in accordance with any of those described herein in an amount effective to treat or prevent the disease or medical condition.

In some embodiments, the disease or medical condition is metabolic syndrome. Metabolic Syndrome, also known as metabolic syndrome X, insulin resistance syndrome or Reaven's syndrome, is a disorder that affects over 50 million Americans. Metabolic Syndrome is typically characterized by a clustering of at least three or more of the following risk factors: (1) abdominal obesity (excessive fat tissue in and around the abdomen), (2) atherogenic dyslipidemia (blood fat disorders including high triglycerides, low HDL cholesterol and high LDL cholesterol that enhance the accumulation of plaque in the artery walls), (3) elevated blood pressure, (4) insulin resistance or glucose intolerance, (5) prothrombotic state (e.g., high fibrinogen or plasminogen activator inhibitor-1 in blood), and (6) pro-inflammatory state (e.g., elevated C-reactive protein in blood). Other risk factors may include aging, hormonal imbalance and genetic predisposition.

Metabolic Syndrome is associated with an increased the risk of coronary heart disease and other disorders related to the accumulation of vascular plaque, such as stroke and peripheral vascular disease, referred to as atherosclerotic cardiovascular disease (ASCVD). Patients with Metabolic Syndrome may progress from an insulin resistant state in its early stages to full blown type II diabetes with further increasing risk of ASCVD. Without intending to be bound by any particular theory, the relationship between insulin resistance, Metabolic Syndrome and vascular disease may involve one or more concurrent pathogenic mechanisms including impaired insulin-stimulated vasodilation, insulin resistance-associated reduction in NO availability due to enhanced oxidative stress, and abnormalities in adipocyte-derived hormones such as adiponectin (Lteif and Mather, Can. J. Cardiol. 20 (suppl. B):66B-76B (2004)).

According to the 2001 National Cholesterol Education Program Adult Treatment Panel (ATP III), any three of the following traits in the same individual meet the criteria for Metabolic Syndrome: (a) abdominal obesity (a waist circumference over 102 cm in men and over 88 cm in women); (b) serum triglycerides (150 mg/dl or above); (c) HDL cholesterol (40 mg/dl or lower in men and 50 mg/dl or lower in women); (d) blood pressure (130/85 or more); and (e) fasting blood glucose (110 mg/dl or above). According to the World Health Organization (WHO), an individual having high insulin levels (an elevated fasting blood glucose or an elevated post meal glucose alone) with at least two of the following criteria meets the criteria for Metabolic Syndrome: (a) abdominal obesity (waist to hip ratio of greater than 0.9, a body mass index of at least 30 kg/m2, or a waist measurement over 37 inches); (b) cholesterol panel showing a triglyceride level of at least 150 mg/dl or an HDL cholesterol lower than 35 mg/di; (c) blood pressure of 140/90 or more, or on treatment for high blood pressure). (Mathur, Ruchi, "Metabolic Syndrome," ed. Shiel, Jr., William C., MedicineNet.com, May 11, 2009).

For purposes herein, if an individual meets the criteria of either or both of the criteria set forth by the 2001 National Cholesterol Education Program Adult Treatment Panel or the WHO, that individual is considered as afflicted with Metabolic Syndrome.

Without being bound to any particular theory, peptides described herein are useful for treating Metabolic Syndrome. Accordingly, the invention provides a method of preventing or treating Metabolic Syndrome, or reducing one, two, three or more risk factors thereof, in a subject, comprising providing to the subject an analog described herein in an amount effective to prevent or treat Metabolic Syndrome, or the risk factor thereof.

In some embodiments, the method treats a hyperglycemic medical condition. In certain aspects, the hyperglycemic medical condition is diabetes, diabetes mellitus type I, diabetes mellitus type II, or gestational diabetes, either insulin-dependent or non-insulin-dependent. In some aspects, the method treats the hyperglycemic medical condition by reducing one or more complications of diabetes including nephropathy, retinopathy and vascular disease.

In some aspects, the disease or medical condition is obesity. In some aspects, the obesity is drug-induced obesity. In some aspects, the method treats obesity by preventing or reducing weight gain or increasing weight loss in the patient. In some aspects, the method treats obesity by reducing appetite, decreasing food intake, lowering the levels of fat in the patient, or decreasing the rate of movement of food through the gastrointestinal system.

Because obesity is associated with the onset or progression of other diseases, the methods of treating obesity are further useful in methods of reducing complications associated with obesity including vascular disease (coronary artery disease, stroke, peripheral vascular disease, ischemia reperfusion, etc.), hypertension, onset of diabetes type II, hyperlipidemia and musculoskeletal diseases. The invention accordingly provides methods of treating or preventing these obesity-associated complications.

In some embodiments, the disease or medical condition is Nonalcoholic fatty liver disease (NAFLD). NAFLD refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). Simple fatty liver is the abnormal accumulation of a certain type of fat, triglyceride, in the liver cells with no inflammation or scarring. In NASH, the fat accumulation is associated with varying degrees of inflammation (hepatitis) and scarring (fibrosis) of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. NASH can ultimately lead to scarring of the liver (fibrosis) and then irreversible, advanced scarring (cirrhosis). Cirrhosis that is caused by NASH is the last and most severe stage in the NAFLD spectrum. (Mendler, Michel, "Fatty Liver: Nonalcoholic Fatty Liver Disease (NAFLD) and Nonalcoholic Steatohepatitis (NASH)," ed. Schoenfield, Leslie J., MedicineNet.com, Aug. 29, 2005).

Alcoholic Liver Disease, or Alcohol-Induced Liver Disease, encompasses three pathologically distinct liver diseases related to or caused by the excessive consumption of alcohol: fatty liver (steatosis), chronic or acute hepatitis, and cirrhosis. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). Cirrhosis is characterized anatomically by widespread nodules in the liver combined with fibrosis. (Worman, Howard J., "Alcoholic Liver Disease", Columbia University Medical Center website).

Without being bound to any particular theory, the analogs described herein are useful for the treatment of Alcoholic Liver Disease, NAFLD, or any stage thereof, including, for example, steatosis, steatohepatitis, hepatitis, hepatic inflammation, NASH, cirrhosis, or complications thereof. Accordingly, the invention provides a method of preventing or treating Alcoholic Liver Disease, NAFLD, or any stage thereof, in a subject comprising providing to a subject an analog described herein in an amount effective to prevent or treat Alcoholic Liver Disease, NAFLD, or the stage thereof. Such treatment methods include reduction in one, two, three or more of the following: liver fat content, incidence or progression of cirrhosis, incidence of hepatocellular carcinoma, signs of inflammation, e.g., abnormal hepatic enzyme levels (e.g., aspartate aminotransferase AST and/or alanine aminotransferase ALT, or LDH), elevated serum ferritin, elevated serum bilirubin, and/or signs of fibrosis, e.g., elevated TGF-beta levels. In preferred embodiments, the peptides are used treat patients who have progressed beyond simple fatty liver (steatosis) and exhibit signs of inflammation or hepatitis. Such methods may result, for example, in reduction of AST and/or ALT levels.

GLP-1 and exendin-4 have been shown to have some neuroprotective effect. The invention also provides uses of the glucagon analogs described herein in treating neurodegenerative diseases, including but not limited to Alzheimer's disease, Parkinson's disease, Multiple Sclerosis, Amylotrophic Lateral Sclerosis, other demyelination related disorders, senile dementia, subcortical dementia, arteriosclerotic dementia, AIDS-associated dementia, or other dementias, a central nervous system cancer, traumatic brain injury, spinal cord injury, stroke or cerebral ischemia, cerebral vasculitis, epilepsy, Huntington's disease, Tourette's syndrome, Guillain Barre syndrome, Wilson disease, Pick's disease, neuroinflammatory disorders, encephalitis, encephalomyelitis or meningitis of viral, fungal or bacterial origin, or other central nervous system infections, prion diseases, cerebellar ataxias, cerebellar degeneration, spinocerebellar degeneration syndromes, Friedreichs ataxia, ataxia telangiectasia, spinal dysmyotrophy, progressive supranuclear palsy, dystonia, muscle spasticity, tremor, retinitis pigmentosa, striatonigral degeneration, mitochondrial encephalo-myopathies, neuronal ceroid lipofuscinosis, hepatic encephalopathies, renal encephalopathies, metabolic encephalopathies, toxin-induced encephalopathies, and radiation-induced brain damage.

In some embodiments, the disease or medical condition is hypoglycemia. In some embodiments, the patient is a diabetic patient and the hypoglycemia is induced by the administration of insulin. In specific aspects, the method comprises providing the analog of the present disclosure in combination with insulin so that the analog buffers the hypoglycemic effects of the bolus administration of insulin.

In some embodiments, the glucagon analogs are used in conjunction with parenteral administration of nutrients to non-diabetic patients in a hospital setting, e.g., to patients receiving parenteral nutrition or total parenteral nutrition. Nonlimiting examples include surgery patients, patients in comas, patients with digestive tract illness, or a nonfunctional gastrointestinal tract (e.g. due to surgical removal, blockage or impaired absorptive capacity, Crohn's disease, ulcerative colitis, gastrointestinal tract obstruction, gastrointestinal tract fistula, acute pancreatitis, ischemic bowel, major gastrointestinal surgery, certain congenital gastrointestinal tract anomalies, prolonged diarrhea, or short bowel syndrome due to surgery, patients in shock, and patients undergoing healing processes often receive parenteral administration of carbohydrates along with various combinations of lipids, electrolytes, minerals, vitamins and amino acids. The glucagon analogs and the parenteral nutrition composition can be administered at the same time, at different times, before, or after each other, provided that the glucagon analog is exerting the desired biological effect at the time that the parenteral nutrition composition is being digested. For example, the parenteral nutrition may be administered, 1, 2 or 3 times per day, while the glucagon analog is administered once every other day, three times a week, two times a week, once a week, once every 2 weeks, once every 3 weeks, or once a month.

As used herein, the terms "treat," and "prevent" as well as words stemming therefrom, do not necessarily imply 100% or complete treatment or prevention. Rather, there are varying degrees of treatment or prevention of which one of ordinary skill hi the art recognizes as having a potential benefit or therapeutic effect. In this respect, the inventive methods can provide any amount of any level of treatment or prevention of a disease or medical condition in a mammal. Furthermore, the treatment or prevention provided by the method can include treatment or prevention of one or more conditions or symptoms of the disease or medical condition. For example, with regard to methods of treating obesity, the method in some embodiments, achieves a decrease in food intake by or fat levels in a patient. Also, for purposes herein, "prevention" can encompass delaying the onset of the disease, or a symptom or condition thereof.

With regard to the above methods of treatment, the patient is any host. In some embodiments, the host is a mammal. As used herein, the term "mammal" refers to any vertebrate animal of the mammalia class, including, but not limited to, any of the monotreme, marsupial, and placental taxas. In some embodiments, the mammal is one of the mammals of the order Rodentia, such as mice and hamsters, and mammals of the order Logomorpha, such as rabbits. In certain embodiments, the mammals are from the order Carnivora, including Felines (cats) and Canines (dogs). In certain embodiments, the mammals are from the order Artiodactyla, including Bovines (cows) and S wines (pigs) or of the order Perssodactyla, including Equines (horses). In some instances, the mammals are of the order Primates, Ceboids, or Simoids (monkeys) or of the order Anthropoids (humans and apes). In particular embodiments, the mammal is a human.

Kits

The glucagon analogs of the present disclosure can be provided in accordance with one embodiment as part of a kit. Accordingly, in some embodiments, a kit for administering a glucagon analog, e.g., a glucagon agonist peptide, to a patient in need thereof is provided wherein the kit comprises a glucagon analog as described herein.

In one embodiment the kit is provided with a device for administering the glucagon composition to a patient, e.g., syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the glucagon analog in a lyophilized form or in an aqueous solution. The kits in some embodiments comprise instructions for use. In accordance with one embodiment the device of the kit is an aerosol dispensing device, wherein the composition is prepackaged within the aerosol device. In another embodiment the kit comprises a syringe and a needle, and in one embodiment the sterile glucagon composition is prepackaged within the syringe.

The following examples are given merely to illustrate the present invention and not in any way to limit its scope.

EXAMPLES

Example 1

Synthesis of Peptide Fragments of Glucagon

Materials:

All peptides described herein in the EXAMPLES were amidated unless specified otherwise.

MBHA resin (4-methylbenzhydrylamine polystyrene resin was used during peptide synthesis. MBHA resin, 100-180 mesh, 1% DVB cross-linked polystyrene; loading of 0.7-1.0 mmol/g), Boc-protected and Fmoc protected amino acids were purchased from Midwest Biotech. The solid phase peptide syntheses using Boc-protected amino acids were performed on an Applied Biosystem 430A Peptide Synthesizer. Fmoc protected amino acid synthesis was performed using the Applied Biosystems Model 433 Peptide Synthesizer.

Peptide Synthesis (Roc Amino Acids/HF Cleavage):

Synthesis of these analogs was performed on the Applied Biosystem Model 430A Peptide Synthesizer. Synthetic peptides were constructed by sequential addition of amino acids to a cartridge containing 2 mmol of Boc protected amino acid. Specifically, the synthesis was carried out using Boc DEPBT-activated single couplings. At the end of the coupling step, the peptidyl-resin was treated with TFA to remove the N-terminal Boc protecting group. It was washed repeatedly with DMF and this repetitive cycle was repeated for the desired number of coupling steps. After the assembly, the sidechain protection, Fmoc, was removed by 20% piperidine treatment and acylation was conducted using DIC. The peptidyl-resin at the end of the entire synthesis was dried by using DCM, and the peptide was cleaved from the resin with anhydrous HF.

For the lactamization, orthogonal protecting groups were selected for Glu and Lys (e.g., Glu(Fm), Lys(Fmoc)). After removal of the protecting groups and before HF cleavage, cyclization was performed as described previously (see, e.g., International Patent Application Publication No. WO2008/101017).

HF Treatment of the Peptidyl-Resin

The peptidyl-resin was treated with anhydrous HF, and this typically yielded approximately 350 mg (~50% yield) of a crude deprotected-peptide. Specifically, the peptidyl-resin (30 mg to 200 mg) was placed in the hydrogen fluoride (HF) reaction vessel for cleavage. 500 µL of p-cresol was added to the vessel as a carbonium ion scavenger. The vessel was attached to the HF system and submerged in the methanol/dry ice mixture. The vessel was evacuated with a vacuum pump and 10 ml of HF was distilled to the reaction vessel. This reaction mixture of the peptidyl-resin and the HF was stirred for one hour at 0° C., after which a vacuum was established and the HF was quickly evacuated (10-15 min). The vessel was removed carefully and filled with approximately 35 ml of ether to precipitate the peptide and to extract the p-cresol and small molecule organic protecting groups resulting from HF treatment. This mixture was filtered utilizing a teflon filter and repeated twice to remove all excess cresol. This filtrate was discarded. The precipitated peptide dissolves in approximately 20 ml of 10% acetic acid (aq). This filtrate, which contained the desired peptide, was collected and lyophilized.

An analytical HPLC analysis of the crude solubilized peptide was conducted under the following conditions [4.6×30 mm Xterra C8, 1.50 mL/min, 220 nm, A buffer 0.1% TFA/10% ACN, B buffer 0.1% TFA/100% ACN, gradient 5-95% B over 15 minutes]. The extract was diluted twofold with water and loaded onto a 2.2×25 cm Vydac C4 preparative reverse phase column and eluted using an acetonitrile gradient on a Waters HPLC system (A buffer of 0.1% TFA/10% ACN, B buffer of 0.1% TFA/10% CAN and a gradient of 0-100% B over 120 minutes at a flow of 15.00 ml/min. HPLC analysis of the purified peptide demonstrated greater than 95% purity and electrospray ionization mass spectral analysis was used to confirm the identity of the peptide.

Peptide Acylation

Acylated peptides were prepared as follows. Peptides were synthesized on a solid support resin using either a CS Bio 4886 Peptide Synthesizer or Applied Biosystems 430A Peptide Synthesizer. In situ neutralization chemistry was used as described by Schnolzer et al., Int. J. Peptide Protein Res. 40: 180-193 (1992). For acylated peptides, the target amino acid residue to be acylated (e.g., position ten, relative to the amino acid position numbering of SEQ ID NO: 3) was substituted with an Nε-FMOC lysine residue. Treatment of the completed N-terminally BOC protected peptide with 20% piperidine in DMF for 30 minutes removed FMOC/formyl groups. Coupling to the free ε-amino Lys residue was achieved by coupling a ten-fold molar excess of either an FMOC-protected spacer amino acid (ex. FMOC-Glu-OtBu) or acyl chain (ex. $CH_3(CH_2)_{14}$—COOH) and PyBOP or DEPBT coupling reagent in DMF/DIEA. Subsequent removal of the spacer amino acid's FMOC group is followed by repetition of coupling with an acyl chain. Final treatment with 100% TFA resulted in removal of any side chain protecting groups and the N-terminal BOC group. Peptide resins were neutralized with 5% DIEA/DMF, dried, and then cleaved from the support using HF/p-cresol, 95:5, at 0° C. for one hour. Following ether extraction, a 5% HOAc solution was used to solvate the crude peptide. A sample of the solution was then verified to contain the correct molecular weight peptide by ESI-MS. Correct peptides were purified by RP-HPLC using a linear gradient of 10% CH3CN/0.1% TFA to 0.1% TFA in 100% CH3CN. A Vydac C18 22 mm×250 mm protein column was used for the purification. Acylated peptide analogs generally completed elution by a buffer ratio of 20:80. Portions were pooled together and checked for purity on an analytical RP-HPLC. Pure fractions were lyophilized yielding white, solid peptides.

If a peptide comprised a lactam bridge and target residues to be acylated, acylation is carried out as described above upon addition of that amino acid to the peptide backbone.

Peptide PEGylation

For peptide PEGylation, 40 kDa methoxy poly(ethylene glycol) idoacetamide (NOF) was reacted with a molar equivalent of peptide in 7M Urea, 50 mM Tris-HCl buffer using the minimal amount of solvent needed to dissolve both peptide and PEG into a clear solution (generally less than 2 mL for a reaction using 2-3 mg peptide). Vigorous stiffing at room temperature commenced for 4-6 hours and the reaction analyzed by analytical RP-HPLC. PEGylated products appeared distinctly from the starting material with decreased retention times. Purification was performed on a Vydac C4 column with conditions similar to those used for the initial peptide purification. Elution occurred around buffer ratios of 50:50. Fractions of pure PEGylated peptide were found and lyophilized. Yields were above 50%, varying per reaction.

Analysis Using Mass Spectrometry

The mass spectra were obtained using a Sciex API-III electrospray quadrapole mass spectrometer with a standard ESI ion source. Ionization conditions that were used are as follows: ESI in the positive-ion mode; ion spray voltage, 3.9 kV; orifice potential, 60 V. The nebulizing and curtain gas used was nitrogen flow rate of 0.9 L/min. Mass spectra were recorded from 600-1800 Thompsons at 0.5 Th per step and 2 msec dwell time. The sample (about 1 mg/mL) was dissolved in 50% aqueous acetonitrile with 1% acetic acid and introduced by an external syringe pump at the rate of 5 μL/min.

When the peptides were analyzed in PBS solution by ESI MS, they were first desalted using a ZipTip solid phase extraction tip containing 0.6 μL C4 resin, according to instructions provided by the manufacturer (Millipore Corporation, Billerica, Mass., see the Millipore website of the world wide web at millipore.com/catalogue.nsf/docs/C5737).

High Performance Liquid Chromatography (HPLC) Analysis:

Preliminary analyses were performed with these crude peptides to get an approximation of their relative conversion rates in Phosphate Buffered Saline (PBS) buffer (pH, 7.2) using high performance liquid chromatography (HPLC) and MALDI analysis. The crude peptide samples were dissolved in the PBS buffer at a concentration of 1 mg/ml. 1 ml of the resulting solution was stored in a 1.5 ml HPLC vial which was then sealed and incubated at 37° C. Aliquots of 100 μl were drawn out at various time intervals, cooled to room temperature and analyzed by HPLC.

The HPLC analyses were performed using a Beckman System Gold Chromatography system using a UV detector at 214 nm. HPLC analyses were performed on a 150 mm×4.6 mm C18 Vydac column. The flow rate was 1 ml/min. Solvent A contained 0.1% TFA in distilled water, and solvent B contained 0.1% TFA in 90% CH3CN. A linear gradient was employed (40% to 70% B in 15 minutes). The data were collected and analyzed using Peak Simple Chromatography software.

The initial rates of hydrolysis were used to measure the rate constant for the dissociation of the respective prodrugs. The concentrations of the prodrug and the drug were estimated from their peak areas respectively. The first order dissociation rate constants of the prodrugs were determined by plotting the logarithm of the concentration of the prodrug at various time intervals. The slope of this plot gives the rate constant 'k'. The half lives of the degradation of the various prodrugs were then calculated by using the formula t1/2=0.693/k.

Example 2

The ability of each peptide to induce cAMP was measured in a firefly luciferase-based reporter assay. The cAMP production that is induced is directly proportional to the glucagon fragment binding to the glucagon or GLP-1 receptor. HEK293 cells co-transfected with the glucagon or GLP-1 receptor, respectively, and luciferase gene linked to a cAMP responsive element were employed for the bioassay.

The cells were serum-deprived by culturing 16 hours in Dulbecco-modified Minimum Essential Medium (Invitrogen, Carlsbad, Calif.) supplemented with 0.25% Bovine Growth Serum (HyClone, Logan, Utah) and then incubated with serial dilutions of glucagon fragments for 5 hours at 37° C., 5% CO2 in 96 well poly-D-Lysine-coated "Biocoat" plates (BD Biosciences, San Jose, Calif.). At the end of the incubation, 100 μL of LucLite luminescence substrate reagent (Perkin Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). The effective 50% concentrations (EC50) were calculated by using Origin software (OriginLab, Northampton, Mass.).

Example 3

Starting from the native glucagon sequence (SEQ ID NO: 2), a series of receptor co-agonists have been prepared through insertion of specific helix-favoring amino acid substitutions and peptide backbone conformationtional constraints. Specifically in this report, backbone stabilization was studied using covalent lactam bridge formation at various positions and with differing linker size. In certain peptides, unnatural amino acids (Ornithine (Orn) and diaminobutyric acid (Dab)) and D-amino acid isomers have been applied to further the structure-function analysis.

Peptides 1-19 were made as follows: Each analog was synthesized on MGHA (or T-PAM) resin using Boc-chemistry strategy. As for the cyclized (lactam bridged) peptides, Fmoc-deprotection in the side chains were first implemented in the presence of 20% piperidine/DMF for 1 hour. The covalent lactam bond was formed with the coupling reagent of PyBOP for 5 hours. Peptides were cleaved from the resin using HF/p-cresol (95:5) for 1 hour at 0 deg C. Following HF removal and ether precipitation, the peptides were extracted into 1% HOAc and 20% CAN, and lyophilized. Each peptide was purified using RP-HPLC in 0.1% TFA using a linear gradient of CAN, on a Waters HPLC system. Fractions containing the desired peptide were pooled and lyophilized. The identity and purity of each was confirmed by analytical HPLC and MS analyses.

The structures of Peptides 1-19 are shown in FIG. 1. Lower case letters designate the D-isomer of the amino acid represented by that letter. For example, "k" is the D-isomer of lysine. Lines are drawn between two amino acids represent a lactam bridge. The number on the left designates the peptide number. For example, "1" is for Peptide I. The top amino acid sequence is the native human glucagon sequence (SEQ ID NO: 2). The amino acid sequences are also provided herein in the sequence listing according to the SEQ ID NO: as designated in Table 1. Table 1 also shows the in vitro EC50s of the peptides at each of the glucagon and GLP-1 receptors as tested by the luciferase-based reporter assay as essentially described herein in Example 2.

TABLE 1

| Peptide | SEQ ID NO: | Glucagon Receptor | | GLP-1 Receptor | |
|---|---|---|---|---|---|
| | | EC50 (nM) | Std Dev | EC50 (nM) | Std Dev |
| WT Glucagon | 2 | 0.14 | 0.01 | 7.12 | 0.442 |
| WT GLP-1 | | nd | nd | 0.023 | 0.002 |
| Peptide 1 | 18 | 0.14 | 0.02 | 0.13 | 0.11 |
| Peptide 2 | 19 | 0.12 | 0.00 | 0.12 | 0.10 |
| Peptide 3 | 20 | 0.34 | 0.05 | 1.15 | 0.35 |
| Peptide 4 | 21 | 1.27 | 0.12 | 23.82 | 0.32 |
| Peptide 5 | 22 | 3.51 | nd | 26.10 | nd |
| Peptide 6 | 23 | 0.61 | nd | 2.38 | nd |
| Peptide 7 | 24 | 0.21 | nd | 0.15 | nd |
| Peptide 8 | 25 | 1.76 | 0.05 | nd | nd |
| Peptide 9 | 26 | 6.71 | 0.44 | 14.64 | 0.23 |
| Peptide 10 | 27 | 6.80 | 0.38 | 16.15 | 0.13 |
| Peptide 11 | 28 | 0.90 | nd | 5.79 | nd |
| Peptide 12 | 29 | 85.88 | nd | 41.73 | nd |
| Peptide 13 | 30 | 30.66 | nd | 14.35 | nd |
| Peptide 14 | 31 | 329.14 | nd | 33.00 | nd |
| Peptide 15 | 32 | 19.42 | nd | 73.42 | nd |
| Peptide 16 | 33 | nd | nd | 120.51 | nd |
| Peptide 17 | 34 | 861.57 | nd | 147.94 | nd |
| Peptide 18 | 35 | 719.31 | nd | 116.60 | nd |
| Peptide 19 | 36 | 78.97 | nd | 10.05 | nd | nd = not determined

These results emphasize the importance of lactam ring location and size in the achievement of balanced co-agonism. Glucagon analogs with significant increases in potency at the GLP-1 receptor were created with specific mutations which increase alpha helicity. The central region of the peptides is the preferred location for backbone stabilization, with 16-20 and 17-21 being of comparable character (Peptides 2 and 7). The open form of the 17-21 linear peptide was comparably potent and balanced in its co-agonist (Peptide 1). Glucagon C-terminal amides that are appropriately stabilized in the central region of the peptide can provide potent balanced co-agonism. Ligands of low nanomolar affinity, full agonism, and nearly equal potency at the human glucagon and GLP-1 receptor have thus been identified.

Example 4

Glucagon analogs comprising a modified amino acid sequence of SEQ ID NO: 2 comprising at least three (additional) alpha helix promoting amino acids were made as essentially described in Example 1. Each analog comprised at least one salt bridge and the salt bridge was between Lys at position 17 and Glu at position 21. The analogs further comprised either a second salt bridge between the amino acids at positions 16 and 20, or an alpha, alpha disubstituted amino acid at position 16. The glucagon analogs were DPP-IV-protected insofar as each analog comprised an amino acid which achieves DPP-IV protection, as described herein, at either position 1 or 2. The structures of the glucagon analogs are shown in FIG. 2. "ser" indicates the D-isomer of serine, "Aib" represents alpha, aminoisobutyric acid, and "Dmia" represents alpha, alpha-dimethyl imidiazole acetic acid. Glucagon Analog 22 comprised an acylated Lys at position 10 in which a C16 fatty acyl group was attached to the epsilon amine of Lys via a gamma-glutamic acid spacer residue (see, e.g., FIG. 7). Glucagon Analog 23 which comprised a lactam between the Glu at position 16 and the Lys at position 20, served as a positive control. Glucagon Analogs 23 through 28 were conjugated to a 40 kDa PEG through a thioether linkage with the Cys residue located at position 24 of the analog. The glucagon analogs were tested for in vitro activity at each of the glucagon receptor and GLP-1 receptor, as essentially described in Example 2. The structures and EC50's at the indicated receptor of each peptide, are provided in Table 2A.

TABLE 2A

| Glucagon Analog No. | SEQ ID NO: | Activity at Glucagon Receptor | | Activity at GLP-1 Receptor | |
|---|---|---|---|---|---|
| | | EC50 (nM)* | % Relative Activity** | EC50 (nM)* | % Relative Activity*** |
| 20 | 37 | 0.054 | nd | 0.284 | nd |
| 21 | 38 | 0.073 | nd | 0.048 | nd |
| 22 | 39 | 0.029 | nd | 0.032 | nd |
| 23 | 40 | 0.078 | 45 | 0.427 | 10 |
| 24 | 41 | 0.676 | 7 | 1.581 | 5 |
| 25 | 42 | 1.066 | 3 | 0.097 | 43 |
| 26 | 43 | 0.366 | 10 | 4.797 | 0.1 |
| 27 | 44 | 0.689 | 5 | 0.207 | 20 |
| 28 | 45 | 0.238 | 15 | 1.218 | 3 |
| 101 | 114 | 1.00 | 5.5 | 0.140 | 20 |
| 23' | 40 | 0.110 | 50 | 0.3 | 9.3 |
| 23 | 40 | 0.078 | 45 | 0.427 | 10 |

Glucagon Analog 23' has the same amino acid sequence as Glucagon Analog 23. The linker which attaches the PEG are different among the two Analogs. In Glucagon Analog 23, the thiol of the Cys at position 24 is modified with a haloacetyl-activated PEG in a nucleophilic substitution reaction, as described herein, whereas in Glucagon Analog 23', the thiol of the Cys at position 24 is modified with maleimide-activated PEG lined to peptide via a thioether as described herein.
*EC50 of analog indicated in left column.
**Percent activity of the indicated analog as compared to native glucagon at the glucagon receptor.
***Percent activity of the indicated analog as compared to native GLP-1 at the GLP-1 receptor.
Data of Analogs 101, 23' and 23 are included for comparative purposes and were not necessarily obtained on the same day as the other analogs.

Additional glucagon analogs were made and tested in accordance with the descriptions of Examples 1 and 2. The structures of these glucagon analogs are shown in FIG. 3 and their in vitro activities are shown in Table 2B.

TABLE 2B

| Glucagon Analog No. | SEQ ID NO: | Activity at Glucagon Receptor | | Activity at GLP-1 Receptor | |
|---|---|---|---|---|---|
| | | EC50 (nM)* | % Relative Activity** | EC50 (nM)* | % Relative Activity*** |
| 60 | 75 | 0.006 | 257 | 0.196 | 19 |
| 61 | 76 | 0.017 | 88 | 0.096 | 39 |
| 62 | 77 | 0.015 | 113 | 0.028 | 246 |

TABLE 2B-continued

| Glucagon Analog No. | SEQ ID NO: | Activity at Glucagon Receptor | | Activity at GLP-1 Receptor | |
|---|---|---|---|---|---|
| | | EC50 (nM)* | % Relative Activity** | EC50 (nM)* | % Relative Activity*** |
| 63 | 78 | 0.011 | 115 | 0.020 | 345 |
| 64 | 79 | 0.019 | 79 | 0.012 | 308 |
| 65 | 80 | 0.053 | 264 | 0.036 | 64 |
| 66 | 81 | 0.140 | 100 | 0.130 | 18 |
| 67 | 82 | 0.077 | 93 | 0.071 | 47 |
| 68 | 83 | 0.068 | 104 | 0.075 | 44 |

*EC50 of analog indicated in left column.
**Percent activity of the indicated analog as compared to native glucagon at the glucagon receptor.
***Percent activity of the indicated analog as compared to native GLP-1 at the GLP-1 receptor.
Data values for Analogs 65-68 were not obtained on the same days as the other analogs in this table. The data are presented for purposes of comparison.

This example demonstrated that glucagon analogs comprising at least three alpha helix promoting amino acids are potent glucagon/GLP-1 receptor co-agonists.

Example 5

Acylated glucagon analogs (Glucagon Analogs 42-45 and 48-52) comprising an amino acid which achieves DPP-IV resistance at position 2, a small aliphatic amino acid at position 18, a charged amino acid C-terminal to position 27, and a C-terminal amide in place of the alpha carboxylate were made as essentially described in Example 1. Glucagon Analog 45 comprised these same features except that it lacked the C-terminal amidation, and comprised an Ile at position 7. The structures of each glucagon analog are shown in FIG. 4A. "Aib" refers to alpha, aminoisobutyric acid, "ser" refers to the D-isomer of Ser, "amide" refers to the replacement of the alpha carboxylate on the C-terminal amino acid with an amide, "acid" refers to the C-terminal amino acid comprising an alpha carboxylate. The Lys at position 10 of Glucagon Analogs 42-46 and 48-52 was acylated with a C16 fatty acyl group via a single gamma-glutamic acid spacer or a gamma-glutamic acid-gamma-glutamic acid dipeptide spacer (see, e.g., FIG. 7).

The glucagon analogs were tested for in vitro activity at each of the glucagon and GLP-1 receptors and the results are shown in Table 3A.

TABLE 3A

| Glucagon Analog No. | SEQ ID NO: | Activity at Glucagon Receptor | | Activity at GLP-1 Receptor | |
|---|---|---|---|---|---|
| | | EC50 [pM]* | % Relative Activity** | EC50 [pM]* | % Relative Activity*** |
| 42 | 58 | 3 | 863 | 5 | 500 |
| 43 | 59 | 6 | 467 | 4 | 575 |
| 44 | 60 | 6 | 661 | 4 | 524 |
| 45 | 61 | 52 | 75 | 3 | 759 |
| 46 | 62 | 1 | 2800 | 479 | 4.9 |
| 48 | 63 | 3 | 1194 | 6 | 384 |
| 49 | 64 | 5 | 511 | 6 | 375 |
| 50 | 65 | 2 | 1000 | 5 | 500 |
| 51 | 66 | 3.5 | 314 | 3.9 | 949 |
| 52 | 67 | 2.9 | 379 | 2.9 | 1276 |

*EC50 of analog indicated in left column.
**Percent activity of the indicated analog as compared to Native glucagon at the glucagon receptor.
***Percent activity of the indicated analog as compared to native GLP-1 at the GLP-1 receptor.

As shown in Table 3, glucagon analogs with significant increases in potency at the GLP-1 receptor were created with a number of mutations that permit retained or enhanced activity and which are optimized for in vivo efficacy and pharmaceutical properties by eliminating potential issues associated with oxidation and deamidation, and/or selectively reducing GLP-1 activity or glucagon activity.

The effects of the acylation spacer as well as conjugation to a hydrophilic moiety on the glucagon analogs of this type were analysed by making and testing Glucagon Analogs 69-73. The structure of these analogs are shown in FIG. 4B.

The glucagon analogs were tested for in vitro activity at each of the glucagon and GLP-1 receptors and the results are shown in Table 3B.

TABLE 3B

| Glucagon Analog No. | SEQ ID NO: | Activity at Glucagon Receptor | | Activity at GLP-1 Receptor | |
|---|---|---|---|---|---|
| | | EC50 [pM]* | % Relative Activity** | EC50 [pM]* | % Relative Activity*** |
| 69 | 84 | 12 | 325 | 5 | 440 |
| 70 | 85 | 6 | 709 | 4 | 500 |
| 71 | 86 | 4 | 975 | 2 | 1222 |

*EC50 of analog indicated in left column.
**Percent activity of the indicated analog as compared to Native glucagon at the glucagon receptor.
***Percent activity of the indicated analog as compared to native GLP-1 at the GLP-1 receptor.

Glucagon analogs having a similar backbone structure to Glucagon Analog 52 were made as essentially described herein and were named Glucagon Analogs 76-79, 82, and 83. Glucagon analogs having a similar backbone structure to Glucagon Analog 51 were made as essentially described herein and were named Glucagon Analogs 80 and 81. Glucagon Analogs 78-81 were conjugated to a 40 kDa PEG through the thiol of the Cys at position 24. The structures of these analogs are shown in FIG. 4B. The in vitro activities at the GLP-1 receptor and glucagon receptor were tested as essentially described in Example 2. The EC50s from the in vitro study are shown in Table 3C.

TABLE 3C

| Glucagon Analog No. | SEQ ID NO: | Activity at Glucagon Receptor | | Activity at GLP-1 Receptor | |
|---|---|---|---|---|---|
| | | EC50 [nM]* | % Relative Activity** | EC50 [nM]* | % Relative Activity*** |
| 76 | 89 | 0.002 | 1500 | 0.003 | 1200 |
| 77 | 90 | 0.026 | 127 | 0.014 | 286 |
| 78 | 91 | 0.140 | 44 | 0.026 | 196 |
| 79 | 92 | 0.240 | 26 | 0.125 | 41 |
| 80 | 93 | 0.022 | 86 | 0.008 | 450 |
| 81 | 94 | 0.037 | 51.4 | 0.012 | 300 |
| 82 | 95 | 0.014 | 121 | 0.020 | 345 |
| 83 | 96 | 0.028 | 61 | 0.024 | 288 |

*EC50 of analog indicated in left column.
**Percent activity of the indicated analog as compared to Native glucagon at the glucagon receptor.
***Percent activity of the indicated analog as compared to native GLP-1 at the GLP-1 receptor.

Example 6

The in vivo effects of certain glucagon analogs described in Examples 4 and 5 are tested. The glucagon analogs are subcutaneously injected into diet-induced obesity (DIO) mice with one of the analogs, or vehicle alone, daily for 1-2 weeks. Each group of mice contain 6-8 mice with an initial average body weight of about 40-60 g. Body weight, body composition, food intake, and blood glucose levels are determined periodically (e.g., every day or every 2 days).

Example 7

The effect of conjugating Glucagon Analogs 51 and 52 to a hydrophilic moiety on the in vitro activity at each of the glucagon and GLP-1 receptors was observed by making and testing Glucagon Analogs 29 and 30 which are pegylated versions of Glucagon Analogs 51 and 52, respectively. Glucagon Analogs 29 and 30 are conjugated to a 40 kDa PEG via the Cys at position 24. Analogs were made and tested as essentially described in Examples 1 and 2. The in vitro activities are shown in Table 4.

TABLE 4

| Glucagon Analog No. | SEQ ID NO: | EC50 (pM) at Glucagon Receptor | EC50 (pM) at GLP-1 Receptor |
|---|---|---|---|
| 51 | 66 | 3.5 | 3.9 |
| 29 | 46 | 85 | 84 |
| 52 | 67 | 2.9 | 2.9 |
| 30 | 47 | 82 | 8 |

Example 8

Glucagon Analogs based on the structure of Glucagon Analog 30 without conjugation to a 40 kDa PEG were made. Specifically, glucagon analogs comprising an amino acid which achieves DPP-IV resistance different from the one of Glucagon Analog 30 were made, resulting in Glucagon Analogs 53, 54, and 57. Also, glucagon analogs similar to Glucagon Analog 30 comprising different C-terminal residues were made, resulting in Glucagon Analogs 55 and 56. The structures of the resulting glucagon analogs are shown in FIG. 5. Analogs were made and tested as essentially described in Examples 1 and 2. The in vitro activities are shown in Table 5.

TABLE 5

| Glucagon Analog No. | SEQ ID NO: | Activity at Glucagon Receptor | | Activity at GLP-1 Receptor | |
|---|---|---|---|---|---|
| | | EC50 [nM]* | % Relative Activity** | EC50 [nM]* | % Relative Activity*** |
| 53 | 68 | 0.009 | 411 | 0.012 | 708 |
| 54 | 69 | 0.107 | 35 | 0.204 | 42 |
| 55 | 71 | 0.550 | 7 | 0.516 | 16 |
| 56 | 72 | 0.018 | 272 | 0.068 | 125 |
| 57 | 70 | 4.804 | 1 | nd | nd |
| 23 | 40 | 0.073 | 51 | 0.350 | 24 |

*EC50 of analog indicated in left column.
**Percent activity of the indicated analog as compared to Native glucagon at the glucagon receptor.
***Percent activity of the indicated analog as compared to native GLP-1 at the GLP-1 receptor.
The data on Glucagon Analog 23 is there for comparative purposes.

Example 9

Glucagon Analogs based on the structure of Glucagon Analog 29 were made. Specifically, glucagon analogs comprising an amino acid which achieves DPP-IV resistance different from the one of Glucagon Analog 29 were made, resulting in Glucagon Analogs 58 and 59. The structure of the resulting analogs are shown in FIG. 6. Analogs were made and tested as essentially described in Examples 1 and 2. The in vitro activities are shown in Table 6.

TABLE 6

| Glucagon Analog No. | SEQ ID NO: | Activity at Glucagon Receptor | | Activity at GLP-1 Receptor | |
|---|---|---|---|---|---|
| | | EC50 [nM]* | % Relative Activity** | EC50 [nM]* | % Relative Activity*** |
| 58 | 73 | 0.046 | 80 | 0.068 | 125 |
| 59 | 74 | 0.010 | 490 | 0.019 | 484 |
| 51 | 66 | 0.004 | 314 | 0.004 | 949 |
| 29 | 46 | 0.085 | 40 | 0.084 | 43 |
| 23 | 40 | 0.082 | 60 | 0.445 | 21 |

*EC50 of analog indicated in left column.
**Percent activity of the indicated analog as compared to Native glucagon at the glucagon receptor.
***Percent activity of the indicated analog as compared to native GLP-1 at the GLP-1 receptor.
The data of Peptide 23 was included for comparative purposes and was not necessarily obtained on the same day as the other analogs.

Example 10

Glucagon analogs comprising a modified amino acid sequence of native human glucagon (SEQ ID NO: 2) with amino acids at positions 16-24 substituted with amino acids 16-24 of Exendin-4 (SEQ ID NO: 8), optionally with further modification, were made as essentially described herein.

In a first assay, a glucagon analog comprising Glu at position 16 and amino acids 17-24 of Exendin-4 as described above (Analog A) was made and compared to a glucagon analog comprising Glu at position 16 and amino acids 17-24 of GLP-1 (Analog B). Each of these two peptides were further modified by amino acid substitution with an AIB at position 2 for DPP-IV resistance. Analogs C and D corresponded to the DPP-IV protected versions of Analogs A and B, respectively. The peptides were tested for in vitro activity at each of the glucagon and GLP-1 receptors as essentially described herein in Example 2. The EC50s exhibited by the peptides are shown in Table 7A.

TABLE 7A

| Glucagon Analog | SEQ ID NO: | EC50 (nM) at Glucagon Receptor | EC50 (nM) at GLP-1 Receptor |
|---|---|---|---|
| A | 115 | 0.061 | 0.009 |
| B | 116 | 0.072 | 0.014 |
| C | 117 | 0.170 | 0.006 |
| D | 118 | 0.850 | 0.020 |

Other glucagon analogs comprises amino acids 16-24 of Exendin-4 or a similar sequence (e.g., SEQ ID NO: 12) were made as essentially described in Example 1. The structures of the analogs are shown in FIGS. 8A to 8C. Glucagon Analogs 29 and 30 which are further described herein in Example 7, as well as Glucagon Analogs 20 and 21 which are further described herein in Example 4, were used as reference points. Each of Glucagon Analogs 31-36 comprised the amino acid sequence EXAVRLFIX (SEQ ID NO: 12), were DPP-IV protected insofar as each comprised an amino acid at position 1 or 2 which achieved DPP-IV resistance, and none of these analogs comprised an acylated or alkylated amino acid residue. Glucagon Analogs 35 and 36 were conjugated to 40 kDa PEGs through a thioether linkage to a Cys residue of the analog located at position 24 in similar fashion to Analog 23. Each of Glucagon Analogs 37-40 comprised an acylated amino acid of which Glucagon Analogs 37 and 38 comprised a spacer which linked the acyl group to the amino acid of the analog and Glucagon Analogs 39 and 40 did not comprise a spacer.

Glucagon Analogs 84, 85, and 87 comprised a Gln at position 17, while Glucagon Analog 86 comprised a Lys at that position. Glucagon Analog 84 comprised a C-terminal extension. Glucagon Analog 85 comprised an acylated amino acid at position 10 and was conjugated to a 40 kDa PEG via the Cys at position 24. Glucagon Analog 86 additionally comprised an AIB at position 16.

The glucagon analogs were tested for in vitro activity at each of the glucagon and GLP-1 receptors and the results are shown in Table 7B.

TABLE 7B

| Glucagon Analog No. | SEQ ID NO: | EC50 (nM) at Glucagon Receptor | EC50 (nM) at GLP-1 Receptor |
| --- | --- | --- | --- |
| 29* | 47 | 0.085 (74%) | 0.084 (16%) |
| 30* | 48 | 0.082 (55%) | 0.008 (96%) |
| 31 | 49 | 0.118 | 0.015 |
| 32 | 50 | 0.220 | 0.007 |
| 33 | 51 | 0.138 | 0.023 |
| 34 | 52 | 0.404 | 0.018 |
| 35 | 53 | 3.882 | 0.136 |
| 36 | 54 | 5.328 | 0.020 |
| 20' | 37 | 0.054 | 0.284 |
| 21' | 38 | 0.073 | 0.048 |
| 37 | 54 | 0.119 | 0.011 |
| 38 | 55 | 0.655 | 0.019 |
| 39 | 56 | 2.543 | 0.033 |
| 40 | 57 | 48.415 | 0.024 |
| 84 | 97 | 0.132 (14.4%) | 0.006 (600%) |
| 85 | 98 | 0.107 (16%) | 0.013 (284%) |
| 86 | 99 | 0.035 (43%) | 0.035 (106%) |
| 87 | 100 | 0.021 (71%) | 0.013 (284%) |

*reference points

As shown in Table 7, the glucagon analogs with substitutions with amino acids from Exendin-4 exhibited significant potency at the GLP-1 receptor. The potency at the GLP-1 receptor largely remained the same upon acylation (with or without a spacer). PEGylation increased activity at the glucagon receptor. While less potent at the glucagon receptor as compared to the native glucagon ligand, the glucagon analogs exhibits appreciable activity at this receptor.

Example 11

Previously-described Glucagon Analogs 60-62, 64, 82, 83, 86, and 87 were modified by conjugating a Cys residue at position 24 with a 40 kDa PEG. The resulting structures of these modified peptides are shown in FIG. 9.

Furthermore, glucagon analogs previously described herein but modified to comprise a lactam between the amino acids at positions 16 and 20 were made. The structures of these peptides are also shown in FIG. 9.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A glucagon analog comprising the amino acid sequence of SEQ ID NO: 2 with (i) positions 18 through 24 of the analog being AVRLFIX (SEQ ID NO: 11), wherein X is Cys or Glu, and (ii) up to 7 additional amino acid substitutions selected from positions 1-17 and 25-29, relative to SEQ ID NO: 2, wherein the glucagon analog exhibits (i) about 10% or more of native glucagon at the glucagon receptor, (ii) about 10% or more of native GLP-1 at the GLP-1 receptor, or (iii) both (i) and (ii).

2. The glucagon analog of claim 1, comprising a charged amino acid at each of positions 16 and 17, optionally, comprising an acidic amino acid at each of positions 16 and 17 or an acidic amino acid at position 16 and a positive-charged amino acid at position 17.

3. The glucagon analog of claim 2, comprising the amino acid sequence of $EX_1AVRLFIX_2$ (SEQ ID NO: 12) at positions 16 through 24, wherein $X_1$ is E, K, or Q and $X_2$ is E or C.

4. The glucagon analog of claim 1, wherein the analog does not comprise the amino acid sequence: KRNRNNIA (SEQ ID NO: 13).

5. The glucagon analog of claim 1, wherein the glucagon analog comprises an acylated or alkylated amino acid at position 10.

6. The glucagon analog of claim 5, wherein the acylated or alkylated amino acid at position 10 comprises a C8 to C20 alkyl chain, optionally a C12 to C18 alkyl chain or a C14 or C16 alkyl chain.

7. The glucagon analog of claim 5, wherein the acylated or alkylated amino acid is an acylated or alkylated amino acid of Formula I, Formula II, or Formula III, optionally, wherein the amino acid of Formula I is Lys.

8. The glucagon analog of claim 5, further comprising a spacer between the amino acid at position 10 and the acyl group or alkyl group, optionally, wherein the spacer is an amino acid or a dipeptide, optionally comprising one or two acidic residues.

9. The glucagon analog of claim 1, comprising an amino acid which achieves DPP-IV protease resistance at position 1, position 2, or positions 1 and 2, optionally, wherein the amino acid at position 1 is selected from the group consisting of: D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine, optionally, wherein the amino acid at position 2 is selected from the group consisting of: D-serine, alanine, D-alanine, valine, glycine, N-methyl serine, N-methyl alanine, and alpha, amino isobutyric acid (AIB).

10. The glucagon analog of claim 1 comprising a C-terminal amide in place of a C-terminal alpha carboxylate or comprising a hydrophilic moiety, optionally a polyethylene glycol.

11. The glucagon analog of claim 1, comprising one or more of the following amino acid modifications:
  a. Gln at position 3 replaced with a glutamine analog or Glu;
  b. Thr at position 7 replaced with a large, aliphatic amino acid;
  c. Tyr at position 10 replaced with Val or Phe;
  d. Lys at position 12 is replaced with a Arg;
  e. Asp at position 15 is replaced with another acidic amino acid;

f. Met at position 27 replaced with Leu or Norleucine;

g. Asn at position 28 replaced with a negative-charged amino acid; or h. Thr at position 29 replaced with a Gly.

12. A conjugate comprising the glucagon analog of claim 1 conjugated to a heterologous moiety, optionally, wherein the heterologous moiety comprises one or more of: a peptide, a polypeptide, a nucleic acid molecule, an antibody or fragment thereof, a polymer, a quantum dot, a small molecule, a toxin, a diagnostic agent, optionally, wherein the heterologous moiety is a peptide and conjugate is a fusion peptide or a chimeric peptide.

13. A dimer or multimer comprising a glucagon analog of claim 1.

14. A pharmaceutical composition comprising the glucagon analog of claim 1, or a conjugate, dimer or multimer comprising the glucagon analog, or a combination thereof, and a pharmaceutically acceptable carrier.

15. A method of treating a disease or medical condition in a patient in need thereof, wherein the disease or medical condition is selected from the group consisting of: metabolic syndrome, diabetes, obesity, and liver steatosis, comprising administering to the patient the pharmaceutical composition of claim 14 in an amount effective to treat the disease or medical condition.

* * * * *

SEQUENCE LISTING

```
<160> NUMBER OF SEQ ID NOS: 188

<210> SEQ ID NO 1
<211> LENGTH: 158
<212> TYPE: PRT
<213> ORGANISM: Homo sapiens
<220> FEATURE:
<221> NAME/KEY: MISC_FEATURE
<223> OTHER INFORMATION: Pre-proglucagon
<220> FEATURE:
<221> NAME/KEY: MISC_FEATURE
<223> OTHER INFORMATION: Pre-proglucagon

<400> SEQUENCE: 1

Arg Ser Leu Gln Asp Thr Glu Glu Lys Ser Arg Ser Phe Ser Ala Ser
1               5                   10                  15
```

-continued

Gln Ala Asp Pro Leu Ser Asp Pro Asp Gln Met Asn Glu Asp Lys Arg
            20                  25                  30

His Ser Gln Gly Thr Phe Thr Ser Asp Tyr Ser Lys Tyr Leu Asp Ser
            35                  40                  45

Arg Arg Ala Gln Asp Phe Val Gln Trp Leu Met Asn Thr Lys Arg Asn
 50                  55                  60

Arg Asn Asn Ile Ala Lys Arg His Asp Glu Phe Glu Arg His Ala Glu
65                  70                  75                  80

Gly Thr Phe Thr Ser Asp Val Ser Ser Tyr Leu Glu Gly Gln Ala Ala
                85                  90                  95

Lys Glu Phe Ile Ala Trp Leu Val Lys Gly Arg Gly Arg Arg Asp Phe
            100                 105                 110

Pro Glu Glu Val Ala Ile Val Glu Glu Leu Gly Arg Arg His Ala Asp
            115                 120                 125

Gly Ser Phe Ser Asp Glu Met Asn Thr Ile Leu Asp Asn Leu Ala Ala
            130                 135                 140

Arg Asp Phe Ile Asn Trp Leu Ile Gln Thr Lys Ile Thr Asp
145                 150                 155

<210> SEQ ID NO 2
<211> LENGTH: 29
<212> TYPE: PRT
<213> ORGANISM: Homo sapiens
<220> FEATURE:
<221> NAME/KEY: MISC_FEATURE
<223> OTHER INFORMATION: Native human glucagon

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 3
<211> LENGTH: 37
<212> TYPE: PRT
<213> ORGANISM: Homo sapiens
<220> FEATURE:
<221> NAME/KEY: MISC_FEATURE
<223> OTHER INFORMATION: GLP-1

<400> SEQUENCE: 3

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 4
<211> LENGTH: 33
<212> TYPE: PRT
<213> ORGANISM: Homo sapiens
<220> FEATURE:
<221> NAME/KEY: MISC_FEATURE
<223> OTHER INFORMATION: GLP-2

<400> SEQUENCE: 4

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr

```
            20                  25                  30

Asp

<210> SEQ ID NO 5
<211> LENGTH: 37
<212> TYPE: PRT
<213> ORGANISM: Homo sapiens
<220> FEATURE:
<221> NAME/KEY: MISC_FEATURE
<223> OTHER INFORMATION: Oxyntomodulin

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Arg Asn Asn Ile Ala
        35

<210> SEQ ID NO 6
<211> LENGTH: 30
<212> TYPE: PRT
<213> ORGANISM: Homo sapiens
<220> FEATURE:
<221> NAME/KEY: MISC_FEATURE
<223> OTHER INFORMATION: GLP1 (7-36 amide)
<220> FEATURE:
<221> NAME/KEY: MOD_RES
<222> LOCATION: (30)..(30)
<223> OTHER INFORMATION: C-terminal amidation

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 7
<211> LENGTH: 31
<212> TYPE: PRT
<213> ORGANISM: Homo sapiens
<220> FEATURE:
<221> NAME/KEY: MISC_FEATURE
<223> OTHER INFORMATION: GLP-1 (7-37 acid)

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 8
<211> LENGTH: 39
<212> TYPE: PRT
<213> ORGANISM: Heloderma suspectum
<220> FEATURE:
<221> NAME/KEY: MISC_FEATURE
<223> OTHER INFORMATION: Exendin-4

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
```

-continued

```
<210> SEQ ID NO 9
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (29)..(29)
<223> OTHER INFORMATION: C-terminal amidation

<400> SEQUENCE: 9

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (29)..(29)
<223> OTHER INFORMATION: C-terminal amidation

<400> SEQUENCE: 10

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (7)..(7)
<223> OTHER INFORMATION: Xaa is Glu or Cys

<400> SEQUENCE: 11

Ala Val Arg Leu Phe Ile Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is Glu, Lys, or Gln
<220> FEATURE:
<221> NAME/KEY: MOD_RES
<222> LOCATION: (9)..(9)
<223> OTHER INFORMATION: Xaa is Glu or Cys

<400> SEQUENCE: 12

Glu Xaa Ala Val Arg Leu Phe Ile Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Lys Arg Asn Arg Asn Asn Ile Ala
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Gly Pro Ser Ser Gly Ala Pro Pro Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

Gly Gly Pro Ser Ser Gly Ala Pro Pro Ser
1               5                   10

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

Lys Arg Asn Arg
1
```

```
<210> SEQ ID NO 17
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: Xaa is an alpha-methylated amino acid bearing
      an olefinic side chain
<220> FEATURE:
<221> NAME/KEY: MOD_RES
<222> LOCATION: (20)..(20)
<223> OTHER INFORMATION: Xaa is an alpha-methylated amino acid bearing
      an olefinic side chain

<400> SEQUENCE: 17

His Xaa Gln Gly Thr Phe Thr Ser Asp Tyr Ser Lys Tyr Leu Asp Xaa
1               5                   10                  15

Gln Ala Ala Xaa Glu Phe Ile Ala Trp Leu Met Asn Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 1
<220> FEATURE:
<221> NAME/KEY: MOD_RES
<222> LOCATION: (29)..(29)
<223> OTHER INFORMATION: C-terminal amidation

<400> SEQUENCE: 18

His Ser Gln Gly Thr Phe Thr Ser Asp Tyr Ser Lys Tyr Leu Asp Ser
1               5                   10                  15

Lys Arg Ala Gln Glu Phe Val Gln Trp Leu Met Asn Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 2
<220> FEATURE:
<221> NAME/KEY: MISC_FEATURE
<222> LOCATION: (17)..(21)
<223> OTHER INFORMATION: Lactam ring between side chains of amino acids
<220> FEATURE:
<221> NAME/KEY: MOD_RES
<222> LOCATION: (29)..(29)
<223> OTHER INFORMATION: C-terminal amidation

<400> SEQUENCE: 19

His Ser Gln Gly Thr Phe Thr Ser Asp Tyr Ser Lys Tyr Leu Asp Ser
1               5                   10                  15

Lys Arg Ala Gln Glu Phe Val Gln Trp Leu Met Asn Thr
            20                  25
```

```
<210> SEQ ID NO 20
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 3
<220> FEATURE:
<221> NAME/KEY: MISC_FEATURE
<222> LOCATION: (16)..(20)
<223> OTHER INFORMATION: Lactam ring between side chains of amino acids

<400> SEQUENCE: 20

His Ser Gln Gly Thr Phe Thr Ser Asp Tyr Ser Lys Tyr Leu Asp Lys
1               5                   10                  15

Arg Arg Ala Glu Asp Phe Val Gln Trp Leu Met Asn Thr
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 4
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (20)..(20)
<223> OTHER INFORMATION: Xaa is Ornithine

<400> SEQUENCE: 21

His Ser Gln Gly Thr Phe Thr Ser Asp Tyr Ser Lys Tyr Leu Asp Glu
1               5                   10                  15

Arg Arg Ala Xaa Asp Phe Val Gln Trp Leu Met Asn Thr
            20                  25

<210> SEQ ID NO 22
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 5
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (20)..(20)
<223> OTHER INFORMATION: Xaa is diaminobutanoic acid

<400> SEQUENCE: 22

His Ser Gln Gly Thr Phe Thr Ser Asp Tyr Ser Lys Tyr Leu Asp Glu
1               5                   10                  15

Arg Arg Ala Xaa Asp Phe Val Gln Trp Leu Met Asn Thr
            20                  25

<210> SEQ ID NO 23
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 6
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (20)..(20)
<223> OTHER INFORMATION: Xaa is Ornithine

<400> SEQUENCE: 23

His Ser Gln Gly Thr Phe Thr Ser Asp Tyr Ser Lys Tyr Leu Asp Glu
1               5                   10                  15

Arg Arg Ala Xaa Asp Phe Val Gln Trp Leu Met Asn Thr
            20                  25

<210> SEQ ID NO 24
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 7
<220> FEATURE:
<221> NAME/KEY: MOD_RES
<222> LOCATION: (20)..(20)
<223> OTHER INFORMATION: Xaa is Ornithine
<220> FEATURE:
<221> NAME/KEY: MOD_RES
<222> LOCATION: (29)..(29)
<223> OTHER INFORMATION: C-terminal amidation

<400> SEQUENCE: 24

His Ser Gln Gly Thr Phe Thr Ser Asp Tyr Ser Lys Tyr Leu Asp Glu
1               5                   10                  15

Arg Arg Ala Xaa Asp Phe Val Gln Trp Leu Met Asn Thr
            20                  25

<210> SEQ ID NO 25
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 8
<220> FEATURE:
<221> NAME/KEY: MOD_RES
<222> LOCATION: (21)..(21)
<223> OTHER INFORMATION: Xaa is Ornithine

<400> SEQUENCE: 25

His Ser Gln Gly Thr Phe Thr Ser Asp Tyr Ser Lys Tyr Leu Asp Asp
1               5                   10                  15

Arg Arg Ala Gln Xaa Phe Val Gln Trp Leu Met Asn Thr
            20                  25

<210> SEQ ID NO 26
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: Peptide 9
<220> FEATURE:
<221> NAME/KEY: MOD_RES
<222> LOCATION: (20)..(20)
<223> OTHER INFORMATION: Xaa is Ornithine

<400> SEQUENCE: 26

His Ser Gln Gly Thr Phe Thr Ser Asp Tyr Ser Lys Tyr Leu Asp Ser
1               5                   10                  15

Asp Arg Ala Xaa Asp Phe Val Gln Trp Leu Met Asn Thr
            20                  25

<210> SEQ ID NO 27
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 10
<220> FEATURE:
<221> NAME/KEY: MISC_FEATURE
<222> LOCATION: (17)..(20)
<223> OTHER INFORMATION: Lactam ring between side chains of amino acids
<220> FEATURE:
<221> NAME/KEY: MOD_RES
<222> LOCATION: (20)..(20)
<223> OTHER INFORMATION: Xaa is Ornithine

<400> SEQUENCE: 27

His Ser Gln Gly Thr Phe Thr Ser Asp Tyr Ser Lys Tyr Leu Asp Ser
1               5                   10                  15

Asp Arg Ala Xaa Asp Phe Val Gln Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 11
<220> FEATURE:
<221> NAME/KEY: MISC_FEATURE
<222> LOCATION: (17)..(20)
<223> OTHER INFORMATION: Lactam ring between side chains of amino acids
<220> FEATURE:
<221> NAME/KEY: MOD_RES
<222> LOCATION: (20)..(20)
<223> OTHER INFORMATION: Xaa is Ornithine

<400> SEQUENCE: 28

His Ser Gln Gly Thr Phe Thr Ser Asp Tyr Ser Lys Tyr Leu Asp Ser
1               5                   10                  15

Glu Arg Ala Xaa Asp Phe Val Gln Trp Leu Met Asn Thr
            20                  25

<210> SEQ ID NO 29
<211> LENGTH: 31
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<223> OTHER INFORMATION: Peptide 12
<220> FEATURE:
<221> NAME/KEY: MOD_RES
<222> LOCATION: (31)..(31)
<223> OTHER INFORMATION: C-terminal amidation

<400> SEQUENCE: 29

Lys Ala His Ser Glu Gly Thr Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 13
<220> FEATURE:
<221> NAME/KEY: MISC_FEATURE
<222> LOCATION: (1)..(5)
<223> OTHER INFORMATION: Lactam ring between side chains of amino acids
<220> FEATURE:
<221> NAME/KEY: MOD_RES
<222> LOCATION: (31)..(31)
<223> OTHER INFORMATION: C-terminal amidation

<400> SEQUENCE: 30

Lys Ala His Ser Glu Gly Thr Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 14
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (5)..(5)
<223> OTHER INFORMATION: D-Glu
<220> FEATURE:
<221> NAME/KEY: MOD_RES
<222> LOCATION: (30)..(30)
<223> OTHER INFORMATION: C-terminal amidation

<400> SEQUENCE: 31

Lys His Ser Gln Glu Thr Phe Thr Ser Asp Tyr Ser Lys Tyr Leu Asp
1               5                   10                  15

Ser Arg Arg Ala Gln Asp Phe Val Gln Trp Leu Met Asn Thr
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<223> OTHER INFORMATION: Peptide 15
<220> FEATURE:
<221> NAME/KEY: MOD_RES
<222> LOCATION: (1)..(1)
<223> OTHER INFORMATION: D-Lys
<220> FEATURE:
<221> NAME/KEY: MISC_FEATURE
<222> LOCATION: (1)..(5)
<223> OTHER INFORMATION: Lactam ring between side chains of amino acids
<220> FEATURE:
<221> NAME/KEY: MOD_RES
<222> LOCATION: (5)..(5)
<223> OTHER INFORMATION: D-Glu
<220> FEATURE:
<221> NAME/KEY: MOD_RES
<222> LOCATION: (30)..(30)
<223> OTHER INFORMATION: C-terminal amidation

<400> SEQUENCE: 32

Lys His Ser Gln Glu Thr Phe Thr Ser Asp Tyr Ser Lys Tyr Leu Asp
1               5                   10                  15

Ser Arg Arg Ala Gln Asp Phe Val Gln Trp Leu Met Asn Thr
            20                  25                  30

<210> SEQ ID NO 33
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 16
<220> FEATURE:
<221> NAME/KEY: MOD_RES
<222> LOCATION: (29)..(29)
<223> OTHER INFORMATION: C-terminal amidation

<400> SEQUENCE: 33

His Ser Gln Lys Thr Phe Thr Glu Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 34
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 17
<220> FEATURE:
<221> NAME/KEY: MISC_FEATURE
<222> LOCATION: (4)..(8)
<223> OTHER INFORMATION: Lactam ring between side chains of amino acids
<220> FEATURE:
<221> NAME/KEY: MOD_RES
<222> LOCATION: (29)..(29)
<223> OTHER INFORMATION: C-terminal amidation

<400> SEQUENCE: 34

His Ser Gln Lys Thr Phe Thr Glu Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 35
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 18
<220> FEATURE:
<221> NAME/KEY: MOD_RES
<222> LOCATION: (29)..(29)
<223> OTHER INFORMATION: C-terminal amidation

<400> SEQUENCE: 35

His Ser Gln Gly Thr Phe Thr Glu Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 36
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 19
<220> FEATURE:
<221> NAME/KEY: MISC_FEATURE
<222> LOCATION: (8)..(12)
<223> OTHER INFORMATION: Lactam ring between side chains of amino acids
<220> FEATURE:
<221> NAME/KEY: MOD_RES
<222> LOCATION: (29)..(29)
<223> OTHER INFORMATION: C-terminal amidation

<400> SEQUENCE: 36

His Ser Gln Gly Thr Phe Thr Glu Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 37
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 20
<220> FEATURE:
<221> NAME/KEY: MOD_RES
<222> LOCATION: (2)..(2)
<223> OTHER INFORMATION: d-Ser
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (29)..(29)
<223> OTHER INFORMATION: C-terminal amidation

<400> SEQUENCE: 37

His Ser Gln Gly Thr Phe Thr Ser Asp Tyr Ser Lys Tyr Leu Asp Glu
1               5                   10                  15
```

Lys Arg Ala Lys Glu Phe Val Gln Trp Leu Met Asn Thr
            20                  25

<210> SEQ ID NO 38
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 21
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (29)..(29)
<223> OTHER INFORMATION: C-terminal amidation

<400> SEQUENCE: 38

His Ser Gln Gly Thr Phe Thr Ser Asp Tyr Ser Lys Tyr Leu Asp Xaa
1               5                   10                  15

Lys Arg Ala Lys Glu Phe Val Gln Trp Leu Met Asn Thr
            20                  25

<210> SEQ ID NO 39
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 22
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MISC_FEATURE
<222> LOCATION: (15)..(20)
<223> OTHER INFORMATION: Salt bridge
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (16)..(21)
<223> OTHER INFORMATION: Salt bridge
<220> FEATURE:
<221> NAME/KEY: MOD_RES
<222> LOCATION: (29)..(29)
<223> OTHER INFORMATION: C-terminal amidation

<400> SEQUENCE: 39

His Ser Gln Gly Thr Phe Thr Ser Asp Lys Ser Lys Tyr Leu Asp Xaa
1               5                   10                  15

Lys Arg Ala Lys Glu Phe Val Gln Trp Leu Met Asn Thr
            20                  25

<210> SEQ ID NO 40
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 23
<220> FEATURE:
<221> NAME/KEY: MOD_RES
<222> LOCATION: (1)..(1)
<223> OTHER INFORMATION: Xaa is alpha, alpha-dimethyl imidiazole acetic
      acid
<220> FEATURE:
<221> NAME/KEY: MISC_FEATURE
<222> LOCATION: (24)..(24)
<223> OTHER INFORMATION: Covalently bound to 40kDa PEG

<400> SEQUENCE: 40

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 41
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 24
<220> FEATURE:
<221> NAME/KEY: MOD_RES
<222> LOCATION: (2)..(2)
<223> OTHER INFORMATION: d-Ser
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 41

His Ser Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
            20                  25

<210> SEQ ID NO 42
<211> LENGTH: 29
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: Glucagon Analog 25
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (24)..(24)
<223> OTHER INFORMATION: Covalently bound to a 40kDa PEG
<220> FEATURE:
<221> NAME/KEY: MOD_RES
<222> LOCATION: (29)..(29)
<223> OTHER INFORMATION: C-terminal amidation

<400> SEQUENCE: 42

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 26
<220> FEATURE:
<221> NAME/KEY: MOD_RES
<222> LOCATION: (2)..(2)
<223> OTHER INFORMATION: d-Ser
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 43

His Ser Gln Gly Thr Phe Thr Ser Asp Tyr Ser Lys Tyr Leu Asp Xaa
1               5                   10                  15

Lys Arg Ala Lys Glu Phe Val Cys Trp Leu Met Asn Thr
            20                  25

<210> SEQ ID NO 44
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: Glucagon Analog 27
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 44

His Xaa Gln Gly Thr Phe Thr Ser Asp Tyr Ser Lys Tyr Leu Asp Xaa
 1               5                  10                  15

Lys Arg Ala Lys Glu Phe Val Cys Trp Leu Met Asn Thr
            20                  25

<210> SEQ ID NO 45
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 28
<220> FEATURE:
<221> NAME/KEY: MOD_RES
<222> LOCATION: (1)..(1)
<223> OTHER INFORMATION: Xaa is DMIA
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (24)..(24)
<223> OTHER INFORMATION: PEGYLATION
<220> FEATURE:
<221> NAME/KEY: MOD_RES
<222> LOCATION: (29)..(29)
<223> OTHER INFORMATION: C-terminal amidation

<400> SEQUENCE: 45

Xaa Ser Gln Gly Thr Phe Thr Ser Asp Tyr Ser Lys Tyr Leu Asp Xaa
 1               5                  10                  15

Lys Arg Ala Lys Glu Phe Val Cys Trp Leu Met Asn Thr
            20                  25
```

<210> SEQ ID NO 46
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 29
<220> FEATURE:
<221> NAME/KEY: MOD_RES
<222> LOCATION: (2)..(2)
<223> OTHER INFORMATION: d-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 46

His Ser Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25

<210> SEQ ID NO 47
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 30
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 47

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 48
<211> LENGTH: 29
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: Glucagon Analog 31
<220> FEATURE:
<221> NAME/KEY: MOD_RES
<222> LOCATION: (2)..(2)
<223> OTHER INFORMATION: d-Ser
<220> FEATURE:
<221> NAME/KEY: MOD_RES
<222> LOCATION: (29)..(29)
<223> OTHER INFORMATION: C-terminal amidation

<400> SEQUENCE: 48

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr
            20                  25

<210> SEQ ID NO 49
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 32
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 49

His Xaa Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr
            20                  25

<210> SEQ ID NO 50
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 33
<220> FEATURE:
<221> NAME/KEY: MOD_RES
<222> LOCATION: (2)..(2)
<223> OTHER INFORMATION: d-Ser
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (29)..(29)
<223> OTHER INFORMATION: C-terminal amidation

<400> SEQUENCE: 50

His Ser Gln Gly Thr Phe Thr Ser Asp Tyr Ser Lys Tyr Leu Asp Glu
1               5                   10                  15

Glu Ala Val Arg Leu Phe Ile Cys Trp Leu Met Asn Thr
```

```
                            20                  25

<210> SEQ ID NO 51
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 34
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 51

His Xaa Gln Gly Thr Phe Thr Ser Asp Tyr Ser Lys Tyr Leu Asp Glu
1               5                   10                  15

Glu Ala Val Arg Leu Phe Ile Cys Trp Leu Met Asn Thr
            20                  25

<210> SEQ ID NO 52
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 35
<220> FEATURE:
<221> NAME/KEY: MOD_RES
<222> LOCATION: (2)..(2)
<223> OTHER INFORMATION: d-Ser
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 52

His Ser Gln Gly Thr Phe Thr Ser Asp Tyr Ser Lys Tyr Leu Asp Glu
1               5                   10                  15

Glu Ala Val Arg Leu Phe Ile Cys Trp Leu Met Asn Thr
            20                  25

<210> SEQ ID NO 53
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 36
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
```

```
<222> LOCATION: (29)..(29)
<223> OTHER INFORMATION: C-terminal amidation

<400> SEQUENCE: 53

His Xaa Gln Gly Thr Phe Thr Ser Asp Tyr Ser Lys Tyr Leu Asp Glu
1               5                   10                  15

Glu Ala Val Arg Leu Phe Ile Cys Trp Leu Met Asn Thr
            20                  25

<210> SEQ ID NO 54
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 37
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 54

His Ser Gln Gly Thr Phe Thr Ser Asp Lys Ser Lys Tyr Leu Asp Glu
1               5                   10                  15

Glu Ala Val Arg Leu Phe Ile Glu Trp Leu Met Asn Thr
            20                  25

<210> SEQ ID NO 55
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 38
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 55

His Xaa Gln Gly Thr Phe Thr Ser Asp Lys Ser Lys Tyr Leu Asp Glu
1               5                   10                  15

Glu Ala Val Arg Leu Phe Ile Glu Trp Leu Met Asn Thr
            20                  25

<210> SEQ ID NO 56
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

-continued

<223> OTHER INFORMATION: Glucagon Analog 39
<220> FEATURE:
<221> NAME/KEY: MOD_RES
<222> LOCATION: (10)..(10)
<223> OTHER INFORMATION: Acylated with C16 fatty acyl group
<220> FEATURE:
<221> NAME/KEY: MOD_RES
<222> LOCATION: (29)..(29)
<223> OTHER INFORMATION: C-terminal amidation

<400> SEQUENCE: 56

His Ser Gln Gly Thr Phe Thr Ser Asp Lys Ser Lys Tyr Leu Asp Glu
1               5                   10                  15

Glu Ala Val Arg Leu Phe Ile Glu Trp Leu Met Asn Thr
            20                  25

<210> SEQ ID NO 57
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 40
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group
<220> FEATURE:
<221> NAME/KEY: MOD_RES
<222> LOCATION: (29)..(29)
<223> OTHER INFORMATION: C-terminal amidation

<400> SEQUENCE: 57

His Xaa Gln Gly Thr Phe Thr Ser Asp Lys Ser Lys Tyr Leu Asp Glu
1               5                   10                  15

Glu Ala Val Arg Leu Phe Ile Glu Trp Leu Met Asn Thr
            20                  25

<210> SEQ ID NO 58
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 42
<220> FEATURE:
<221> NAME/KEY: MOD_RES
<222> LOCATION: (2)..(2)
<223> OTHER INFORMATION: Xaa is Aminoisobutyric acid
<220> FEATURE:
<221> NAME/KEY: MOD_RES
<222> LOCATION: (10)..(10)
<223> OTHER INFORMATION: Acylated with a C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 58

His Xaa Gln Gly Thr Phe Thr Ser Asp Lys Ser Lys Tyr Leu Asp Xaa

```
1               5                  10                  15
Arg Ala Ala Gln Asp Phe Val Gln Trp Leu Met Asp Thr
            20                  25
```

<210> SEQ ID NO 59
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 43
<220> FEATURE:
<221> NAME/KEY: MOD_RES
<222> LOCATION: (2)..(2)
<223> OTHER INFORMATION: Xaa is Aminoisobutyric acid
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (16)..(16)
<223> OTHER INFORMATION: Xaa is Aminoisobutyric acid
<220> FEATURE:
<221> NAME/KEY: MOD_RES
<222> LOCATION: (29)..(29)
<223> OTHER INFORMATION: C-terminal amidation

<400> SEQUENCE: 59

```
His Xaa Gln Gly Thr Phe Thr Ser Asp Lys Ser Lys Tyr Leu Asp Xaa
1               5                  10                  15
Arg Ala Ala Gln Asp Phe Val Gln Trp Leu Met Asp Thr
            20                  25
```

<210> SEQ ID NO 60
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 44
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 60

```
His Ser Gln Gly Thr Phe Thr Ser Asp Lys Ser Lys Tyr Leu Glu Xaa
1               5                  10                  15
Arg Ala Ala Gln Asp Phe Val Gln Trp Leu Met Asp Thr
            20                  25
```

<210> SEQ ID NO 61
<211> LENGTH: 29

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 45
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 61

His Xaa Glu Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 62
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 46
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB

<400> SEQUENCE: 62

His Xaa Gln Gly Thr Phe Ile Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 63
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 48
<220> FEATURE:
<221> NAME/KEY: MOD_RES
<222> LOCATION: (2)..(2)
<223> OTHER INFORMATION: Xaa is AIB
<220> FEATURE:
```

```
<221> NAME/KEY: MOD_RES
<222> LOCATION: (10)..(10)
<223> OTHER INFORMATION: Acylated with C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 63

His Xaa Gln Gly Thr Phe Thr Ser Asp Lys Ser Lys Tyr Leu Glu Xaa
1               5                   10                  15

Arg Ala Ala Gln Asp Phe Val Gln Trp Leu Met Asp Thr
            20                  25

<210> SEQ ID NO 64
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 49
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 64

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr
            20                  25

<210> SEQ ID NO 65
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 50
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via gamma-
      Glu-gamma-Glu spacer

<400> SEQUENCE: 65

His Xaa Gln Gly Thr Phe Thr Ser Asp Lys Ser Lys Tyr Leu Asp Glu
```

```
                1               5                   10                  15

Arg Ala Ala Gln Asp Phe Val Gln Trp Leu Met Asp Thr
            20                  25

<210> SEQ ID NO 66
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 51
<220> FEATURE:
<221> NAME/KEY: MOD_RES
<222> LOCATION: (2)..(2)
<223> OTHER INFORMATION: d-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 66

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 67
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 52
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 67

His Xaa Gln Gly Thr Phe Thr Ser Asp Lys Ser Lys Tyr Leu Asp Glu
1               5                   10                  15

Gln Ala Ala Lys Glu Phe Ile Ala Trp Leu Leu Asp Thr
            20                  25

<210> SEQ ID NO 68
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 53
<220> FEATURE:
```

```
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (24)..(24)
<223> OTHER INFORMATION: PEGYLATION
<220> FEATURE:
<221> NAME/KEY: MOD_RES
<222> LOCATION: (29)..(29)
<223> OTHER INFORMATION: C-terminal amidation

<400> SEQUENCE: 68

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 69
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 54
<220> FEATURE:
<221> NAME/KEY: MOD_RES
<222> LOCATION: (1)..(1)
<223> OTHER INFORMATION: Xaa is DMIA
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 69

Xaa Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 70
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 57
<220> FEATURE:
<221> NAME/KEY: MOD_RES
<222> LOCATION: (1)..(1)
<223> OTHER INFORMATION: Ac-His
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation
```

```
<400> SEQUENCE: 70

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 71
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 55
<220> FEATURE:
<221> NAME/KEY: MOD_RES
<222> LOCATION: (2)..(2)
<223> OTHER INFORMATION: d-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer

<400> SEQUENCE: 71

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Gly
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 56
<220> FEATURE:
<221> NAME/KEY: MOD_RES
<222> LOCATION: (2)..(2)
<223> OTHER INFORMATION: d-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer

<400> SEQUENCE: 72

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Gly Gly
            20                  25                  30

<210> SEQ ID NO 73
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 58
<220> FEATURE:
<221> NAME/KEY: MOD_RES
<222> LOCATION: (2)..(2)
<223> OTHER INFORMATION: Xaa is AIB
<220> FEATURE:
```

```
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 73

His Xaa Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25

<210> SEQ ID NO 74
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 59
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 74

His Ala Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25

<210> SEQ ID NO 75
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 60
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (39)..(39)
<223> OTHER INFORMATION: C-terminal amidation

<400> SEQUENCE: 75

His Ser Gln Gly Thr Phe Thr Ser Asp Tyr Ser Lys Tyr Leu Asp Xaa
1               5                   10                  15

Lys Arg Ala Lys Glu Phe Val Cys Trp Leu Leu Asp Gly Gly Pro Ser
            20                  25                  30
```

Ser Gly Ala Pro Pro Pro Ser
        35

<210> SEQ ID NO 76
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 61
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (39)..(39)
<223> OTHER INFORMATION: C-terminal amidation

<400> SEQUENCE: 76

His Ser Gln Gly Thr Phe Thr Ser Asp Tyr Ser Lys Tyr Leu Asp Glu
1               5                   10                  15

Lys Arg Ala Lys Glu Phe Val Cys Trp Leu Leu Asp Gly Gly Pro Ser
            20                  25                  30

Ser Gly Ala Pro Pro Pro Ser
        35

<210> SEQ ID NO 77
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 62
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 77

His Ser Gln Gly Thr Phe Thr Ser Asp Lys Ser Lys Tyr Leu Asp Xaa
1               5                   10                  15

Lys Arg Ala Lys Glu Phe Val Cys Trp Leu Leu Asp Thr
            20                  25

<210> SEQ ID NO 78
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 63
<220> FEATURE:

```
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 78

His Ser Gln Gly Thr Phe Thr Ser Asp Lys Ser Lys Tyr Leu Asp Xaa
1               5                   10                  15

Lys Arg Ala Lys Glu Phe Val Cys Trp Leu Leu Asp Thr
            20                  25

<210> SEQ ID NO 79
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 64
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 79

His Xaa Gln Gly Thr Phe Thr Ser Asp Tyr Ser Lys Tyr Leu Asp Xaa
1               5                   10                  15

Lys Ala Ala Lys Glu Phe Val Cys Trp Leu Leu Asp Thr
            20                  25

<210> SEQ ID NO 80
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 65
<220> FEATURE:
<221> NAME/KEY: MISC_FEATURE
<222> LOCATION: (29)..(29)
<223> OTHER INFORMATION: C-terminal amidation

<400> SEQUENCE: 80

His Ser Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr
            20                  25
```

```
<210> SEQ ID NO 81
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 66
<220> FEATURE:
<221> NAME/KEY: MOD_RES
<222> LOCATION: (29)..(29)
<223> OTHER INFORMATION: C-terminal amidation

<400> SEQUENCE: 81

His Ser Gln Gly Thr Phe Thr Ser Asp Tyr Ser Lys Tyr Leu Asp Ser
1               5                   10                  15

Lys Arg Ala Gln Glu Phe Val Gln Trp Leu Met Asn Thr
            20                  25

<210> SEQ ID NO 82
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 67

<400> SEQUENCE: 82

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 83
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 68

<400> SEQUENCE: 83

His Ser Gln Gly Thr Phe Thr Ser Asp Tyr Ser Lys Tyr Leu Asp Glu
1               5                   10                  15

Arg Arg Ala Lys Glu Phe Val Gln Trp Leu Met Asn Thr
            20                  25

<210> SEQ ID NO 84
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 69
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group
<220> FEATURE:
<221> NAME/KEY: MOD_RES
```

<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 84

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 85
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 70
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C14 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 85

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 86
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 71
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C18 fatty acyl group via gamma-
      Glu-gamma-Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 86

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 87
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 74
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (31)..(31)
<223> OTHER INFORMATION: C-terminal amidation

<400> SEQUENCE: 87

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Gly Glu
            20                  25                  30

<210> SEQ ID NO 88
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 75
<220> FEATURE:
<221> NAME/KEY: MOD_RES
<222> LOCATION: (1)..(1)
<223> OTHER INFORMATION: Xaa is Des-amino-His
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 88

Xaa Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 89
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<223> OTHER INFORMATION: Glucagon Analog 76
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer

<400> SEQUENCE: 89

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 90
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 77
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 90

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 91
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 78
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG

<400> SEQUENCE: 91
```

```
His Ser Gln Gly Thr Phe Thr Ser Asp Lys Ser Lys Tyr Leu Asp Glu
1               5                   10                  15
Gln Ala Ala Lys Glu Phe Ile Cys Trp Leu Leu Asp Thr Gly Gly
            20                  25                  30

<210> SEQ ID NO 92
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 79
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG

<400> SEQUENCE: 92

His Ser Gln Gly Thr Phe Thr Ser Asp Lys Ser Lys Tyr Leu Asp Glu
1               5                   10                  15
Gln Ala Ala Lys Glu Phe Ile Cys Trp Leu Leu Asp Thr
            20                  25

<210> SEQ ID NO 93
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 80
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 93

His Xaa Gln Gly Thr Phe Thr Ser Asp Lys Ser Lys Tyr Leu Asp Glu
1               5                   10                  15
Arg Ala Ala Gln Asp Phe Val Cys Trp Leu Leu Asp Thr
            20                  25

<210> SEQ ID NO 94
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: Glucagon Analog 81
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 94

His Ala Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25

<210> SEQ ID NO 95
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 82
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 95

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Glu
            20                  25

<210> SEQ ID NO 96
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 83
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
```

<223> OTHER INFORMATION: Acylated with a C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (30)..(30)
<223> OTHER INFORMATION: C-terminal amidation

<400> SEQUENCE: 96

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Glu
            20                  25                  30

<210> SEQ ID NO 97
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 84
<220> FEATURE:
<221> NAME/KEY: MOD_RES
<222> LOCATION: (2)..(2)
<223> OTHER INFORMATION: D-Ser

<400> SEQUENCE: 97

His Ser Gln Gly Thr Phe Thr Ser Asp Tyr Ser Lys Tyr Leu Asp Glu
1               5                   10                  15

Gln Ala Val Arg Leu Phe Ile Cys Trp Leu Leu Asp Gly Gly Pro Ser
            20                  25                  30

Ser Gly Ala Pro Pro Pro Ser
        35

<210> SEQ ID NO 98
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 85
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 98

His Ser Gln Gly Thr Phe Thr Ser Asp Lys Ser Lys Tyr Leu Asp Glu
1               5                   10                  15

Gln Ala Val Arg Leu Phe Ile Cys Trp Leu Leu Asp Thr
            20                  25

<210> SEQ ID NO 99
<211> LENGTH: 29

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 86
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 99

His Ser Gln Gly Thr Phe Thr Ser Asp Tyr Ser Lys Tyr Leu Asp Xaa
1               5                   10                  15

Lys Ala Val Arg Leu Phe Ile Cys Trp Leu Leu Asp Thr
            20                  25

<210> SEQ ID NO 100
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 87
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (29)..(29)
<223> OTHER INFORMATION: C-terminal amidation

<400> SEQUENCE: 100

His Ser Gln Gly Thr Phe Thr Ser Asp Tyr Ser Lys Tyr Leu Asp Glu
1               5                   10                  15

Gln Ala Val Arg Leu Phe Ile Cys Trp Leu Leu Asp Thr
            20                  25

<210> SEQ ID NO 101
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 88
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 101
```

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Glu
            20                  25

<210> SEQ ID NO 102
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 89
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (29)..(29)
<223> OTHER INFORMATION: C-terminal amidation

<400> SEQUENCE: 102

His Ser Gln Gly Thr Phe Thr Ser Asp Tyr Ser Leu Tyr Leu Asp Glu
1               5                   10                  15

Gln Ala Ala Lys Glu Phe Ile Cys Trp Leu Leu Asp Thr
            20                  25

<210> SEQ ID NO 103
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 90
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (29)..(29)
<223> OTHER INFORMATION: C-terminal amidation

<400> SEQUENCE: 103

His Ser Gln Gly Thr Phe Thr Ser Asp Tyr Ser Lys Tyr Leu Asp Glu
1               5                   10                  15

Arg Ala Ala Lys Asp Phe Val Cys Trp Leu Leu Asp Thr
            20                  25

<210> SEQ ID NO 104
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 91
<220> FEATURE:

```
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 104

His Ser Gln Gly Thr Phe Thr Ser Asp Tyr Ser Leu Tyr Leu Asp Glu
1               5                   10                  15

Arg Ala Ala Lys Asp Phe Val Cys Trp Leu Leu Asp Thr
            20                  25

<210> SEQ ID NO 105
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 92
<220> FEATURE:
<221> NAME/KEY: MOD_RES
<222> LOCATION: (2)..(2)
<223> OTHER INFORMATION: D-Ser
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 105

His Ser Gln Gly Thr Phe Thr Ser Asp Tyr Ser Lys Tyr Leu Asp Glu
1               5                   10                  15

Gln Ala Ala Lys Glu Phe Ile Cys Trp Leu Leu Asp Thr
            20                  25

<210> SEQ ID NO 106
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 93
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
```

```
<223> OTHER INFORMATION: Covalently bound to 40kDa PEG
<220> FEATURE:
<221> NAME/KEY: MOD_RES
<222> LOCATION: (39)..(39)
<223> OTHER INFORMATION: C-terminal amidation

<400> SEQUENCE: 106

His Ser Gln Gly Thr Phe Thr Ser Asp Tyr Ser Lys Tyr Leu Asp Xaa
1               5                   10                  15

Lys Arg Ala Lys Glu Phe Val Cys Trp Leu Leu Asp Gly Gly Pro Ser
            20                  25                  30

Ser Gly Ala Pro Pro Pro Ser
        35

<210> SEQ ID NO 107
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 94
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (39)..(39)
<223> OTHER INFORMATION: C-terminal amidation

<400> SEQUENCE: 107

His Ser Gln Gly Thr Phe Thr Ser Asp Tyr Ser Lys Tyr Leu Asp Glu
1               5                   10                  15

Lys Arg Ala Lys Glu Phe Val Cys Trp Leu Leu Asp Gly Gly Pro Ser
            20                  25                  30

Ser Gly Ala Pro Pro Pro Ser
        35

<210> SEQ ID NO 108
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 95
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 108

His Ser Gln Gly Thr Phe Thr Ser Asp Lys Ser Lys Tyr Leu Asp Glu
1               5                   10                  15
```

```
Gln Ala Ala Lys Glu Phe Ile Cys Trp Leu Leu Asp Glu
        20                  25

<210> SEQ ID NO 109
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 96
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (24)..(24)
<223> OTHER INFORMATION: Covalently bound to a 40kDa PEG
<220> FEATURE:
<221> NAME/KEY: MOD_RES
<222> LOCATION: (30)..(30)
<223> OTHER INFORMATION: C-terminal amidation

<400> SEQUENCE: 109

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Glu
        20                  25                  30

<210> SEQ ID NO 110
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 97
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with C16 fatty acyl group via gamma-
      Glu spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to a 40kDa PEG
<220> FEATURE:
<221> NAME/KEY: MOD_RES
<222> LOCATION: (29)..(29)
<223> OTHER INFORMATION: C-terminal amidation

<400> SEQUENCE: 110

His Ser Gln Gly Thr Phe Thr Ser Asp Lys Ser Lys Tyr Leu Asp Xaa
1               5                   10                  15

Lys Arg Ala Lys Glu Phe Val Cys Trp Leu Leu Asp Thr
        20                  25
```

```
<210> SEQ ID NO 111
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 98
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to a 40kDa PEG
<220> FEATURE:
<221> NAME/KEY: MOD_RES
<222> LOCATION: (29)..(29)
<223> OTHER INFORMATION: C-terminal amidation

<400> SEQUENCE: 111

His Xaa Gln Gly Thr Phe Thr Ser Asp Tyr Ser Lys Tyr Leu Asp Xaa
1               5                   10                  15

Lys Ala Ala Lys Glu Phe Val Cys Trp Leu Leu Asp Thr
            20                  25

<210> SEQ ID NO 112
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 99
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 112

His Ser Gln Gly Thr Phe Thr Ser Asp Tyr Ser Lys Tyr Leu Asp Xaa
1               5                   10                  15

Lys Ala Val Arg Leu Phe Ile Cys Trp Leu Leu Asp Thr
            20                  25

<210> SEQ ID NO 113
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 100
<220> FEATURE:
```

```
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 113

His Ser Gln Gly Thr Phe Thr Ser Asp Tyr Ser Lys Tyr Leu Asp Glu
1               5                   10                  15

Gln Ala Val Arg Leu Phe Ile Cys Trp Leu Leu Asp Thr
            20                  25

<210> SEQ ID NO 114
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 101
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 114

Xaa Ser Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 115
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog A
<220> FEATURE:
<221> NAME/KEY: MOD_RES
<222> LOCATION: (29)..(29)
<223> OTHER INFORMATION: C-terminal amidation

<400> SEQUENCE: 115

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr
            20                  25

<210> SEQ ID NO 116
<211> LENGTH: 29
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<223> OTHER INFORMATION: Analog B
<220> FEATURE:
<221> NAME/KEY: MOD_RES
<222> LOCATION: (29)..(29)
<223> OTHER INFORMATION: C-terminal amidation

<400> SEQUENCE: 116

His Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 117
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog C
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 117

His Xaa Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr
            20                  25

<210> SEQ ID NO 118
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog D
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 118

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 119
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<223> OTHER INFORMATION: Glucagon analog 79
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer

<400> SEQUENCE: 119

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 120
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 83
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (30)..(30)
<223> OTHER INFORMATION: C-terminal amidation

<400> SEQUENCE: 120

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Glu
            20                  25                  30

<210> SEQ ID NO 121
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (29)..(29)
<223> OTHER INFORMATION: C-terminal amidation

<400> SEQUENCE: 121

His Xaa Gln Gly Thr Phe Thr Ser Asp Lys Ser Lys Tyr Leu Asp Xaa
1               5                   10                  15
```

Arg Ala Ala Gln Asp Phe Val Gln Trp Leu Met Asp Thr
            20                  25

<210> SEQ ID NO 122
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via acid
      amino acidic spacer
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (29)..(29)
<223> OTHER INFORMATION: C-terminal amidation

<400> SEQUENCE: 122

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 123
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 230
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 123

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 124
<211> LENGTH: 29
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: Glucagon Analog 237
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 124

His Ser Gln Gly Thr Phe Thr Ser Asp Lys Ser Lys Tyr Leu Asp Glu
1               5                   10                  15

Glu Ala Val Arg Leu Phe Ile Glu Trp Leu Met Asn Thr
            20                  25

<210> SEQ ID NO 125
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 238
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 125

His Xaa Gln Gly Thr Phe Thr Ser Asp Lys Ser Lys Tyr Leu Asp Glu
1               5                   10                  15

Glu Ala Val Arg Leu Phe Ile Glu Trp Leu Met Asn Thr
            20                  25

<210> SEQ ID NO 126
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 242
<220> FEATURE:
<221> NAME/KEY: MOD_RES
<222> LOCATION: (2)..(2)
<223> OTHER INFORMATION: Xaa is Aminoisobutyric acid
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation
```

<400> SEQUENCE: 126

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 127
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 243
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 127

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 128
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 245
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 128

His Xaa Glu Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

```
<210> SEQ ID NO 129
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 246
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids
<220> FEATURE:
<221> NAME/KEY: MOD_RES
<222> LOCATION: (16)..(16)
<223> OTHER INFORMATION: Xaa is AIB

<400> SEQUENCE: 129

His Xaa Gln Gly Thr Phe Ile Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 130
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 248
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 130

His Xaa Gln Gly Thr Phe Thr Ser Asp Lys Ser Lys Tyr Leu Glu Xaa
1               5                   10                  15

Arg Ala Ala Gln Asp Phe Val Gln Trp Leu Met Asp Thr
            20                  25

<210> SEQ ID NO 131
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 249
<220> FEATURE:
```

```
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 131

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr
            20                  25

<210> SEQ ID NO 132
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 250
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids

<400> SEQUENCE: 132

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Met Asp Thr
            20                  25

<210> SEQ ID NO 133
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 252
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 133

His Xaa Gln Gly Thr Phe Thr Ser Asp Lys Ser Lys Tyr Leu Asp Glu
```

-continued

```
                1               5                  10                  15
Gln Ala Ala Lys Glu Phe Ile Ala Trp Leu Leu Asp Thr
                20                  25

<210> SEQ ID NO 134
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 254
<220> FEATURE:
<221> NAME/KEY: MOD_RES
<222> LOCATION: (1)..(1)
<223> OTHER INFORMATION: Xaa is DMIA
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 134

Xaa Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
                20                  25

<210> SEQ ID NO 135
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 257
<220> FEATURE:
<221> NAME/KEY: MOD_RES
<222> LOCATION: (1)..(1)
<223> OTHER INFORMATION: Ac-His
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 135

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
                20                  25

<210> SEQ ID NO 136
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 258
<220> FEATURE:
```

```
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 136

His Xaa Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25

<210> SEQ ID NO 137
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 259
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 137

His Ala Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25

<210> SEQ ID NO 138
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 270
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation
```

<400> SEQUENCE: 138

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 139
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 271
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with a C16 fatty acyl group via
      dipeptide spacer of two acidic amino acids
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 139

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 140
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 274
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser,
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (31)..(31)
<223> OTHER INFORMATION: C-terminal amidation

<400> SEQUENCE: 140

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Gly Glu
            20                  25                  30

<210> SEQ ID NO 141

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 275
<220> FEATURE:
<221> NAME/KEY: MOD_RES
<222> LOCATION: (1)..(1)
<223> OTHER INFORMATION: Xaa is Des-amino-His
<220> FEATURE:
<221> NAME/KEY: MOD_RES
<222> LOCATION: (10)..(10)
<223> OTHER INFORMATION: Acylated with C16 fatty acyl group via acidic
     amino acid spacer
<220> FEATURE:
<221> NAME/KEY: MOD_RES
<222> LOCATION: (29)..(29)
<223> OTHER INFORMATION: C-terminal amidation

<400> SEQUENCE: 141

Xaa Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 142
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 280
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (10)..(10)
<223> OTHER INFORMATION: Acylated with C16 fatty acyl group via acidic
     amino acid spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 142

His Xaa Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25

<210> SEQ ID NO 143
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 222
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
```

-continued

```
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MISC_FEATURE
<222> LOCATION: (15)..(20)
<223> OTHER INFORMATION: Salt bridge
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (16)..(21)
<223> OTHER INFORMATION: Salt bridge
<220> FEATURE:
<221> NAME/KEY: MOD_RES
<222> LOCATION: (29)..(29)
<223> OTHER INFORMATION: C-terminal amidation

<400> SEQUENCE: 143

His Xaa Gln Gly Thr Phe Thr Ser Asp Lys Ser Lys Tyr Leu Asp Xaa
1               5                   10                  15

Lys Arg Ala Lys Glu Phe Val Gln Trp Leu Met Asn Thr
            20                  25

<210> SEQ ID NO 144
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 229
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 144

His Xaa Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25

<210> SEQ ID NO 145
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 244
<220> FEATURE:
<221> NAME/KEY: MOD_RES
```

```
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via
      dipeptide spacer of two acidic residues
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 145

His Xaa Gln Gly Thr Phe Thr Ser Asp Lys Ser Lys Tyr Leu Glu Xaa
1               5                   10                  15

Arg Ala Ala Gln Asp Phe Val Gln Trp Leu Met Asp Thr
            20                  25

<210> SEQ ID NO 146
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 251
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 146

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 147
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 253
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
```

```
<222> LOCATION: (24)..(24)
<223> OTHER INFORMATION: PEGYLATION
<220> FEATURE:
<221> NAME/KEY: MOD_RES
<222> LOCATION: (29)..(29)
<223> OTHER INFORMATION: C-terminal amidation

<400> SEQUENCE: 147

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 148
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 55
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser,
      or alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer

<400> SEQUENCE: 148

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Gly
            20                  25                  30

<210> SEQ ID NO 149
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 256
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer

<400> SEQUENCE: 149

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Gly Gly
            20                  25                  30

<210> SEQ ID NO 150
<211> LENGTH: 29
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<223> OTHER INFORMATION: Glucagon Analog 262
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 150

His Xaa Gln Gly Thr Phe Thr Ser Asp Lys Ser Lys Tyr Leu Asp Xaa
1               5                   10                  15

Lys Arg Ala Lys Glu Phe Val Cys Trp Leu Leu Asp Thr
            20                  25

<210> SEQ ID NO 151
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 263
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via
      dipeptide spacer of two acidic residues
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (29)..(29)
<223> OTHER INFORMATION: C-terminal amidation

<400> SEQUENCE: 151

His Xaa Gln Gly Thr Phe Thr Ser Asp Lys Ser Lys Tyr Leu Asp Xaa
1               5                   10                  15

Lys Arg Ala Lys Glu Phe Val Cys Trp Leu Leu Asp Thr
            20                  25

<210> SEQ ID NO 152
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 276
<220> FEATURE:
<221> NAME/KEY: MOD_RES
<222> LOCATION: (2)..(2)
```

-continued

<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer

<400> SEQUENCE: 152

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 153
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 277
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 153

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 154
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 278
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to 40kDa PEG

<400> SEQUENCE: 154

-continued

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Gly Gly
            20                  25                  30

<210> SEQ ID NO 155
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 279
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to 40kDa PEG

<400> SEQUENCE: 155

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

<210> SEQ ID NO 156
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 282
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 156

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Glu
            20                  25

<210> SEQ ID NO 157
<211> LENGTH: 30
<212> TYPE: PRT
<213> ORGANISM: Artificial Sequence
<220> FEATURE:
<223> OTHER INFORMATION: Synthetic peptide
<220> FEATURE:

```
<221> NAME/KEY: MISC_FEATURE
<223> OTHER INFORMATION: Glucagon Analog 283
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (30)..(30)
<223> OTHER INFORMATION: C-terminal amidation

<400> SEQUENCE: 157

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Glu
            20                  25                  30

<210> SEQ ID NO 158
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 285
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 158

His Ser Gln Gly Thr Phe Thr Ser Asp Lys Ser Lys Tyr Leu Asp Glu
1               5                   10                  15

Gln Ala Val Arg Leu Phe Ile Cys Trp Leu Leu Asp Thr
            20                  25

<210> SEQ ID NO 159
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 288
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
```

```
<223> OTHER INFORMATION: Acylated with C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 159

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Glu
            20                  25

<210> SEQ ID NO 160
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 295
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 160

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Glu
            20                  25

<210> SEQ ID NO 161
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 296
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to a 40kDa PEG
<220> FEATURE:
<221> NAME/KEY: MOD_RES
<222> LOCATION: (30)..(30)
<223> OTHER INFORMATION: C-terminal amidation
```

<400> SEQUENCE: 161

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Glu
            20                  25                  30

<210> SEQ ID NO 162
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 297
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to a 40kDa PEG
<220> FEATURE:
<221> NAME/KEY: MOD_RES
<222> LOCATION: (29)..(29)
<223> OTHER INFORMATION: C-terminal amidation

<400> SEQUENCE: 162

His Ser Gln Gly Thr Phe Thr Ser Asp Lys Ser Lys Tyr Leu Asp Xaa
1               5                   10                  15

Lys Arg Ala Lys Glu Phe Val Cys Trp Leu Leu Asp Thr
            20                  25

<210> SEQ ID NO 163
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon analog 279
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer

<400> SEQUENCE: 163

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr
            20                  25

```
<210> SEQ ID NO 164
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 283
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (30)..(30)
<223> OTHER INFORMATION: C-terminal amidation

<400> SEQUENCE: 164

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Leu Asp Thr Glu
            20                  25                  30

<210> SEQ ID NO 165
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 220
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (29)..(29)
<223> OTHER INFORMATION: C-terminal amidation

<400> SEQUENCE: 165

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr
            20                  25

<210> SEQ ID NO 166
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 221
<220> FEATURE:
<221> NAME/KEY: MOD_RES
```

```
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (29)..(29)
<223> OTHER INFORMATION: C-terminal amidation

<400> SEQUENCE: 166

His Xaa Gln Gly Thr Phe Thr Ser Asp Tyr Ser Lys Tyr Leu Asp Xaa
1               5                   10                  15

Lys Arg Ala Lys Glu Phe Val Gln Trp Leu Met Asn Thr
            20                  25

<210> SEQ ID NO 167
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 224
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 167

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
            20                  25

<210> SEQ ID NO 168
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 226
<220> FEATURE:
<221> NAME/KEY: MOD_RES
```

```
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MISC_FEATURE
<222> LOCATION: (16)..(20)
<223> OTHER INFORMATION: Salt bridge
<220> FEATURE:
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 168

His Xaa Gln Gly Thr Phe Thr Ser Asp Tyr Ser Lys Tyr Leu Asp Xaa
1               5                   10                  15

Lys Arg Ala Lys Glu Phe Val Cys Trp Leu Met Asn Thr
            20                  25

<210> SEQ ID NO 169
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 231
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (29)..(29)
<223> OTHER INFORMATION: C-terminal amidation

<400> SEQUENCE: 169

His Xaa Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr
            20                  25

<210> SEQ ID NO 170
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 233
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MISC_FEATURE
<222> LOCATION: (16)..(20)
<223> OTHER INFORMATION: Salt bridge
<220> FEATURE:
```

```
<221> NAME/KEY: MISC_FEATURE
<222> LOCATION: (17)..(21)
<223> OTHER INFORMATION: Salt bridge
<220> FEATURE:
<221> NAME/KEY: MOD_RES
<222> LOCATION: (29)..(29)
<223> OTHER INFORMATION: C-terminal amidation

<400> SEQUENCE: 170

His Xaa Gln Gly Thr Phe Thr Ser Asp Tyr Ser Lys Tyr Leu Asp Glu
1               5                   10                  15

Glu Ala Val Arg Leu Phe Ile Cys Trp Leu Met Asn Thr
            20                  25

<210> SEQ ID NO 171
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 235
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
     alpha, amino isobutyric acid
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 171

His Xaa Gln Gly Thr Phe Thr Ser Asp Tyr Ser Lys Tyr Leu Asp Glu
1               5                   10                  15

Glu Ala Val Arg Leu Phe Ile Cys Trp Leu Met Asn Thr
            20                  25

<210> SEQ ID NO 172
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 260
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
     alpha, amino isobutyric acid
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (39)..(39)
<223> OTHER INFORMATION: C-terminal amidation

<400> SEQUENCE: 172

His Xaa Gln Gly Thr Phe Thr Ser Asp Tyr Ser Lys Tyr Leu Asp Xaa
1               5                   10                  15

Lys Arg Ala Lys Glu Phe Val Cys Trp Leu Leu Asp Gly Gly Pro Ser
            20                  25                  30
```

Ser Gly Ala Pro Pro Pro Ser
        35

<210> SEQ ID NO 173
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 261
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (39)..(39)
<223> OTHER INFORMATION: C-terminal amidation

<400> SEQUENCE: 173

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Leu Asp Gly Gly Pro Ser
            20                  25                  30

Ser Gly Ala Pro Pro Pro Ser
        35

<210> SEQ ID NO 174
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 284
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid

<400> SEQUENCE: 174

His Xaa Gln Gly Thr Phe Thr Ser Asp Tyr Ser Lys Tyr Leu Asp Glu
1               5                   10                  15

Gln Ala Val Arg Leu Phe Ile Cys Trp Leu Leu Asp Gly Gly Pro Ser
            20                  25                  30

Ser Gly Ala Pro Pro Pro Ser
        35

<210> SEQ ID NO 175
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 286
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (16)..(16)
<223> OTHER INFORMATION: Xaa is AIB

```
<220> FEATURE:
<221> NAME/KEY: MOD_RES
<222> LOCATION: (29)..(29)
<223> OTHER INFORMATION: C-terminal amidation

<400> SEQUENCE: 175

His Xaa Gln Gly Thr Phe Thr Ser Asp Tyr Ser Lys Tyr Leu Asp Xaa
1               5                   10                  15

Lys Ala Val Arg Leu Phe Ile Cys Trp Leu Leu Asp Thr
            20                  25

<210> SEQ ID NO 176
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 287
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
     alpha, amino isobutyric acid
<220> FEATURE:
<221> NAME/KEY: MOD_RES
<222> LOCATION: (29)..(29)
<223> OTHER INFORMATION: C-terminal amidation

<400> SEQUENCE: 176

His Xaa Gln Gly Thr Phe Thr Ser Asp Tyr Ser Lys Tyr Leu Asp Glu
1               5                   10                  15

Gln Ala Val Arg Leu Phe Ile Cys Trp Leu Leu Asp Thr
            20                  25

<210> SEQ ID NO 177
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 289
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
     alpha, amino isobutyric acid
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (29)..(29)
<223> OTHER INFORMATION: C-terminal amidation

<400> SEQUENCE: 177

His Xaa Gln Gly Thr Phe Thr Ser Asp Tyr Ser Leu Tyr Leu Asp Glu
1               5                   10                  15

Gln Ala Ala Lys Glu Phe Ile Cys Trp Leu Leu Asp Thr
            20                  25

<210> SEQ ID NO 178
<211> LENGTH: 29
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<223> OTHER INFORMATION: Glucagon Analog 290
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (29)..(29)
<223> OTHER INFORMATION: C-terminal amidation

<400> SEQUENCE: 178

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Leu Asp Thr
            20                  25

<210> SEQ ID NO 179
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 291
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MISC_FEATURE
<222> LOCATION: (16)..(20)
<223> OTHER INFORMATION: Lactam ring between side chains of amino acids
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 179

His Xaa Gln Gly Thr Phe Thr Ser Asp Tyr Ser Leu Tyr Leu Asp Glu
1               5                   10                  15

Arg Ala Ala Lys Asp Phe Val Cys Trp Leu Leu Asp Thr
            20                  25

<210> SEQ ID NO 180
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 292
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MISC_FEATURE
<222> LOCATION: (16)..(20)
<223> OTHER INFORMATION: Lactam ring between side chains of amino acids
```

```
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 180

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Leu Asp Thr
            20                  25

<210> SEQ ID NO 181
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 293
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (39)..(39)
<223> OTHER INFORMATION: C-terminal amidation

<400> SEQUENCE: 181

His Xaa Gln Gly Thr Phe Thr Ser Asp Tyr Ser Lys Tyr Leu Asp Xaa
1               5                   10                  15

Lys Arg Ala Lys Glu Phe Val Cys Trp Leu Leu Asp Gly Gly Pro Ser
            20                  25                  30

Ser Gly Ala Pro Pro Ser
        35

<210> SEQ ID NO 182
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 294
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (39)..(39)
<223> OTHER INFORMATION: C-terminal amidation

<400> SEQUENCE: 182

His Xaa Gln Gly Thr Phe Thr Ser Asp Tyr Ser Lys Tyr Leu Asp Glu
1               5                   10                  15
```

-continued

```
Lys Arg Ala Lys Glu Phe Val Cys Trp Leu Leu Asp Gly Gly Pro Ser
            20                  25                  30
Ser Gly Ala Pro Pro Pro Ser
        35

<210> SEQ ID NO 183
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 299
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 183

His Xaa Gln Gly Thr Phe Thr Ser Asp Tyr Ser Lys Tyr Leu Asp Xaa
1               5                   10                  15
Lys Ala Val Arg Leu Phe Ile Cys Trp Leu Leu Asp Thr
            20                  25

<210> SEQ ID NO 184
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 2100
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser, or
      alpha, amino isobutyric acid
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 184

His Xaa Gln Gly Thr Phe Thr Ser Asp Tyr Ser Lys Tyr Leu Asp Glu
1               5                   10                  15
Gln Ala Val Arg Leu Phe Ile Cys Trp Leu Leu Asp Thr
            20                  25

<210> SEQ ID NO 185
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser,
      alpha, amino isobutyric acid
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 185

His Xaa Gln Gly Thr Phe Thr Ser Asp Tyr Ser Lys Tyr Leu Asp Glu
1               5                   10                  15

Glu Ala Val Arg Leu Phe Ile Cys Trp Leu Met Asn Thr
            20                  25

<210> SEQ ID NO 186
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser,
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via gamma-
      Glu spacer
<220> FEATURE:
<221> NAME/KEY: MOD_RES
<222> LOCATION: (29)..(29)
<223> OTHER INFORMATION: C-terminal amidation

<400> SEQUENCE: 186

His Xaa Gln Gly Thr Phe Thr Ser Asp Tyr Ser Lys Tyr Leu Asp Glu
1               5                   10                  15

Glu Ala Val Arg Leu Phe Ile Cys Trp Leu Met Asn Thr
            20                  25

<210> SEQ ID NO 187
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is D-Ser, D-Ala, Val, Gly, N-methyl Ser,
      alpha, amino isobutyric acid
<220> FEATURE:
<221> NAME/KEY: MOD_RES
<222> LOCATION: (10)..(10)
<223> OTHER INFORMATION: Acylated with a C16 fatty acyl group via acidic
      amino acid spacer
<220> FEATURE:
<221> NAME/KEY: MOD_RES
<222> LOCATION: (29)..(29)
<223> OTHER INFORMATION: C-terminal amidation

<400> SEQUENCE: 187

His Xaa Gln Gly Thr Phe Thr Ser Asp Tyr Ser Lys Tyr Leu Asp Glu
1               5                   10                  15
```

```
Glu Ala Val Arg Leu Phe Ile Cys Trp Leu Met Asn Thr
            20                  25

<210> SEQ ID NO 188
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Analog 281
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (10)..(10)
<223> OTHER INFORMATION: Acylated with C16 fatty acyl group via acidic
      amino acid spacer
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: C-terminal amidation

<400> SEQUENCE: 188

His Ala Gln Gly Thr Phe Thr Ser Asp Lys Ser Lys Tyr Leu Asp Glu
1               5                   10                  15

Arg Ala Ala Gln Asp Phe Val Cys Trp Leu Leu Asp Thr
            20                  25
```